(12) United States Patent
Weinstein et al.

(10) Patent No.: US 11,020,002 B2
(45) Date of Patent: Jun. 1, 2021

(54) SYSTEMS, DEVICES AND METHODS FOR PHYSIOLOGICAL MONITORING OF PATIENTS

(71) Applicant: Zoll Medical Israel Ltd., Kfar-Saba (IL)

(72) Inventors: Uriel Weinstein, Mazkeret Batya (IL); Rafi Ravid, Savyon (IL); David Meshulam, Hod Hasharon (IL); Roman Vaistikh, Ganey Tikva (IL); Leonid Bekman, Holon (IL); Noa Graf, Tel Aviv (IL); Ronen Eldar, Beit Hashmonai (IL); Daniel Quartler, Holon (IL); Arkadi Averbuch, Rehovot (IL); Vered Cohen Sharvit, Modiin (IL)

(73) Assignee: ZOLL MEDICAL ISRAEL LTD., Kfar Saba (IL)

( * ) Notice: Subject to any disclaimer, the term of this patent is extended or adjusted under 35 U.S.C. 154(b) by 409 days.

(21) Appl. No.: 16/041,402

(22) Filed: Jul. 20, 2018

(65) Prior Publication Data
US 2019/0046038 A1   Feb. 14, 2019

Related U.S. Application Data

(60) Provisional application No. 62/543,803, filed on Aug. 10, 2017.

(51) Int. Cl.
*A61B 5/00* (2006.01)
*G16H 50/20* (2018.01)
(Continued)

(52) U.S. Cl.
CPC .......... *A61B 5/0024* (2013.01); *A61B 5/0006* (2013.01); *A61B 5/0507* (2013.01);
(Continued)

(58) Field of Classification Search
CPC ..... A61B 5/0024; A61B 5/349; A61B 5/0006; A61B 5/4875; A61B 5/7282;
(Continued)

(56) References Cited

U.S. PATENT DOCUMENTS

| 4,240,445 A | 12/1980 | Durney et al. |
| 4,344,440 A | 8/1982 | Aaby et al. |

(Continued)

FOREIGN PATENT DOCUMENTS

| CN | 101032400 A | 9/2007 |
| CN | 101516437 A | 8/2009 |

(Continued)

OTHER PUBLICATIONS

Alekseev, S. I., et al. "Human Skin permittivity determined by millimeter wave reflection measurements", Bioelectromagnetics, vol. 28, No. 5, Jul. 1, 2007, pp. 331-339.

(Continued)

*Primary Examiner* — Tammie K Marlen
(74) *Attorney, Agent, or Firm* — Cooley LLP

(57) ABSTRACT

Some embodiments of the current disclosure are directed toward physiological monitoring of patients, and more particularly, systems, devices and methods for physiological monitoring of patients with a continuous or near-continuous transmission and analysis of monitored physiological data during the monitoring process. In some embodiments, a physiological patient monitoring system is provided which includes a physiological monitoring device which comprises a housing disposed on a patch, and the patch is configured for removable attachment to or proximate the skin of a patient, the housing including at least one memory. Antenna disposed on the housing transmit radio-frequency (RF) waves towards a targeted portion of an internal tissue of the patient and receive reflected RF waves from the internal (Continued)

tissue. RF circuitry in communication with the at least one memory perform an RF-based measurement of a lung fluid level of the patient during a predetermined time period.

19 Claims, 20 Drawing Sheets

(51) Int. Cl.
| | |
|---|---|
| *G16H 40/67* | (2018.01) |
| *A61B 5/0507* | (2021.01) |
| *G16H 40/63* | (2018.01) |
| *A61B 5/349* | (2021.01) |
| *A61B 5/11* | (2006.01) |
| *G16H 50/30* | (2018.01) |
| *A61B 5/024* | (2006.01) |

(52) U.S. Cl.
CPC ............ *A61B 5/349* (2021.01); *A61B 5/4875* (2013.01); *A61B 5/7282* (2013.01); *G16H 40/63* (2018.01); *G16H 40/67* (2018.01); *G16H 50/20* (2018.01); *A61B 5/0022* (2013.01); *A61B 5/0031* (2013.01); *A61B 5/02405* (2013.01); *A61B 5/1113* (2013.01); *A61B 5/6802* (2013.01); *A61B 5/6833* (2013.01); *A61B 5/7275* (2013.01); *G16H 50/30* (2018.01)

(58) Field of Classification Search
CPC . A61B 5/0022; A61B 5/0031; A61B 5/02405; A61B 5/1113; A61B 5/6802; A61B 5/6833; A61B 5/7275; G16H 40/67; G16H 50/20; G16H 50/30; G16H 40/63
See application file for complete search history.

(56) References Cited

U.S. PATENT DOCUMENTS

| | | | |
|---|---|---|---|
| 4,557,272 A | 12/1985 | Carr | |
| 4,632,128 A | 12/1986 | Paglione et al. | |
| 4,640,280 A | 2/1987 | Sterzer | |
| 4,641,659 A | 2/1987 | Sepponen | |
| 4,774,961 A | 10/1988 | Carr | |
| 4,825,880 A | 5/1989 | Stauffer et al. | |
| 4,926,868 A | 5/1990 | Larsen | |
| 4,945,914 A | 8/1990 | Allen | |
| 4,958,638 A | 9/1990 | Sharpe | |
| 4,986,870 A | 1/1991 | Frohlich | |
| 5,003,622 A | 3/1991 | Ma et al. | |
| 5,109,855 A | 5/1992 | Guner | |
| 5,394,882 A | 3/1995 | Mawhinney | |
| 5,404,877 A | 4/1995 | Nolan | |
| 5,474,574 A | 12/1995 | Payne et al. | |
| 5,540,727 A | 7/1996 | Tockman et al. | |
| 5,549,650 A | 8/1996 | Bornzin et al. | |
| 5,668,555 A | 9/1997 | Starr | |
| 5,704,355 A | 1/1998 | Bridges | |
| 5,766,208 A | 6/1998 | McEwan | |
| 5,807,257 A | 9/1998 | Bridges | |
| 5,829,437 A | 11/1998 | Bridges | |
| 5,841,288 A | 11/1998 | Meaney et al. | |
| 5,865,177 A | 2/1999 | Segawa | |
| 5,967,986 A | 10/1999 | Cimochowski et al. | |
| 6,019,724 A | 2/2000 | Gronningsaeter et al. | |
| 6,061,589 A | 5/2000 | Bridges et al. | |
| 6,064,903 A | 5/2000 | Riechers et al. | |
| 6,093,141 A | 7/2000 | Mosseri et al. | |
| 6,144,344 A | 11/2000 | Kim | |
| 6,161,036 A | 12/2000 | Matsumara et al. | |
| 6,193,669 B1 | 2/2001 | Degany et al. | |
| 6,208,286 B1 | 3/2001 | Rostislavovich et al. | |
| 6,233,479 B1 | 5/2001 | Haddad et al. | |
| 6,267,723 B1 | 7/2001 | Matsumura et al. | |
| 6,330,479 B1 | 12/2001 | Stauffer | |
| 6,409,662 B1 | 6/2002 | Lloyd et al. | |
| 6,454,711 B1 | 9/2002 | Haddad et al. | |
| 6,471,655 B1 | 10/2002 | Baura | |
| 6,480,733 B1 | 11/2002 | Turcott | |
| 6,526,318 B1 | 2/2003 | Ansarinia | |
| 6,592,518 B2 | 7/2003 | Denker et al. | |
| 6,604,404 B2 | 8/2003 | Paltieli et al. | |
| 6,729,336 B2 | 5/2004 | Da Silva et al. | |
| 6,730,033 B2 | 5/2004 | Yao et al. | |
| 6,755,856 B2 | 6/2004 | Fierens et al. | |
| 6,933,811 B2 | 8/2005 | Enokihara et al. | |
| 6,940,457 B2 | 9/2005 | Lee et al. | |
| 7,020,508 B2 | 3/2006 | Stivoric et al. | |
| 7,122,012 B2 | 10/2006 | Bouton et al. | |
| 7,130,681 B2 | 10/2006 | Gebhardt et al. | |
| 7,184,824 B2 | 2/2007 | Hashimshony | |
| 7,191,000 B2 | 3/2007 | Zhu et al. | |
| 7,197,356 B2 | 3/2007 | Carr | |
| 7,266,407 B2 | 9/2007 | Li et al. | |
| 7,267,651 B2 | 9/2007 | Nelson | |
| 7,272,431 B2 | 9/2007 | McGrath | |
| 7,280,863 B2 | 10/2007 | Shachar | |
| 7,454,242 B2 | 11/2008 | Fear et al. | |
| 7,474,918 B2 | 1/2009 | Frants et al. | |
| 7,479,790 B2 | 1/2009 | Choi | |
| 7,493,154 B2 | 2/2009 | Bonner et al. | |
| 7,529,398 B2 | 5/2009 | Zwirn et al. | |
| 7,570,063 B2 | 8/2009 | Van Veen et al. | |
| 7,591,792 B2 | 9/2009 | Bouton | |
| 7,697,972 B2 | 4/2010 | Verard et al. | |
| 7,719,280 B2 | 5/2010 | Lagae et al. | |
| 7,747,302 B2 | 6/2010 | Milledge et al. | |
| 7,868,627 B2 | 1/2011 | Turkovskyi | |
| 8,032,211 B2 | 10/2011 | Hashimshony et al. | |
| 8,211,040 B2 | 7/2012 | Kojima et al. | |
| 8,295,920 B2 | 10/2012 | Bouton et al. | |
| 8,352,015 B2 | 1/2013 | Bernstein et al. | |
| 8,473,054 B2 | 6/2013 | Pillai et al. | |
| 8,682,399 B2 | 3/2014 | Rabu | |
| 8,882,759 B2 | 11/2014 | Manley et al. | |
| 8,938,292 B2 | 1/2015 | Hettrick et al. | |
| 8,983,592 B2 | 3/2015 | Belalcazar | |
| 8,989,837 B2 | 3/2015 | Weinstein et al. | |
| 9,220,420 B2 | 12/2015 | Weinstein et al. | |
| 9,265,438 B2 | 2/2016 | Weinstein et al. | |
| 9,572,512 B2 | 2/2017 | Weinstein et al. | |
| 9,629,561 B2 | 4/2017 | Weinstein et al. | |
| 9,788,752 B2 | 10/2017 | Weinstein et al. | |
| 10,136,833 B2 | 11/2018 | Weinstein et al. | |
| 10,548,485 B2 | 2/2020 | Arditi et al. | |
| 10,561,336 B2 * | 2/2020 | Rappaport | A61B 5/05 |
| 10,588,599 B2 | 3/2020 | Weinstein et al. | |
| 10,660,609 B2 | 5/2020 | Weinstein et al. | |
| 10,680,324 B2 | 6/2020 | Weinstein et al. | |
| 2002/0032386 A1 | 3/2002 | Sackner et al. | |
| 2002/0045836 A1 | 4/2002 | Alkawwas | |
| 2002/0049394 A1 | 4/2002 | Roy et al. | |
| 2002/0050954 A1 | 5/2002 | Jeong-Kun et al. | |
| 2002/0147405 A1 | 10/2002 | Denker et al. | |
| 2002/0151816 A1 | 10/2002 | Rich et al. | |
| 2003/0036674 A1 | 2/2003 | Bouton | |
| 2003/0036713 A1 | 2/2003 | Bouton et al. | |
| 2003/0088180 A1 | 5/2003 | Van Veen et al. | |
| 2003/0100815 A1 | 5/2003 | Da Silva et al. | |
| 2003/0199770 A1 | 10/2003 | Chen et al. | |
| 2003/0219598 A1 | 11/2003 | Sakurai | |
| 2004/0015087 A1 | 1/2004 | Boric-Lubecke et al. | |
| 2004/0073081 A1 | 4/2004 | Schramm | |
| 2004/0077943 A1 | 4/2004 | Meaney et al. | |
| 2004/0077952 A1 | 4/2004 | Rafter et al. | |
| 2004/0249257 A1 | 12/2004 | Tupin et al. | |
| 2004/0254457 A1 | 12/2004 | van der Weide | |
| 2004/0261721 A1 | 12/2004 | Steger | |
| 2005/0038503 A1 | 2/2005 | Greenhalgh et al. | |
| 2005/0107693 A1 | 5/2005 | Fear et al. | |
| 2005/0192488 A1 | 9/2005 | Bryenton | |
| 2005/0245816 A1 | 11/2005 | Candidus et al. | |
| 2006/0004269 A9 | 1/2006 | Caduff et al. | |

(56) References Cited

U.S. PATENT DOCUMENTS

| | | |
|---|---|---|
| 2006/0009813 A1 | 1/2006 | Taylor et al. |
| 2006/0025661 A1 | 2/2006 | Sweeney et al. |
| 2006/0101917 A1 | 5/2006 | Merkel |
| 2006/0237223 A1 | 10/2006 | Chen et al. |
| 2006/0265034 A1 | 11/2006 | Aknine et al. |
| 2007/0016032 A1 | 1/2007 | Aknine |
| 2007/0016050 A1 | 1/2007 | Moehring et al. |
| 2007/0055123 A1 | 3/2007 | Takiguchi |
| 2007/0100385 A1 | 5/2007 | Rawat |
| 2007/0123770 A1 | 5/2007 | Bouton et al. |
| 2007/0123778 A1 | 5/2007 | Kantorovich |
| 2007/0135721 A1 | 6/2007 | Zdeblick |
| 2007/0152812 A1 | 7/2007 | Wong et al. |
| 2007/0156057 A1 | 7/2007 | Cho et al. |
| 2007/0162090 A1 | 7/2007 | Penner |
| 2007/0191733 A1 | 8/2007 | Gianchandani et al. |
| 2007/0263907 A1 | 11/2007 | McMakin et al. |
| 2008/0027313 A1 | 1/2008 | Shachar |
| 2008/0030284 A1 | 2/2008 | Tanaka et al. |
| 2008/0036668 A1 | 2/2008 | White et al. |
| 2008/0097199 A1 | 4/2008 | Mullen |
| 2008/0129511 A1 | 6/2008 | Yuen et al. |
| 2008/0139934 A1 | 6/2008 | McMorrow et al. |
| 2008/0167566 A1 | 7/2008 | Unver et al. |
| 2008/0169961 A1 | 7/2008 | Steinway et al. |
| 2008/0183247 A1 | 7/2008 | Harding |
| 2008/0200802 A1 | 8/2008 | Bahavaraju et al. |
| 2008/0224688 A1 | 9/2008 | Rubinsky et al. |
| 2008/0269589 A1 | 10/2008 | Thijs et al. |
| 2008/0283282 A1 | 11/2008 | Kawasaki et al. |
| 2008/0294036 A1 | 11/2008 | Hoi et al. |
| 2008/0316124 A1 | 12/2008 | Hook |
| 2008/0319301 A1 | 12/2008 | Busse |
| 2009/0021720 A1 | 1/2009 | Hecker |
| 2009/0048500 A1 | 2/2009 | Corn |
| 2009/0076350 A1 | 3/2009 | Bly et al. |
| 2009/0153412 A1 | 6/2009 | Chiang et al. |
| 2009/0153433 A1 | 6/2009 | Nagai et al. |
| 2009/0187109 A1 | 7/2009 | Hashimshony |
| 2009/0203972 A1 | 8/2009 | Heneghan et al. |
| 2009/0227882 A1 | 9/2009 | Foo |
| 2009/0240132 A1 | 9/2009 | Friedman |
| 2009/0240133 A1 | 9/2009 | Friedman |
| 2009/0248450 A1 | 10/2009 | Fernandez |
| 2009/0262028 A1 | 10/2009 | Mumbru et al. |
| 2009/0281412 A1 | 11/2009 | Boyden et al. |
| 2009/0299175 A1 | 12/2009 | Bernstein et al. |
| 2009/0312615 A1 | 12/2009 | Caduff et al. |
| 2009/0322636 A1 | 12/2009 | Brigham et al. |
| 2010/0004517 A1 | 1/2010 | Bryenton |
| 2010/0013318 A1 | 1/2010 | Iguchi et al. |
| 2010/0052992 A1 | 3/2010 | Okamura et al. |
| 2010/0056907 A1 | 3/2010 | Rappaport et al. |
| 2010/0076315 A1 | 3/2010 | Erkamp et al. |
| 2010/0081895 A1 | 4/2010 | Zand |
| 2010/0106223 A1 | 4/2010 | Grevious |
| 2010/0152600 A1 | 6/2010 | Droitcour et al. |
| 2010/0256462 A1 | 10/2010 | Rappaport et al. |
| 2010/0265159 A1 | 10/2010 | Ando et al. |
| 2010/0305460 A1 | 12/2010 | Pinter et al. |
| 2010/0312301 A1 | 12/2010 | Stahmann |
| 2010/0321253 A1 | 12/2010 | Ayala Vazquez et al. |
| 2010/0332173 A1 | 12/2010 | Watson et al. |
| 2011/0004076 A1 | 1/2011 | Janna et al. |
| 2011/0009754 A1 | 1/2011 | Wenzel et al. |
| 2011/0022325 A1 | 1/2011 | Craddock et al. |
| 2011/0040176 A1 | 2/2011 | Razansky et al. |
| 2011/0060215 A1 | 3/2011 | Tupin et al. |
| 2011/0068995 A1 | 3/2011 | Baliarda et al. |
| 2011/0125207 A1 | 5/2011 | Nabutovsky et al. |
| 2011/0130800 A1 | 6/2011 | Weinstein et al. |
| 2011/0257555 A1 | 10/2011 | Banet et al. |
| 2012/0029323 A1 | 2/2012 | Zhao |
| 2012/0065514 A1 | 3/2012 | Naghavi et al. |
| 2012/0068906 A1 | 3/2012 | Asher et al. |
| 2012/0098706 A1 | 4/2012 | Lin et al. |
| 2012/0104103 A1 | 5/2012 | Manzi |
| 2012/0330151 A1 | 12/2012 | Weinstein et al. |
| 2013/0041268 A1 | 2/2013 | Rimoldi et al. |
| 2013/0053671 A1 | 2/2013 | Farra |
| 2013/0069780 A1 | 3/2013 | Tran et al. |
| 2013/0090566 A1 | 4/2013 | Muhlsteff et al. |
| 2013/0123614 A1 | 5/2013 | Bernstein et al. |
| 2013/0184573 A1 | 7/2013 | Pahlevan et al. |
| 2013/0190646 A1 | 7/2013 | Weinstein et al. |
| 2013/0225989 A1 | 8/2013 | Saroka et al. |
| 2013/0231550 A1 | 9/2013 | Weinstein et al. |
| 2013/0297344 A1 | 11/2013 | Cosentino et al. |
| 2013/0310700 A1 | 11/2013 | Ward et al. |
| 2014/0046690 A1 | 2/2014 | Gunderson et al. |
| 2014/0081159 A1 | 3/2014 | Tao et al. |
| 2014/0128032 A1 | 5/2014 | Muthukumar |
| 2014/0163425 A1 | 6/2014 | Tran |
| 2014/0288436 A1 | 9/2014 | Venkatraman et al. |
| 2015/0025333 A1 | 1/2015 | Weinstein et al. |
| 2015/0150477 A1 | 6/2015 | Weinstein et al. |
| 2015/0164349 A1 | 6/2015 | Gopalakrishnan et al. |
| 2015/0335310 A1 | 11/2015 | Bernstein et al. |
| 2016/0073924 A1 | 3/2016 | Weinstein et al. |
| 2016/0095534 A1* | 4/2016 | Thakur ............ A61B 5/4842 600/547 |
| 2016/0198957 A1 | 7/2016 | Arditi et al. |
| 2016/0198976 A1 | 7/2016 | Weinstein et al. |
| 2016/0213321 A1 | 7/2016 | Weinstein et al. |
| 2016/0317054 A1 | 11/2016 | Weinstein et al. |
| 2016/0345845 A1 | 12/2016 | Ravid et al. |
| 2017/0035327 A1 | 2/2017 | Yuen et al. |
| 2017/0135598 A1 | 5/2017 | Weinstein et al. |
| 2017/0238966 A1 | 8/2017 | Weinstein et al. |
| 2017/0296093 A1 | 10/2017 | Weinstein et al. |
| 2019/0298208 A1 | 10/2019 | Weinstein et al. |
| 2020/0113447 A1 | 4/2020 | Arditi et al. |
| 2020/0297309 A1 | 9/2020 | Weinstein et al. |
| 2020/0381819 A1 | 12/2020 | Weinstein et al. |

FOREIGN PATENT DOCUMENTS

| | | |
|---|---|---|
| DE | 10008886 | 9/2001 |
| EP | 1834588 A1 | 9/2007 |
| EP | 2506917 A1 | 10/2012 |
| EP | 2 602 870 A1 | 6/2013 |
| JP | 10-137193 A | 5/1998 |
| JP | 2000-235006 A | 8/2000 |
| JP | 2001-525925 A | 12/2001 |
| JP | 2002-094321 | 3/2002 |
| JP | 2003-141466 | 5/2003 |
| JP | 2004-526488 A | 9/2004 |
| JP | 2006-208070 A | 8/2006 |
| JP | 2006-319767 A | 11/2006 |
| JP | 2007-061359 A | 3/2007 |
| JP | 2007-149959 | 6/2007 |
| JP | 2008-515548 A | 5/2008 |
| JP | 2008-148141 A | 6/2008 |
| JP | 2008-518706 A | 6/2008 |
| JP | 2008-530546 A | 7/2008 |
| JP | 2008-542759 A | 11/2008 |
| JP | 2008-545471 | 12/2008 |
| JP | 2009-514619 A | 4/2009 |
| JP | 2009-522034 A | 6/2009 |
| JP | 2010-507929 | 3/2010 |
| JP | 2010-072957 | 4/2010 |
| JP | 2010-512190 A | 4/2010 |
| JP | 2010-530769 | 9/2010 |
| JP | 2010-537766 A | 12/2010 |
| JP | 2011-507583 A | 3/2011 |
| JP | 2011-524213 A | 9/2011 |
| JP | 2012-090257 | 5/2012 |
| WO | WO 02/03499 A1 | 1/2002 |
| WO | WO 2003/009752 A2 | 2/2003 |
| WO | WO 2006/127719 A2 | 11/2006 |
| WO | WO 2006/130798 A2 | 12/2006 |
| WO | WO 2007/017861 A2 | 2/2007 |
| WO | WO 2007/023426 A2 | 3/2007 |
| WO | WO 2008/070856 A2 | 6/2008 |

(56) References Cited

FOREIGN PATENT DOCUMENTS

| WO | WO 2008/148040 A1 | 12/2008 |
|----|-------------------|---------|
| WO | WO 2009/031149 A2 | 3/2009 |
| WO | WO 2009/031150 A2 | 3/2009 |
| WO | WO 2009/060182 A1 | 5/2009 |
| WO | WO 2009/081331 A1 | 7/2009 |
| WO | WO 2009/152625 A1 | 12/2009 |
| WO | WO 2011/067623 A1 | 6/2011 |
| WO | WO 2011/067685 A1 | 6/2011 |
| WO | WO 2011/141915 A2 | 11/2011 |
| WO | WO 2012/011065 A1 | 1/2012 |
| WO | WO 2012/011066 A1 | 1/2012 |
| WO | WO 2013/118121 A1 | 8/2013 |
| WO | WO 2013/121290 A2 | 8/2013 |
| WO | WO 2015/118544 A1 | 8/2015 |

OTHER PUBLICATIONS

Ascension Technology Corporation, "TrakSTAR Adds Versatility to Ascension's New Product Line: Desktop Model Joins driveBAY Tracker for Fast Guidance of Miniaturized Sensor", USA, Apr. 7, 2008.

Bell et al., "A Low-Profile Achimedean Spiral Antenna Using an EBG Ground Plane", IEEE Antennas and Wireless Propagation Letters 3, pp. 223-226 (2004).

Beyer-Enke et al., Intra-arterial Doppler flowmetry in the superficial femoral artery following angioplasty., 2000, European Radiology, vol. 10, No. 4, p. 642-649.

Claron Technology Inc., "MicronTracker 3:A New Generation of Optical Trackers", Canada, 2009.

Czum et al., "The Vascular Diagnostic Laboratory", The Heart & Vascular Institute Newsletter, vol. 1, USA, Winter, 2001.

Extended Search Report for European Application No. 11809360.8, dated, Mar. 11, 2014.

Ghosh, et al., Immediate Evaluation of Angioplasty and Stenting Results in Supra-Aortic Arteries by Use of a Doppler-Tipped Guidewire, Aug. 2004, American Journal of Neuroradiology, vol. 25, p. 1172-1176.

Gentili et al., "A Versatile Microwave Plethysmograph for the Monitoring of Physiological Parameters", IEEE Transactions on Biomedical Engineering, IEEE Service Center, Pitscataway, NJ, US, vol. 49, No. 10, Oct. 1, 2002.

Haude et al., Intracoronary Doppler-and Quantitative Coronary Angiography-Derived Predictors of Major Adverse Cardiac Events After Stent Implantation, Mar. 6, 2001, Circulation, vol. 103(9), p. 1212-1217.

Immersion Corporation, "Immersion Introduces New 3D Digitizing Product-MicroScribe G2; Faster Data Transfer, USB Compatibility, New Industrial Design", Press Release, San Jose, USA, Jul. 1, 2002.

International Preliminary Report on Patentability, dated Jan. 31, 2013, for International Application No. PCT/IB2011/053246, 22 pages.

International Preliminary Report on Patentability, dated Aug. 19, 2014 for International Application No. PCT/IB2013/000663 filed Feb. 15, 2013.

International Preliminary Report on Patentability, dated Jun. 5, 2012, for International Application No. PCT/IB2010/054861.

International Preliminary Report on Patentability, dated Jan. 22, 2013, for International Application No. PCT/IB2011/053244, 6 pages.

International Preliminary Report on Patentability, dated Jun. 5, 2012, for International Application No. PCT/IB2009/055438.

International Search Report and Written Opinion of the International Searching Authority, dated Dec. 2, 2011, for International Application No. PCT/IB2011/053244, 7 pages.

International Search Report and Written Opinion, dated Dec. 13, 2011, for International Application No. PCT/IB2011/053246, 24 pages.

International Search Report and Written Opinion, dated Feb. 26, 2015, for International Application No. PCT/IL2014/050937.

International Search Report and Written Opinion, dated Jul. 20, 2010, for International Application No. PCT/IB2009/055438.

International Search Report and Written Opinion, dated Nov. 26, 2013 for International Application No. PCT/IB2013/000663 filed Feb. 15, 2013.

International Search Report, dated Apr. 5, 2011, for International Application No. PCT/IB2010/054861.

International Search Report and Written Opinion, dated Nov. 28, 2018 for International Application No. PCT/IL2018/050808 filed Jul. 20, 2018.

Kantarci et al., Follow-Up of Extracranial Vertebral Artery Stents with Doppler Sonography., Sep. 2006, American Journal of Roentgenology, vol. 187, p. 779-787.

Lal et al., "Duplex ultrasound velocity criteria for the stented carotid artery", Journal of Vascular Surgery, vol. 47, No. 1, pp. 63-73, Jan. 2008.

Larsson et al., "State Diagrams of the Heart—a New Approach to Describing Cardiac Mechanics", Cardiovascular Ultrasound 7:22 (2009).

Liang, Jing et al., Microstrip Patch Antennas on Tunable Electromagnetic Band-Gap Substrates, IEEE Transactions on Antennas and Propagation, vol. 57, No. 6, Jun. 2009.

Lin, J.C. et al., "Microwave Imaging of Cerebral Edema", Proceedings of the IEEE, IEEE, NY, US, vol. 70, No. 5; May 1, 1982, pp. 523-524.

Miura et al. "Time Domain Reflectometry: Measurement of Free Water in Normal Lung and Pulmonary Edema," American Journal of Physiology—Lung Physiology 276:1 (1999), pp. L207-L212.

Notice of Reasons for Rejection, dated Apr. 17, 2015, for JP 2013-520273.

Notice of Reasons for Rejection, dated Apr. 28, 2014, for JP 2012-541588.

Notice of Reasons for Rejection, dated Mar. 31, 2015, for JP 2012-541588.

Partial Supplementary Search Report, dated Oct. 19, 2015, for EP Application No. 13748671.8.

Paulson, Christine N., et al. "Ultra-wideband radar methods and techniques of medical sensing and imaging" Proceedings of SPIE, vol. 6007, Nov. 9, 2005, p. 60070L.

Pedersen, P.C., et al., "Microwave Reflection and Transmission Measurements for Pulmonary Diagnosis and Monitoring", IEEE Transactions on Biomedical Engineering, IEEE Service Center, Piscataway, NJ, US, vol. BME-19, No. 1, Jan. 1, 1978; pp. 40-48.

Polhemus, "Fastrak: The Fast and Easy Digital Tracker", USA, 2008.

Ringer et al., Follow-up of Stented Carotid Arteries by Doppler Ultrasound, Sep. 2002, Neurosurgery, vol. 51, No. 3, p. 639-643.

Supplementary European Search Report and European Search Opinion, dated Jun. 13, 2013, for European Application No. 09851811.1.

Supplementary European Search Report and European Search Opinion, dated Mar. 11, 2014, for European Application No. 11809359.1.

Supplementary European Search Report and Search Opinion, dated Dec. 4, 2014, for EP Application No. 10834292.4.

Supplementary European Search Report, dated Mar. 7, 2016, for EP Application No. 13748671.8.

Written Opinion for International Application No. PCT/IB2010/054861 dated Apr. 5, 2011.

Yang, F. et al. "Enhancement of Printed Dipole Antennas Characteristics Using Semi-EBG Ground Plane", Journal of Electromagnetic Waves and Application, U.S., Taylor & Francis, Apr. 3, 2006, vol. 8, pp. 993-1006.

Lin et al., "Enhanced performances of a compact conical pattern annular-ring patch antenna using a slotted ground plane," Microwave Conference, 2001. APMC 2001. 2001 Asia-Pacific Dec. 3-6, 201, IEEE, vol. 3, Dec. 3, 2001, pp. 1036-1039.

Lin et al: "Using dual-antenna nanosecond pulse near field sensing technology for non-contact and continuous blood pressure measurement", Engineering in Medicine and Biology Society (EMBC), 2013 35th Annual International Conference of the IEEE, IEEE, Aug. 28, 2012 (Aug. 28, 2012), pp. 219-222.

(56) References Cited

OTHER PUBLICATIONS

Matsugatani et al., "Surface Wave Distribution Over Electromagnetic Bandgap (EBG) and EBG Reflective Shield for Patch Antenna," IEICE Transactions on Electronics, vol. E88-C, No. 12, Dec. 1, 2005, pp. 2341-2349.

Solberg et al: "A feasibility study on aortic pressure estimation using UWB radar", Ultra-Wideband, 2009. ICUWB 2009. IEEE International Conference on, IEEE, Piscataway, NJ, USA, Sep. 9, 2009 (Sep. 9, 2009), pp. 464-468.

Yang et al., "Reflection phase characterizations of the EBG ground plane for low profile wire antenna applications," IEEE Transactions on Antennas and Propagation, vol. 51, No. 10, Oct. 1, 2003, pp. 2691-2703.

Zhang et al., "Planar artificial magnetic conductors and patch antennas," IEEE Transactions on Antennas and Propagation, vol. 51, No. 10, Oct. 1, 2003, pp. 2704-2712.

\* cited by examiner

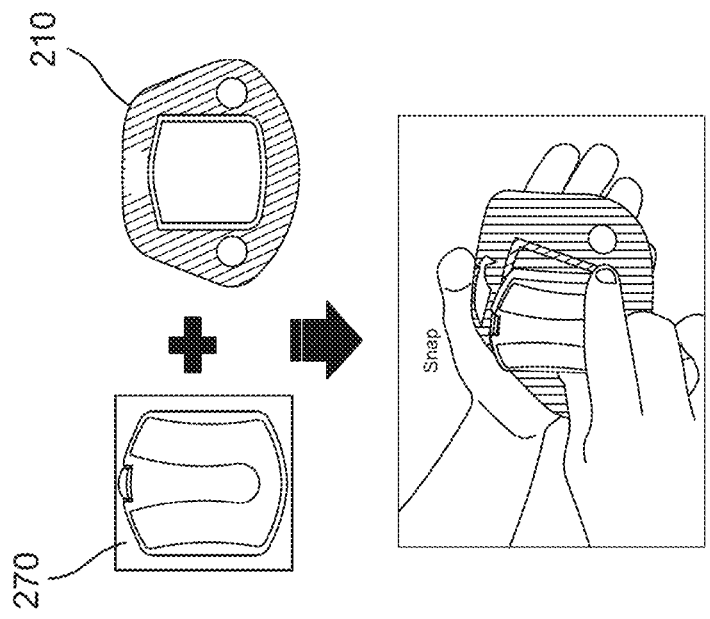
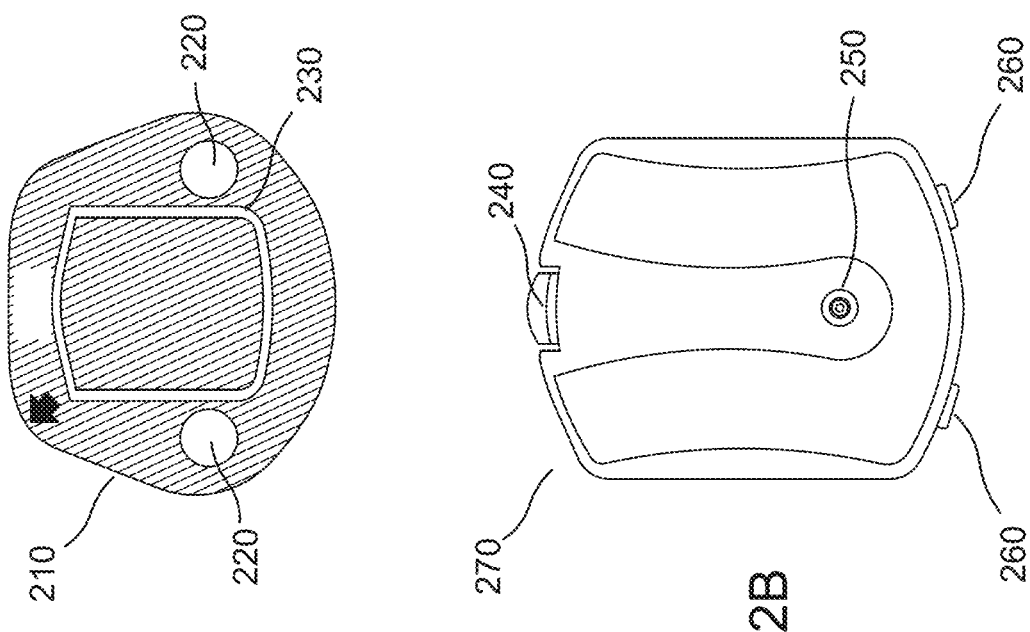
FIG. 2A  FIG. 2B  FIG. 2C

Patient Home_522 - 108 Pertinent Findings

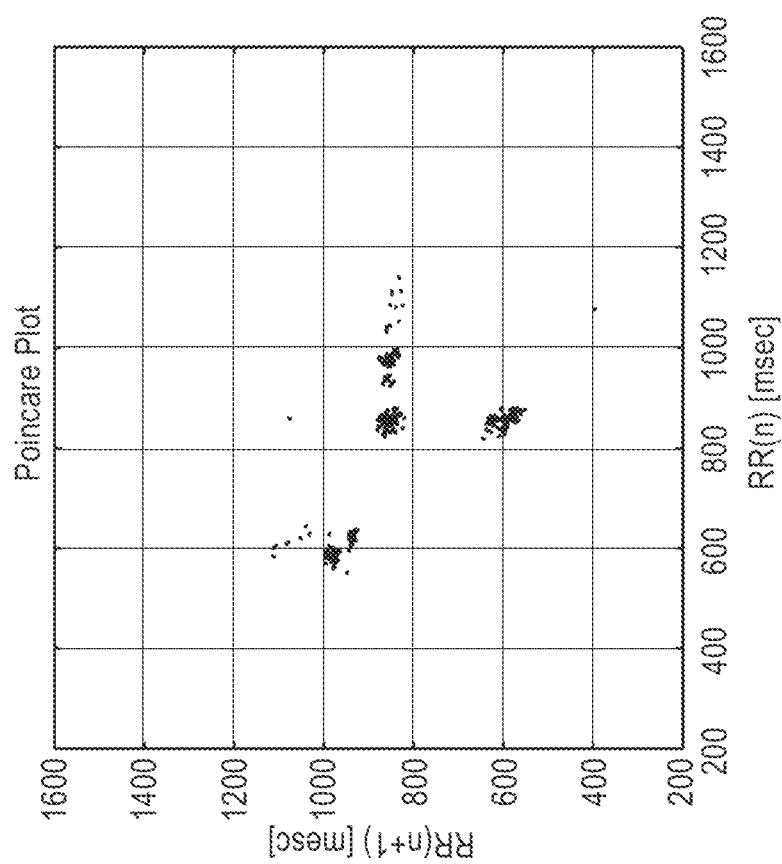

SYSTEMS, DEVICES AND METHODS FOR PHYSIOLOGICAL MONITORING OF PATIENTS

RELATED APPLICATIONS

This application claims benefit of and priority to U.S. provisional patent application No. 62/543,803, filed Aug. 10, 2017, the entire disclosure of which is incorporated herein by reference.

FIELD OF THE DISCLOSURE

Embodiments of the current disclosure are directed toward physiological monitoring of patients, and more particularly, systems, devices and methods for physiological monitoring of patients with a continuous transmission and analysis of monitored physiological data during the monitoring process.

BACKGROUND OF THE DISCLOSURE

There is a wide variety of electronic and mechanical devices for monitoring underlying patients' medical conditions. In some examples, depending on the underlying medical condition being monitored and/or treated, medical devices such as cardiac pacemakers or defibrillators may be surgically implanted or connected externally to the patient. Physicians may use such devices alone or in combination with drug therapies to treat or control patient medical conditions.

Such patients can include heart failure patients, e.g., congestive heart failure (CHF) is a condition in which the heart's function as a pump is inadequate to meet the body's needs. Generally, many disease processes can impair the pumping efficiency of the heart to cause congestive heart failure. The symptoms of congestive heart failure vary, but can include: fatigue, diminished exercise capacity, shortness of breath, and swelling (edema). The diagnosis of congestive heart failure is based on knowledge of the individual's medical history, a careful physical examination, and selected laboratory tests.

Patients in this group can suffer from cardiac arrhythmias. One of the most deadly cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia. External pacemakers, defibrillators and other medical monitors designed for ambulatory and/or long-term use have further improved the ability to timely detect and treat life-threatening conditions.

Heart failure patients can also benefit from having their thoracic fluid levels being monitored. Radio-frequency (RF) electromagnetic radiation has been used for diagnosis and imaging of body tissues. Diagnostic devices that include an antenna can be used to direct the RF electromagnetic waves into a body and generate signals responsively to the waves that are scattered from within the body. Such signals can be processed to determine various properties of body tissues located along the paths of the transmitted and/or scattered waves.

SUMMARY OF SOME OF THE EMBODIMENTS

Embodiments of the current disclosure include a physiological patient monitoring system comprising a plurality of physiological monitoring devices that are each configured for removable attachment to a corresponding plurality of patients, and a server in remote communication with the plurality of physiological monitoring devices. In some embodiments, each of the plurality of physiological monitoring devices is configured to continuously acquire physiological data from each of the corresponding plurality of patients. In some embodiments, the server may comprise a database; a memory implemented in non-transitory media and in communication with the database; and at least one processor in communication with the database and the memory. In some embodiments, the at least one processor is configured to implement computer-executable instructions encoded in the memory, the instructions causing the at least one processor to: receive the continuously acquired physiological data from the plurality of physiological monitoring devices; process the received continuously acquired physiological data from the plurality of physiological monitoring devices to detect a plurality of events that have occurred or are occurring concerning the corresponding plurality of patients; store event information relating to each of the plurality of events that have occurred or are occurring concerning the corresponding plurality of patients in the database; issue one or more notifications for each of the plurality of events within between about 1 to about 15 minutes from an onset of each of a respective event of the plurality of events; receive at least one other physiological data that is different from the continuously received physiological data from the plurality of physiological monitoring devices for the corresponding plurality of patients at a number of times during a 24 hour period; and provide an output based on analyzing the received at least one other physiological data different from the continuously received physiological data.

In some embodiments, the plurality of physiological monitoring devices further comprises accelerometers for tracking posture and movement data of the plurality of patients. In some embodiments, the continuously acquired physiological data comprises at least one of ECG data and accelerometer data and the at least one other physiological data that is different from the continuously received physiological data comprises RF-based measurement data. In some embodiments, the at least one processor can be configured to issue the one or more notifications where each of the plurality of events concerning the plurality of patients are occurring during a same time period. In some embodiments, each of the plurality of events occurring during a same time period may comprise each of the plurality of events having an onset occurring within between about 1 second to about 5 minutes of each other.

In some embodiments, the at least one processor may be configured to issue the one or more notifications for each of the plurality of events that are occurring during a same time period for between about 10 to about 100 patients. In some embodiments, the at least one processor may be configured to issue the one or more notifications for each of the plurality of events that are occurring during a same time period for between about 25 to about 200 patients. In at least some of the embodiments, the plurality of events may comprise atrial fibrillation events, flutter events, supraventricular tachycardia events, ventricular tachycardia events, pause events, asystole events, AV block events, ventricular fibrillation events, bigeminy events, trigeminy events, ventricular ectopic beats, bradycardia events, and tachycardia events.

In some embodiments, the at least one processor may be configured to process the RF-based measurement data and determine one or more thoracic fluid metrics for the corresponding plurality of patients. Further, in some embodiments, the at least one processor may be configured to analyze the accelerometer data of a selected one of the plurality of patients and determine whether the patient is in at least one of a supine, lying on a first side, lying on a second side, reclined, sitting up, and upright state when an RF-based measurement is being carried out on the patient. In some embodiments, the at least one processor may be configured to analyze the accelerometer data of a selected one of the plurality of patients and determine whether a movement of the patient is outside an acceptable threshold and if so causing the at least one processor to discard or ignore the RF-based measurement. In addition, in some embodiments, the at least one processor may be configured to analyze the accelerometer data of a selected one of the plurality of patients and determine whether a movement of the patient is outside an acceptable threshold and if so causing the at least one processor to instruct the physiological monitoring device to re-take the RF-based measurement.

Some embodiments of the current disclosure may include a physiological patient monitoring system, comprising: a physiological monitoring device comprising a housing disposed on a patch, the patch being configured for removable attachment to or proximate the skin of a patient, the housing including at least one memory; at least one antenna disposed on the housing and configured to transmit radio-frequency (RF) waves towards a targeted portion of an internal tissue of the patient and receive reflected RF waves from the internal tissue; RF circuitry in communication with the at least one memory and configured to perform an RF-based measurement of a thoracic fluid level of the patient during a predetermined time period; a pair of ECG electrodes and associated circuitry in communication with the at least one memory and configured to: continuously acquire ECG signals of a patient, and storing the sensed ECG signals as a plurality of continuously acquired ECG data segments of preconfigured durations in the at least one memory; at least one three-axis accelerometer and associated circuitry configured to monitor for at least one of patient posture and movement information; and transceiver circuitry.

In some embodiments, the RF circuitry may be configured to perform an RF-based measurement of a thoracic fluid level of the patient during a predetermined time period by directing the transmission of the RF waves towards the targeted portion of the internal tissue, and processing the reflected RF waves to determine and store a plurality of RF parameters related to the thoracic fluid level of the patient in the at least one memory. In some embodiments, the transceiver circuitry may be configured to receive and transmit patient information to a remote server by: controlling continuous transmission of the continuously acquired ECG signals of the patient to the remote server by transmitting each of the plurality of stored continuously acquired ECG data segments immediately after an ECG data segment of the continuously acquired ECG data segment is stored in the memory of the physiological monitoring device during the acquisition of the ECG signals of the patient, and controlling scheduled transmission of the plurality of RF parameters from the RF-based measurement during the predetermined time period. In some embodiments, the remote server may comprise at least one processor configured to execute computer-executable instructions encoded in a memory in communication with the at least one processor, the instructions causing the at least one processor to: receive the continuously transmitted continuously acquired ECG signals of the patient and monitor for a cardiac event based on analyzing the continuously acquired ECG signals, and receive and analyze the plurality of RF parameters to determine a thoracic fluid metric corresponding to the thoracic fluid level of the patient on establishing successful completion of at least one of patient posture and movement tests based on at least one of patient posture and movement information taken during the predetermined time period.

In some embodiments, the instructions additionally may cause the at least one processor to analyze the continuously acquired ECG signals and determine information relating to one or more of a heart rate, atrial fibrillation, flutter, supraventricular tachycardia, ventricular tachycardia, pause, AV block, ventricular fibrillation, bigeminy, trigemini, ventricular ectopic beats, bradycardia, and tachycardia; to issue a notification on detecting an arrhythmia condition as the cardiac event; to issue the notification concerning the cardiac event within about 1 to about 15 minutes from when the monitoring device detects the cardiac event; to issue the notification concerning the cardiac event within about 1 to about 15 minutes of receiving a first ECG data segment at the remote server containing information relating the cardiac event; to analyze the patient posture information and determine whether the patient is in at least one of a supine, lying on a first side, lying on a second side, reclined, sitting up, and upright state during the predetermined time period when the RF-based measurement is being carried out; and/or to determine and store a baseline RF-based measurement corresponding to a baseline thoracic fluid level of the patient. In some embodiments, the at least one processor may be configured to determine and store the thoracic fluid metric relative to the baseline thoracic fluid level of the patient.

In some embodiments, the physiological patient monitoring system may comprise at least one of a temperature sensor, conductance sensor, pressure sensor, a respiration sensor, and a light sensor. In some embodiments, the at least one processor of the system may be configured to receive data from the respiration sensor, and the instructions additionally cause the at least one processor to determine one or more metrics related to a respiration of the patient. In some embodiments, the transmitted RF waves can be in a range from 500 MHz to 5 GHz.

In some embodiments, the physiological patient monitoring system may further comprise a gateway configured to relay the patient information from the monitoring device to the remote server. In some embodiments, the gateway may be configured to buffer the patient information. In some embodiments, the system may further comprise a battery charger configured to charge a battery of the monitoring device.

In some embodiments, the patch may comprise a first side configured to removably affix to the skin of the patient, and a second side configured to removably receive the housing. In some embodiments, the first side of the patch includes an adhesive for removably affixing the patch to the skin of the user.

In some embodiments, the housing further comprises a display configured to at least present information on at least one of the operation, condition, and function of at least one of the circuitry and system. In some embodiments, the display may comprise a touch screen configured to receive user input. In some embodiments, the display may comprise an LED indicator.

Some embodiments of the current disclosure may include a physiological patient monitoring system, comprising: a physiological monitoring device comprising a housing disposed on a patch, the patch being configured for removable attachment to or proximate the skin of a patient, the housing including at least one memory; at least one antenna disposed on the housing and configured to transmit radio-frequency (RF) waves in a range from 500 MHz to 5 GHz towards a targeted portion of an internal tissue of the patient and receive reflected RF waves from the internal tissue; RF circuitry in communication with the at least one memory and configured to perform between 1 to 50 RF-based measurements of a thoracic fluid level of the patient over a 24 hour period; a pair of ECG electrodes and associated circuitry in communication with the at least one memory and configured to continuously acquired ECG signals of a patient and store the continuously acquired ECG signals in the at least one memory; at least one three-axis accelerometer and associated circuitry configured to monitor at least one of patient posture and movement information; and transceiver circuitry configured to receive and transmit patient information to a remote server by controlling transmission of the continuously acquired ECG signals and the plurality of RF parameters from the RF-based measurements.

In some embodiments, each RF-based measurement of the RF circuitry may occur during a preconfigured duration in which the RF circuitry is configured to: direct the RF waves towards the targeted portion of the internal tissue for the preconfigured duration, and process the reflected RF waves to determine and store a plurality of RF parameters related to the RF-based measurement in the at least one memory.

In some embodiments, the remote server may comprise at least one processor configured to execute computer-executable instructions encoded in a memory in communication with the at least one processor, the instructions causing the at least one processor to: receive the continuously transmitted continuously acquired ECG signals of the patient and monitor for a cardiac event based on analyzing the ECG signals, and receive and analyze the plurality of RF parameters to determine a thoracic fluid metric corresponding to the thoracic fluid level of the patient on establishing successful completion of at least one of patient posture and movement tests based on the at least one of patient posture and movement information taken during the predetermined time period.

Some embodiments of the current disclosure may include a physiological monitoring device, comprising: a patch comprising an adhesive for removably affixing the patch to the skin of the user; a housing configured to removably attach to the patch; at least one memory disposed within the housing; at least one antenna disposed on the housing and configured to transmit radio-frequency (RF) waves in a range from 500 MHz to 5 GHz. towards a targeted portion of an internal tissue of the patient and receive reflected RF waves from the internal tissue; RF circuitry in communication with the at least one memory and the at least one antenna and configured to perform between 1 to 50 RF-based measurements of a thoracic fluid level of the patient over a 24 hour period; a pair of ECG electrodes and associated circuitry in communication with the at least one memory and configured to: continuously acquired ECG signals of a patient, and storing the continuously acquired ECG signals as a plurality of continuously acquired ECG data segments of preconfigured durations in the at least one memory; at least one three-axis accelerometer and associated circuitry configured to monitor at least one of patient posture and movement information; and transceiver circuitry.

In some embodiments, each measurement of the RF circuitry may occur during a preconfigured duration in which the RF circuitry is configured to: direct the RF waves towards the targeted portion of the internal tissue for the preconfigured duration, and process the reflected RF waves to determine and store a plurality of RF parameters related to the RF-based measurement in the at least one memory. In some embodiments, the transceiver circuitry may be configured to receive and transmit patient information to a remote server by: controlling continuous transmission of the continuously acquired ECG signals of the patient to the remote server by transmitting each of the plurality of stored continuously acquired ECG data segments immediately after an ECG data segment of the continuously acquired ECG data segments is stored in the memory of the physiological monitoring device during the acquisition of the ECG signals of the patient; and controlling scheduled transmission of the plurality of RF parameters from the RF-based measurements to the remote server.

Some embodiments of the current disclosure may include a physiological patient monitoring method comprising the steps of directing the transmission of the RF waves towards the targeted portion of the internal tissue; processing the reflected RF waves to determine and store a plurality of RF parameters related to the thoracic fluid level of the patient in the at least one memory; continuously acquiring ECG signals of a patient via a pair of ECG electrodes; storing the continuously acquired ECG signals as a plurality of continuously acquired ECG data segments of preconfigured durations in the at least one memory; monitoring at least one of patient posture and movement information via a three-axis accelerometer and associated circuitry; and receiving and transmitting patient information to a remote server by: controlling continuous transmission of continuously acquired ECG signals of the patient to the remote server by transmitting each of the plurality of stored continuously acquired ECG data segments immediately after an ECG data segments of the plurality of continuously acquired ECG data segments is recorded and stored in the memory of the physiological monitoring device during the acquisition of the ECG signals of the patient, and controlling scheduled transmission of the plurality of RF parameters from the RF-based measurement during the predetermined time period.

In some embodiments, the remote server comprises at least one processor configured to execute computer-executable instructions encoded in a memory in communication with the at least one processor, the instructions causing the at least one processor to receive the continuously acquired ECG signals of the patient and monitor for a cardiac event based on analyzing the continuously acquired ECG signals, and receive and analyze the plurality of RF parameters to determine a thoracic fluid metric corresponding to the thoracic fluid level of the patient on establishing successful completion of at least one of patient posture and movement tests based on at least one of patient posture and movement information taken during the predetermined time period.

Some embodiments of the current disclosure may include a physiological patient monitoring system or method according to any one and/or another of the embodiments illustrated, described or disclosed herein.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 2A-E show an example sensor(s) disclosed herein, a patch configured to hold the sensor(s) in proximity to a body and attachment of a patch housing a sensor(s) onto skin of a patient, according to some embodiments.

FIGS. 12A-C show example visualization tools utilizing Poincare plots to detect and analyze sinus rhythm (FIG. 12A), atrial fibrillation episode (FIG. 12B) and trigeminy (FIG. 12C), according to some embodiments.

DETAILED DESCRIPTION OF SOME OF THE EMBODIMENTS

Figure 1:
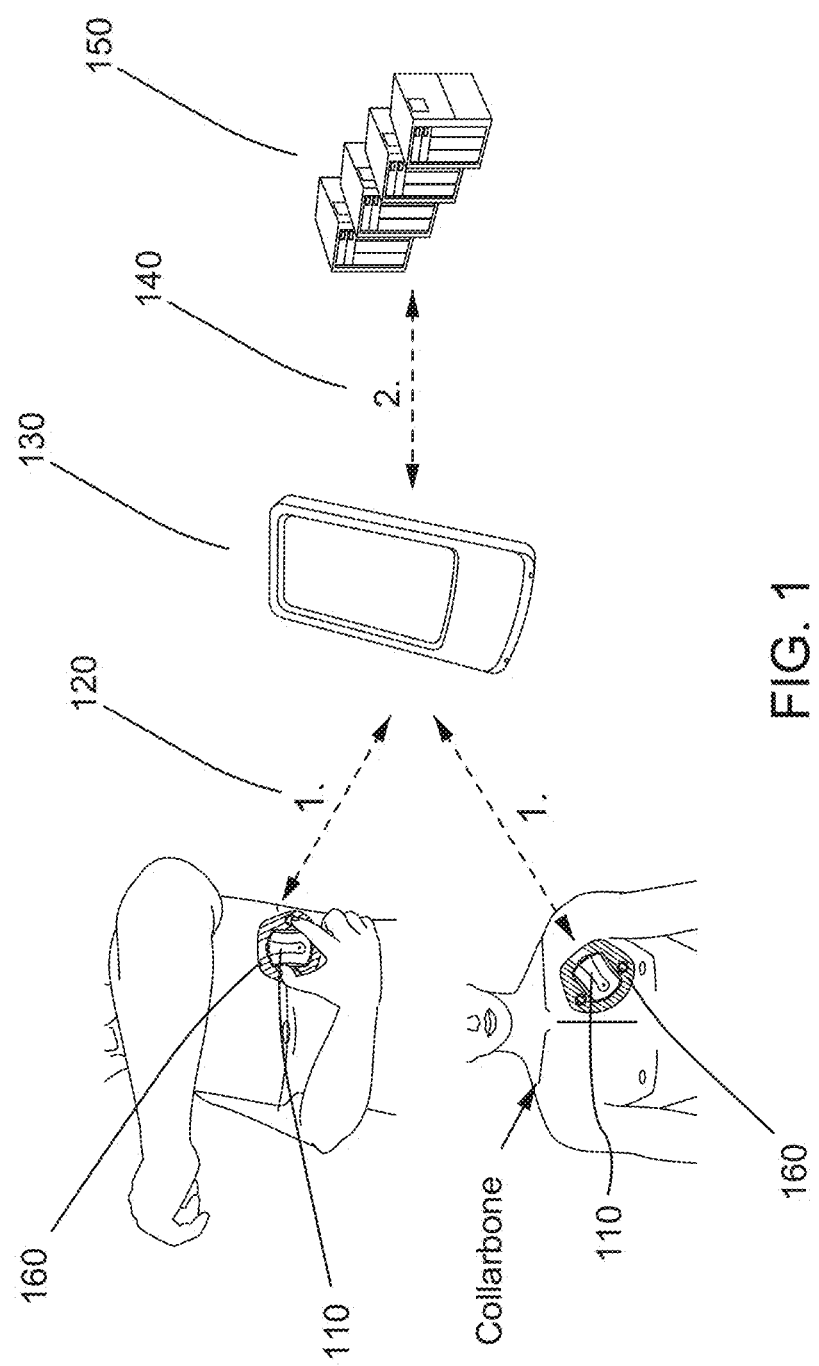
FIG. 1 shows an example schematic illustration of measurement and transmission of physiological data acquired via body-worn sensor(s) disclosed herein, according to some embodiments.

In some embodiments, the systems, devices and methods related to the wearable and/or wireless sensor(s) disclosed herein can be used to aid clinicians in the diagnosis and identification of various clinical conditions, events and/or trends. In various implementations described in detail below, the systems, devices, and methods aid in the continuous detection and monitoring of cardiac related conditions, such as, arrhythmias, and continuous and/or intermittent or periodic monitoring of tissue fluid levels such as thoracic fluid content (TFC) levels, including trends relating to these conditions. The arrhythmia and fluid monitoring system disclosed herein comprises a multi-sensor device that contains one or more of a radar transceiver for carrying out radio-frequency measurements relating to TFC levels of a patient, a tri-axis accelerometer, and an ECG monitor (e.g., single lead or multiple lead), and is configured to monitor various health parameters of the patient wearing the sensor(s) including lung/thoracic fluid content levels, heart rate, respiration rate, posture, activity level, arrhythmia events, and/or the like.

The wearable sensor(s) as described herein comprises ECG acquisition and processing circuitry that is physically housed within a same enclosure or unit as the radio-(RF) frequency based radar and associated circuitry. To overcome potential interferences between the two types of acquisition and processing circuits, in some embodiments, certain steps are taken. Such steps can include, for example, separation between of the grounds for the digital circuitry and the RF components, providing shielding for the RF radar components, using different power paths for the ECG processing and other digital circuitry from that of the RF radar components, and further, using filters in the digital circuits to minimize noise effects, implementing ECG filtering to minimize RF high frequency signals, and designing the circuit layout such that ECG signal paths are physically separated from the RF signal paths.

The system further comprises a patch for housing the sensor(s) and attaching the sensor(s) to surface of the patient. In addition, the system includes a wireless gateway (GW) for linking the sensor(s) to an external or outside server. The server is configured to analyze the continuously transmitted ECG data from the wearable device comprising the sensor(s), and includes, for example, databases, automated analysis algorithms, reporting tools and a web interface (e.g., touchscreen that facilitates interaction between the system and a user such as a patient or health care provider). Various electronic components of the arrhythmia and fluid monitoring sensor(s) including but not limited to the microcontroller, ECG leads (a pair, for example), ECG circuitry, accelerometer (three-axis), RF antenna integrated PCB, RF circuitry, power source (e.g., battery) may be enclosed within reusable, hermetically sealed slender housing made of plastic material (such as a cartridge).

For example, FIG. 1 shows an arrhythmia and fluid monitoring system that includes a physiological monitoring device 110, hereinafter referred to as "sensor(s)", and a wearable patch 160 configured to place the sensor(s) on, or in the vicinity of, a surface of a body (e.g., a patient). Further, the system may include a portable data transmission device (gateway) 130 that is capable of continuously transmitting data acquired by the sensor(s) 110 to one or more servers 150 for processing and/or analysis. Thus, for example, the gateway device 130 may transmit to the server 150 data received from the sensor(s) 110 with little or no delay or latency. To this end, in the context of data transmission between the device(s) 110 and server(s) 150, "continuously" for the present disclosure includes continuous (without interruption), or near continuous, i.e., within one minute after completion of a measurement by and/or an occurrence of an event on the device. Continuity may also be achieved by repetitive successive bursts of transmission, e.g., high-speed transmission. Similarly, the term "immediate," according to the present disclosure, includes as occurring or done at once, or near immediate i.e., within one minute after the completion of a measurement by and/or an occurrence of an event occurring on the device.

Further, in the context of physiological data acquisition by the device(s) 110, "continuously" also includes uninterrupted collection of sensor data, such as ECG data and/or accelerometer data, with clinical continuity. In this case, short interruptions in data acquisition of up to 1-second several times an hour or longer interruptions of a few minutes several times a day may be tolerated and can still be seen as "continuous". As to latency as a result of such a continuous scheme as described herein, this relates to the overall budget of response time which can amount to between about 5 to about 15 minutes overall response time (e.g., time from when an event onset is detected to when a notification regarding the event is issued). As such, transmission/acquisition latency would therefore be in the order of minutes.

Further, the wearable devices described herein are configured for long-term and/or extended use or wear by, or attachment or connection to a patient. For example, devices as described herein may be capable of being used or worn by, or attached or connected to a patient, without substantial interruption, for example, up to 24 hours or beyond (e.g., weeks, months, or even years). In some implementations, such devices may be removed for a period of time before use, wear, attachment, or connection to the patient is resumed, e.g., to change batteries, carry out technical service, update the device software or firmware, and/or to take a shower or engage in other activities, without departing from the scope of the examples described herein.

In some embodiments, the transmission of data/signals 120 between the sensor(s) 110 and the gateway device 130 may be a one way (e.g., from the sensor(s) 110 to the gateway device 130) or the transmission may be bi-directional. Similarly, the transmission of data/signals 140 between the gateway device 130 and the server 150 may be one way (e.g., from the gateway device 130 to the server 150) or bi-directional. The system may also include a charger (not shown) for powering the electronics of the system.

In some embodiments, the sensor(s) 110 is configured to monitor, record and transmit to the gateway device 130 physiological data about the wearer of the sensor(s) 110 continuously. In particular, the sensor(s) 110 may not interrupt monitoring and/or recording additional data while transmitting already acquired data to the gateway device 130. Put another way, in some embodiments, both the monitoring/recording and the transmission processes occur at the same time or at least nearly at the same time.

As an another example, if the sensor(s) 110 does suspend monitoring and/or recording additional data while it is transmitting already acquired data to the gateway device 130, the sensor(s) 110 may then resume monitoring and/or recording additional data prior to all the already acquired data being transmitted to the gateway device 130. In other words, the interruption period for monitoring and/or recording may be less in comparison to the time it takes to transmit the already acquired data (e.g., between about 0% to about 80%, about 0% to about 60%, about 0% to about 40%, about 0% to about 20%, about 0% to about 10%, about 0% to about 5%, including values and subranges therebetween), facilitating the near-continuous monitoring and/or recording of additional data during transmission of already acquired physiological data. For example in one specific scenario, when a measurement time duration is around 2 minutes, any period of suspension or interruption in the monitoring and/or recording of subsequent measurement data may range from a just few milliseconds to about a minute. Example reasons for such suspension or interruption of data may include allowing for the completion of certain data integrity and/or other on-line tests of previously acquired data as described in further detail below. If the previous measurement data has problems, the sensor(s) 110 can notify the patient and/or remote technician of the problems so that appropriate adjustments can be made.

In some embodiments, the bandwidth of the link 120 between the sensor 110 and the gateway device 130 may be larger, and in some instances significantly larger, than the bandwidth of the acquired data to be transmitted via the link 120 (e.g., burst transmission). Such embodiments ameliorate issues that may arise during link interruptions, periods of reduced/absent reception, etc. In some embodiments, when transmission is resumed after interruption, the resumption may be in the form of last-in-first-out (LIFO). The gateway device 130 can be configured to operate in a store and forward mode where the data received from the sensor 110 is first stored in an onboard memory of the gateway device and then forwarded to the external server. For example, such a mode can be useful where the link with the server may be temporarily unavailable. In some embodiments, the gateway device 130 can function as a pipe line and pass through data from the sensor 110 immediately to the server. In further examples, the data from the sensor may be compressed using data compression techniques to reduce memory requirements as well as transmission times and power consumptions.

In some embodiments, the sensor(s) 110 may be configured to monitor, record and transmit some data in a continuous or near-continuous manner as discussed above, while monitoring, recording and transmitting some other data in a non-continuous manner (e.g., periodically, no-periodically, etc.). For example, the sensor(s) 110 may be configured to record and transmit electrocardiogram (ECG) data continuously or nearly continuously while radio-frequency (RF) based measurements and/or transmissions may be periodic. For example, ECG data may be transmitted to the gateway device 130 (and subsequently the server 150) continuously or near-continuously as additional ECG data is being recorded, while RF-based measurements may be transmitted once the measuring process is completed.

Monitoring and/or recording of physiological data by the sensor(s) 110 may be periodic, and in some embodiments, may be accomplished as scheduled (i.e., periodically) without delay or latency during the transmission of already acquired data to the gateway device 130. For example, the sensor(s) 110 may acquire physiological data from the patient (i.e., the wearer of the sensor(s) 110) in a periodic manner and transmit the data to the gateway device 130 in a continuous manner as described above.

The sensor(s) 110 may be configured to transmit the acquired data to the servers 150 instead of, or in addition to, transmitting the data to the gateway device 130. The sensor (s) 110 may also be configured to store some or all of the acquired physiological data. In some embodiments, the transmission of data from the sensor(s) 110 to the gateway device 130 may be accomplished wirelessly (e.g., Bluetooth®, etc.) and/or via a wired connection, e.g., 120. The transmission of data from the gateway device 130 to the server 150 may also be accomplished wirelessly (e.g., Bluetooth®-to-TCP/IP access point communication, Wi-Fi®, cellular, etc.) and/or via a wired connection, e.g., 140.

As mentioned above, in some embodiments, the transmission of data and/or signals occurs via two links 120, 140, the links between the sensor(s) 110 and the gateway device 130 (e.g., Bluetooth® link) and between the gateway device 130 and the server 150 (e.g., Wifi®, cellular). The Bluetooth® link can be a connection bus for sensor(s) 110 and server 150 communication, used for passing commands, information on status of the microprocessor of the sensor(s) 110, measurement data, etc. In some embodiments, the microprocessor of the sensor(s) 110 may initiate communication with the server 150 (and/or the gateway device 130), and once connection is established, the server 150 may be configured to initiate some or all other communications. In some embodiments, the gateway device 130 may be configured to conserve the power available to the sensor(s) 110, device 130 and/or servers 150. For example, one or both links 120, 140 may enter power saving mode (e.g., sleep mode, off-state, etc.) when the connections between the respective devices/server are not available. As another example, the transmission of data may also be at least temporarily interrupted when the link quality (e.g., available bandwidth) is insufficient for at least a satisfactory transmission of the data. In such embodiments, the gateway device 130 may serve as a master device in its relationship to one or both of the sensor(s) 110 and the server 150.

In some embodiments, the gateway device 130 may be considered as a simple pipe, the sensor-gateway device-server path may be defined as a single link, i.e., the link performance may depend on the bottleneck between the sensor-gateway device and gateway device-server links. In some embodiments, at least the main bottleneck may be the gateway device-server link, since the gateway device is carried by the patient in close proximity to the device, while the gateway device-server link (e.g., cellular or WiFi® coverage) is expected to be variable. In some embodiments, a "best effort delivery" quality-of-service may be sufficient for the Bluetooth link and/or the TCP/IP link, since the transmitted data is processed (with some latency, for example) and is used for displaying notifications (for example, instead of being presented online to a monitoring center). In some embodiments, a single gateway device 130 may be configured to serve a plurality of sensors, i.e., the plurality of sensors may be connected to a single gateway device 130 via respective links. In some embodiments, there may be a plurality of gateway devices serving one or more sensor(s), i.e., each sensor of one or more sensors may be connected to a plurality of gateway devices via respective links.

In some embodiments, the transmission links 120, 140 may be configured to withstand co-existence interference from similar devices in the vicinity and from other devices using the same RF band (e.g., Bluetooth®, Cellular, WiFi®). Standard Bluetooth® protocol and/or standard TCP/IP protocols, as well as the addition of cyclic redundancy check to the transmitted data may be used to address any issue of interference. Further, to preserve the security of wireless signals and data, in some embodiments, data transfer between the sensor and the server may be done using a proprietary protocol. For example, TCP/IP link may use SSL protocol to maintain security, and the Bluetooth® link may be encrypted. As another example, UDP/HTTP may also be used for secure transmission of data. In some embodiments, only raw binary data may be sent, without any patient identification.

Examples of the types of physiological data that the arrhythmia and fluid monitoring sensor(s) 110 is configured to monitor and/or acquire from a patient wearing the sensor (s) 110 include one or more of electrocardiogram (ECG) data, thoracic impedance, heart rate, respiration rate, physical activity (e.g., movement) and patient posture. In some embodiments, the physiological data may be acquired and/or transmitted to the gateway device 130 or the server 150 by the sensor(s) 110 in a manner that is continuous, periodic or as instructed by received signals (e.g., as instructed by signal received from the gateway device 130 and/or the server 150). For example, the wearer of the sensor or another party (e.g., a health professional) may activate the sensor(s) 110 and the sensor may start monitoring and/or recording any one of the above-noted physiological parameters automatically without further input from the wearer or the party. The sensor(s) 110, or the arrhythmia and fluid monitoring system in general, may request further input (e.g., selection of a setting identifying the physiological parameter to be measured) before initiating the monitoring and/or recording of physiological data. In any case, once the monitoring and/or recording starts, the sensor(s) 110 may transmit the acquired data to the gateway device 130 and/or the server 150 in an at least a continuous manner as described above, for example.

In some embodiments, one or more of the above-noted physiological parameters may be measured periodically, and the sensor(s) 110 may transmit the measurements to the gateway device 130 in an at least a continuous manner as acquired. For example, the periodic measurements may proceed as scheduled and the transmission to the gateway device 130 may occur with little or no delay or latency after data is acquired.

In some embodiments, the sensor(s) 110, or the arrhythmia and fluid monitoring system in general, may be configured to operate some, but not all, of the available features discussed above. For example, the sensors 110 may be configured to monitor and/or acquire one or more of ECG data, thoracic impedance, heart rate, respiration rate, physical activity (e.g., movement), patient posture, etc., but not the others. For instance, the sensors may be configured to monitor and/or acquire data such as ECG data, but not respiration rate, physical activity (e.g., movement), patient posture. Such embodiments may be effected, for example, by including controls in the sensors and/or the system that separately control components of the sensors/system responsible for the features. For example, the arrhythmia and fluid monitoring system may include controls (e.g., power buttons) that separately control the accelerometer and the ECG components of the sensor. By switching on the accelerometer power control and switching off the ECG power control, in some embodiments, one may allow the monitoring and/or acquiring of data related to respiration rate, physical activity, and patient posture while deactivating the monitoring and/or acquiring of ECG data.

In some embodiments, an adhesive patch 160 may be used to attach the sensor(s) 110 to a surface of the body of a patient. FIGS. 2A-E show the sensor 270 disclosed herein, a patch 210 configured to attach the sensor 270 to a patient's body or at least hold the sensor 270 in proximity to skin of the body, and an illustration of a method of attaching the sensor 270 to the patch 210, according to some embodiments. The patch 210 may include a patch frame 230 (e.g., plastic frame) delineating the boundary of the region of the patch 210 that is configured for housing the sensor 270. The patch 210 may be disposable (e.g., single- or few-use patches), and may be made of biocompatible, non-woven material. In some embodiments, the sensor 270 may be designed for long-term usage. In such embodiments, the connection between the patch 210 and the sensor 270 may be configured to be reversible, i.e., the sensor 270 may be configured to be removably attached to the patch 210. For example, the sensor 270 may include components such as snap-in clips 240 that are configured to secure the sensor 270 to the patch 210 (e.g., the patch frame 230) upon attachment (and released the sensor 270 from the patch when separation is desired). The sensor 270 may also include positioning tabs 260 that facilitate the attachment process between the sensor 270 and the patch 210. In some embodiments, the patch may be designed to maintain attachment to skin of a patient for several days (e.g., in the range from about 4 days to about 10 days, from about 5 days to about 7 days, etc.).

In some embodiments, the patch 210 may include additional components that facilitate or aid with the monitoring and/or recording or acquiring of physiological data by the sensor 270. For example, the patch may include conductive elements such as one or more ECG electrodes 220 (e.g., a single lead, two leads, etc.) that can be used when recording ECG data from the surface (e.g., skin contacted directly or through a covering) of a patient's body. The electrodes may be coupled to the sensor 270 by dedicated wiring within the patch. In some embodiments, the ECG may have a sampling rate in then range from about 250 Hz to about 500 Hz, from about 300 Hz to about 450 Hz, from about 350 Hz to about 400 Hz, including values and subranges therebetween. In some embodiments, the ECG signal may be sampled after band-pass filtering by a 12 bit ADC. During normal operation, data may be transferred to the server "as-is" and can then be used by the server algorithms for analysis. In some embodiments, an internal algorithm allows for real-time evaluation of the ECG signal quality upon each attachment of the device to the patient ("attachment test").

Figure 2E:
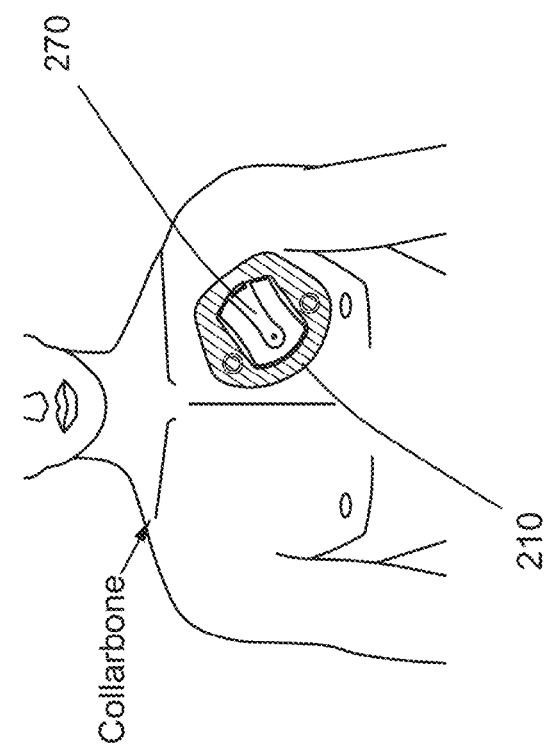
Figure 2D:
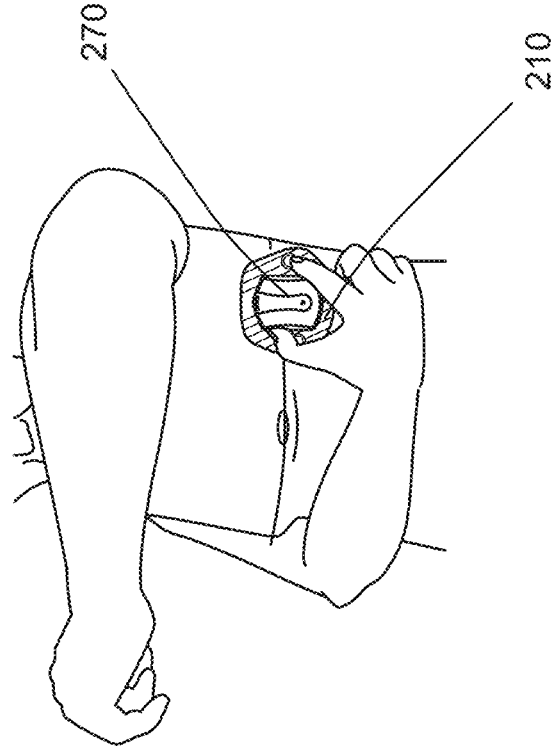

Examples of locations on surface of a patient body at which a patch may be placed are shown in FIGS. 2D-E, where a patch 320 housing sensor 310 is shown as placed at on the side (below armpit, for example) (FIG. 2D) and upper chest (FIG. 2E) of the torso of a patient. It is to be noted that the patch may be placed on any part of the surface of a patient's body that allows for efficient monitoring and recording of a physiological data (e.g., area of skin that allows for uniform attachment of the patch 320 to the skin). For example, one may place the patch 320 under an armpit at the nipple level for performing lung fluid level measurements. With respect to ECG measurements, the ECG signal at this location may be represented as the difference between standard V5 and V6 leads of an ECG.

Figure 3B:
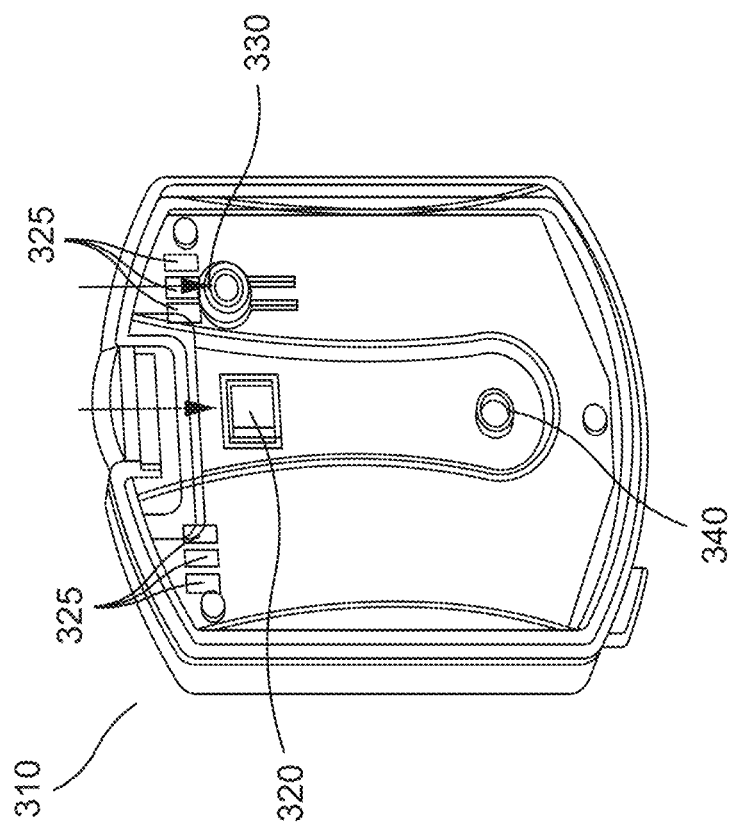
FIGS. 3A-C show example front, back and exploded views, respectively, of the sensor(s) disclosed herein, according to some embodiments.
Figure 3A:
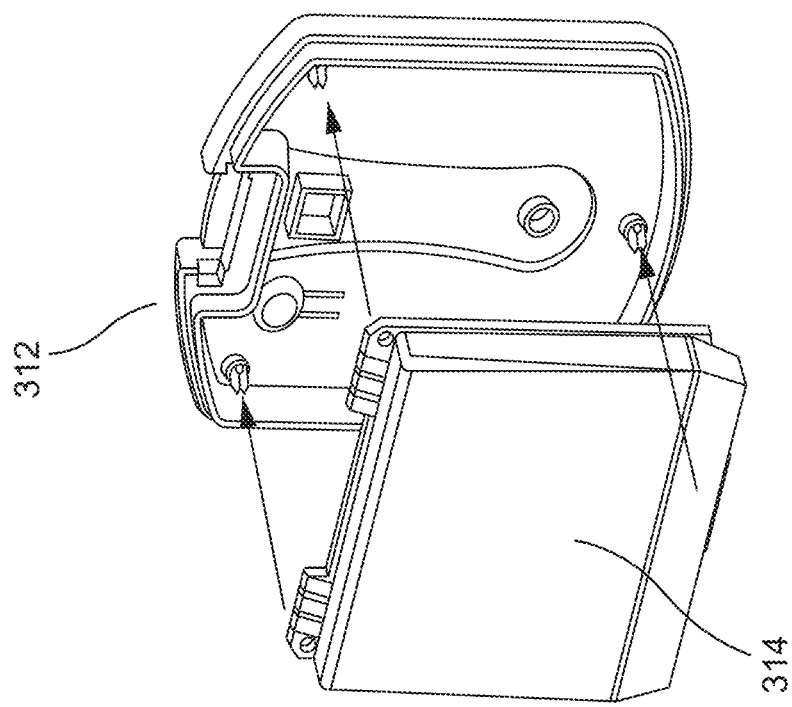
Figure 3C:
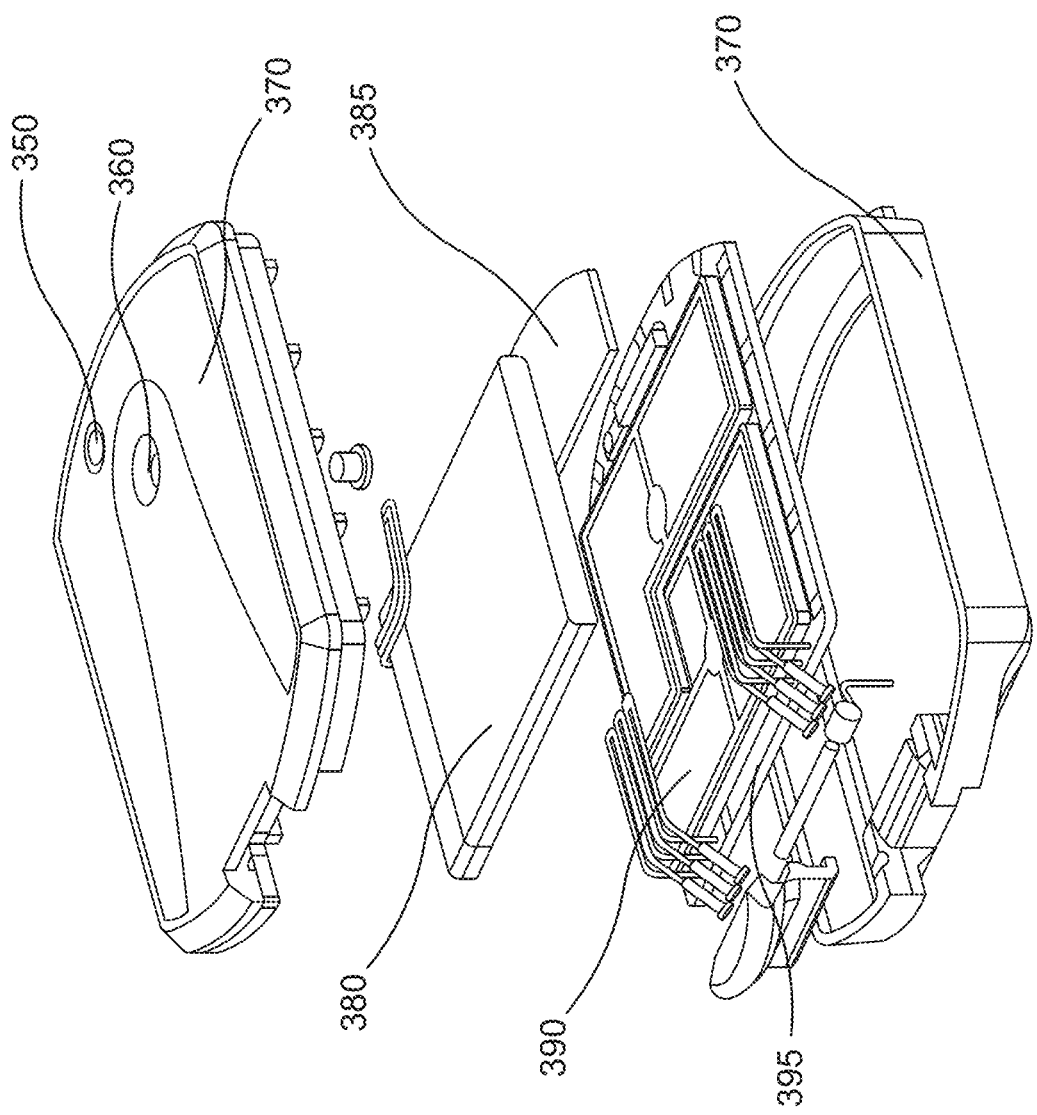

With reference to FIGS. 3A-C, in some embodiments, front, back and exploded views, respectively, of the sensor (s) disclosed herein are shown. FIG. 3A shows the front 312 and back 314 covers of the sensor 310 (labelled as top and bottom covers 370 in FIG. 3C). In some embodiments, such covers may couple to each other to seal the electrical components of the sensor from the surrounding environment (e.g., electrical sealing). In such embodiments, metallic tabs 325 may protrude outside the covers to provide electrical connection for situations such as performing ECG measurements, charging power source and/or the like.

FIG. 3B shows that the sensor 310 may include one or more indicators that identify the status of the sensor 310 to the user of the sensor 310. Examples of such indicators include but are not limited to light indicator 340 (e.g., a light emitting diode (LED) indicator) and sound indicators 320. In some embodiments, the indicators 320, 340 provide feedback on the status of the sensor 310 and components thereof, such as the charging and/or power level of the power source of the sensor 310 (e.g., a battery), the attachment level of the sensor 310 to the patch 210, the attachment level of the patch 210 to the surface of the body to which the patch 210 is attached, etc. As another example, the sensor may respond by blinking (e.g., via the light indicator 340) or buzzing (e.g., via the sound indicator 320) in response to an engagement by a patient to indicate possible symptoms.

In some embodiments, FIG. 3C provides an exploded view of the sensor 310 depicting at least some of the components of the sensor. For example, the sensor 310 may comprise a power source such as a battery 380, a light indicator 360, a button 350 for facilitating the interaction of a patient, a healthcare provider, and/or a technician with the sensor, a wireless communications circuit 385, a radio frequency shield 390 (such as a metallic cover, e.g., to prevent interferences with the ECG processing and other digital circuitry), a digital circuitry board 395, and/or the like. FIG. 3C shows a Bluetooth unit as an example of a wireless communications circuit 385, although in addition to or alternatively to the Bluetooth unit, other modules facilitating other types of communications (examples of which including WiFi®, cellular, etc.) may be included in the sensor 310.

In some embodiments, the sensor 310 may also include input interfaces such as buttons for interfacing with a user. For example, the sensor may include a button 330 that allows a patient or a health care professional to activate or deactivate the sensor 310. Such input interfaces may be configured to avoid or at least minimize unintended interactions with a user. For example, a button may be sized and shaped to avoid accidental activation (e.g., the button may be configured to require activation by being pushed in with an external object). This button may be used to reset the sensor as well as pair the sensor to the gateway device and initiate communication. In some embodiments, the input interface of the sensor may include a touch screen configured to receive input from a user and/or provide information back to the user. For example, the input may allow the user to set the sensor in an "airplane mode," i.e., for example by deactivating any wireless communication (e.g., Wi-Fi, Bluetooth, etc.) with external devices and/or servers. For example, the button can be implemented as a magnetic switch, e.g., an embedded magnetic switch, instead of a physical button. Such an implementation can be useful for designing the housing of the device and avoid exposing button components to the environment.

Figure 4A:
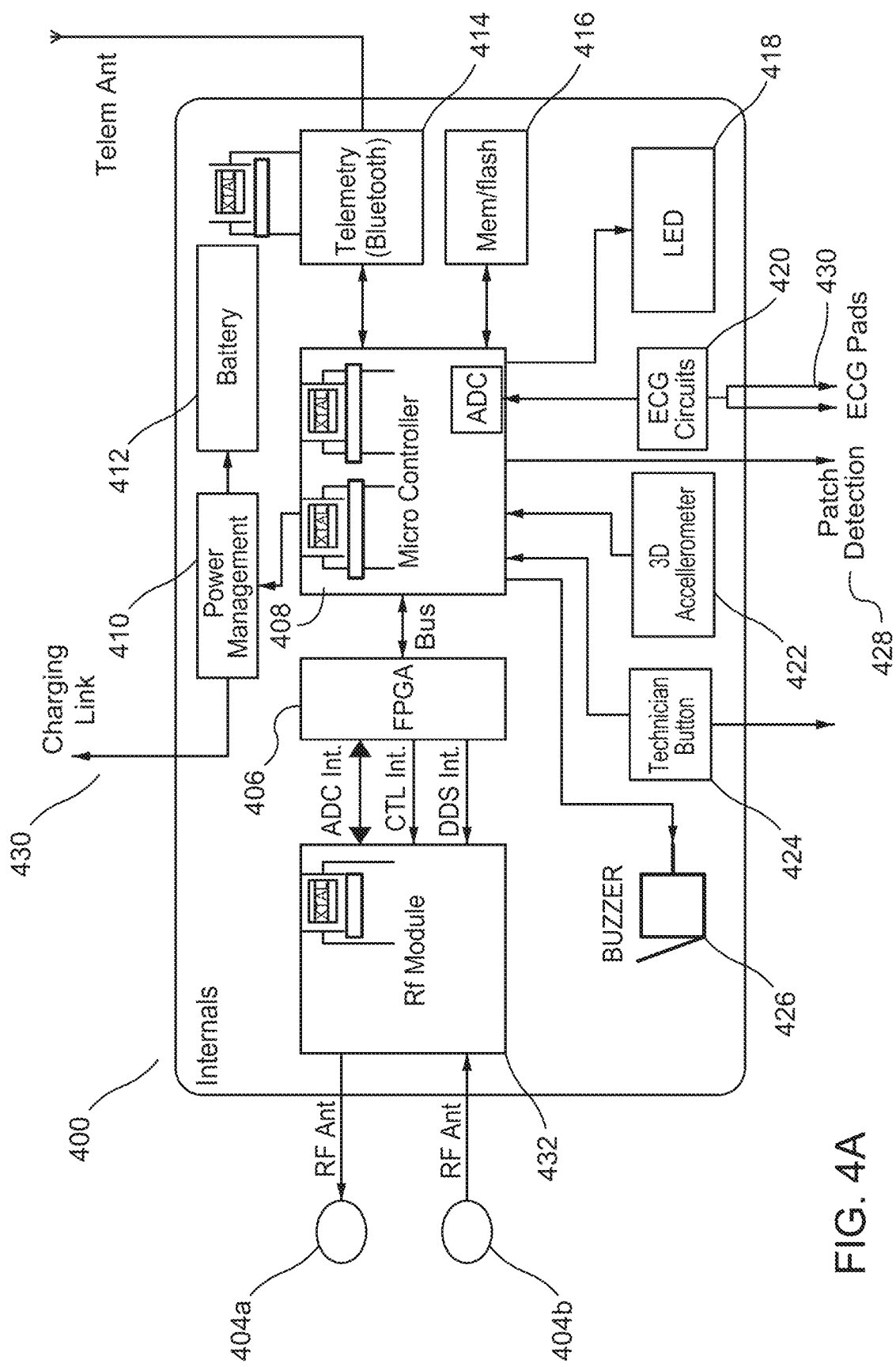
FIG. 4A shows an example illustration of device electronics architecture for measurements and transmission of patient physiological data, according to some embodiments.

In some embodiments, as described above, the disclosed sensor is configured to monitor and/or acquire data on physiological parameters including but not limited to electrocardiogram (ECG) data, thoracic impedance, heart rate, respiration rate, physical activity, posture and/or the like. To that effect, the sensor and/or the patch housing the sensor may include components that facilitate or undertake the monitoring and/or recording of at least some of these parameters. For example, as noted above, the patch housing the sensor may include ECG electrodes coupled to the sensors to facilitate the monitoring and/or acquiring of ECG data. As shown in FIG. 4A, which shows an example embodiment of device electronics architecture for measurements and transmission of patient physiological data, the sensor includes EGG processing circuitry configured to couple to the ECG electrodes embedded in the patch housing the sensor itself. The ECG processing circuitry is configured to, for example, perform filtering, amplification, and/or removal of noise, low frequency variations in the signal, and other signal artifacts.

As another example, the sensor may include radio frequency (RF) antenna for directing electromagnetic waves into a body of a patient and receiving waves that are scattered and/or reflected from internal tissues. Further, the sensor may include RF circuitry or module configured to process the received waves so as to determine some properties of the tissues that are on the path of the transmitted and/or scattered/reflected waves. For example, the antenna may direct RF waves towards a lung of a patient and the RF circuitry may analyze the scattered/reflected waves to perform an RF-based measurement of the lung fluid level of the patient. FIG. 4A shows an example embodiment of a sensor comprising RF antennas, an RF module and circuits for controlling the module (e.g., field-programmable gate array (FPGA) circuits).

With reference to FIG. 4A, in some embodiments, the sensor 400 includes external interfaces such as but not limited to RF antennas (e.g., bi-static) 404a, 404b for transmitting & receiving RF signals, a button or switch 424 for activating or deactivating the sensor 400, an LED 418 and a buzzer 426 for providing light and audio feedback to a user of the sensor 400, a battery charging link 430 coupled to a power management module 410 for charging an onboard power source such as a battery 412, and ECG pads 430 for recording synchronization signal. In some embodiments, the sensor 400 may also include a wireless link (e.g., Bluetooth®) (not shown) to provide an external server access to the sensor 400 so as to exert at least some control on the sensor 400.

Internally, in some embodiments, the sensor 400 may include a microprocessor 408 (which may be alternatively referred to as a micro-controller) that includes instructions thereon specifying how measurements (RF, ECG, accelerometer, etc.) are taken and the obtained data are transmitted, how to relay the status of the sensor 400, how/when the sensor 400 can enter the plurality of sleep levels, and/or the like. In some embodiments, the instructions may also specify the conditions for performing certain types of measurements. For example, the instructions may specify that the accelerometer may not commence measurements (for physical activity, and patient posture, for example) unless the user of the sensor is at rest or maintaining a certain posture. As another example, the instructions may identify the conditions that may have to be fulfilled before ECG measurements can commence, such conditions including at least sufficient attachment level between the sensor and the surface on the body to which the sensor 400 is attached. In some embodiments, the microprocessor 408 may have internal and external non-volatile memory banks that can be used for keeping measurement directory and data, scheduler information, and/or a log of actions and errors. This non-volatile memory allows saving power via a total power-down while retaining data and status information.

Figure 4B:
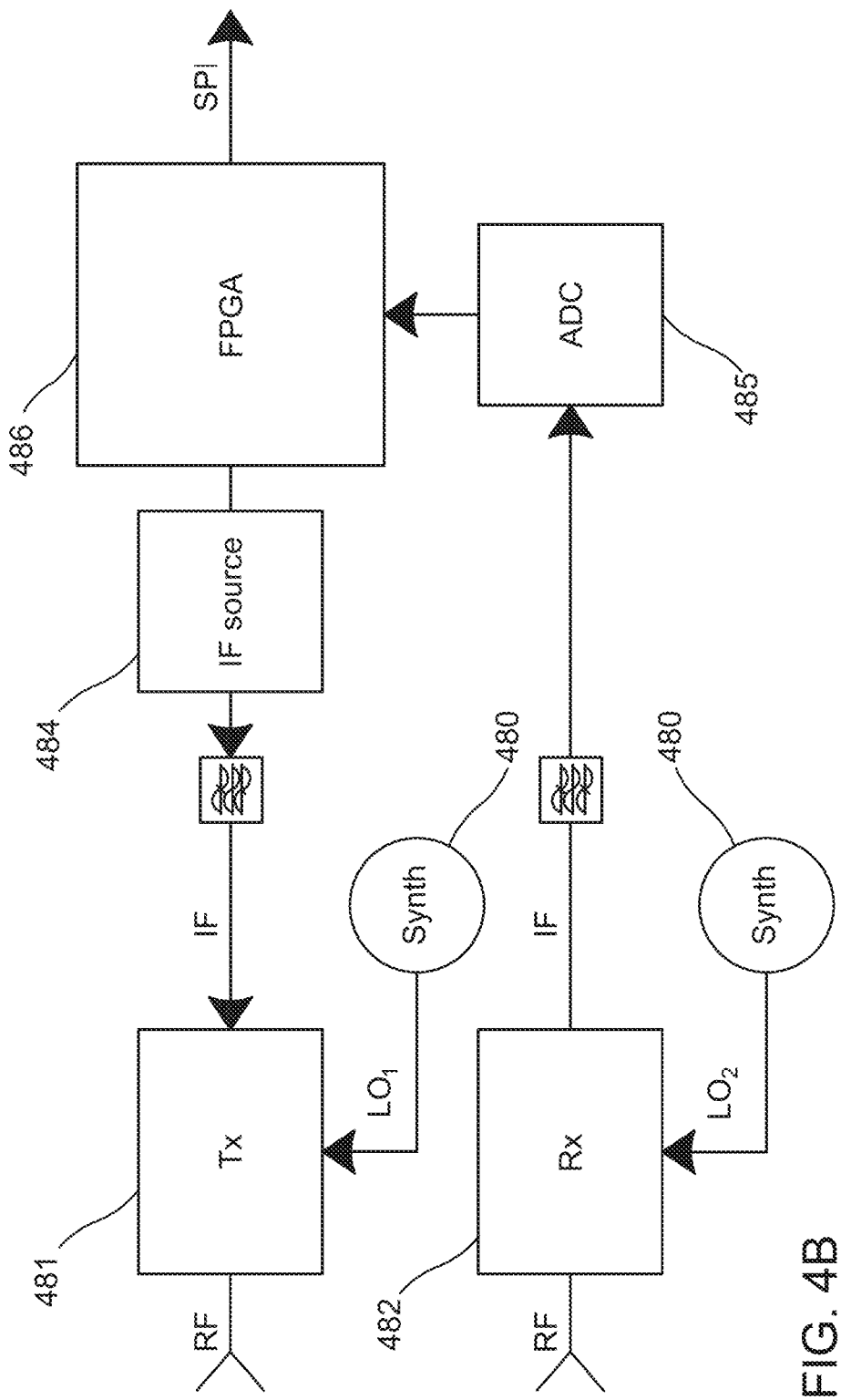
FIG. 4B shows a block diagram of example architecture of a radio frequency (RF) module, according to some embodiments.
Figure 4C:
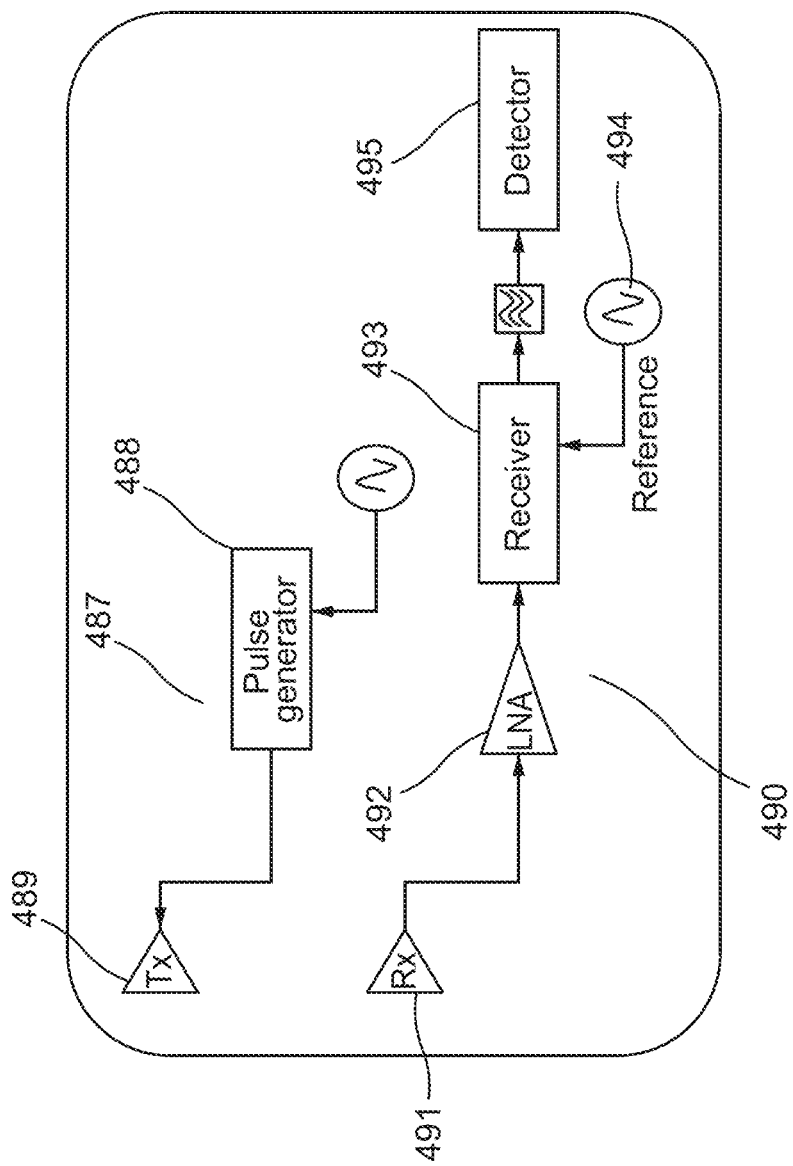
FIG. 4C shows a block diagram of another example architecture of an RF module, according to some embodiments.

FIGS. 4B and 4C are block diagrams that illustrate examples of RF sensor functionality disposed within an RF module (e.g., RF module 432) according to some embodiments. As noted herein, such functionality may be used for RF based fluid monitoring of fluid accumulation/content in tissue in accordance with the techniques described herein. Referring first to FIG. 4B, initially, one or more RF signals (e.g., a single "LO" signal, or different "$LO_1$" and "$LO_2$" signals, collectively "LO" signals) can be generated by a broadband synthesizer 480 (e.g., a pulse generator and synthesizer—LO). Such a synthesizer 480 can preferably include moderate phase noise performance and fast settling time capabilities (in some embodiments, one or the other). The RF module includes a transceiver portion 481, including a transmitting antenna (Tx) and associated circuitry for transmitting RF waves directed, for example, towards a tissue of interest in the patient's body, and a receiver portion 482, including a receiver antenna (Rx) and associated circuitry 482 for receiving reflected RF waves from, for example, the tissue of interest in the patient's body.

The LO signal at the transceiver (Tx) of the transmitter portion 481 is multiplied with an external sine wave at a low frequency intermediate frequency (IF) signal, generated by an IF source 484, and directed to the output of the transceiver (Tx). As noted above, the LO signal at transceiver portion 481 and the receiver portion 482 can be generated by one or two LO sources (e.g., synthesizer(s) 480). Output power can be controlled via digital control of a digitally controlled attenuator (DCA) on the RF transceiver path. An external reflected RF wave returning to a receiving antenna (Rx) is directed to the receiver portion and down-converted to an IF frequency by a down conversion mixer. The reflection characteristics (phase and amplitude) can be transformed to a new IF carrier (e.g., on the order of 250 KHz), filtered and amplified before the ADC 485.

Digital control for the functionality in FIG. 4B may be achieved directly by a processor and/or digital logic (e.g., an FPGA 486), which may be configured to control both the transceiver's configuration process, IF signal adjustments and associated switching.

Referring now to FIG. 4C, in some embodiments, the RF module 432 may be implemented using a transmitting portion 487 and receiver portion 490 as shown. For example, the transmitting portion 488 can include a pulse generator 488 and a transmitting antenna Tx 489 for transmitting the RF waves directed towards a tissue of interest in the patient's body. the receiver portion 490 may include a receiving antenna Rx 491, a low-noise RF amplifier 492, a receiver 493 that converts the reflected RF signals to an IF signal by using mixer and local oscillator 494, which may be a monostatic (sheared LO) or a bi-static system. The signal can be filtered, amplified and fed in to a detector 495, the output of which may be connected to additional circuitry for further signal processing.

With respect to potential RF/ECG interference, in some embodiments the following steps can be taken:

Ground Separation between digital and RF components: may be achieved by separating the digital and RF grounds, and utilizing a single connection point through ferrite bead.

RF module shielding may also be used which may comprise a metallic cover, for example, radio frequency shield 390 as shown in FIG. 3C.

Power circuitry considerations: different power paths may be utilized for different components/modules. Additionally, the power circuit may include filters to avoid noise.

ECG filtering may also be used to aid in minimizing RF interference which prevents high frequency signals interfering with the ECG circuitry/module.

Circuitry layout: ECG signal paths are physically separated from RF paths. In some embodiments, the ECG signal paths can also be physically separated from other lines that might interfere.

FIG. 4C shows an example general architecture of the RF module with low frequency IF and shared local oscillator (LO). As an example non-limiting example, with reference to FIG. 4C, the transmitted RF signal may be mixed with the IF signal (e.g., about 250 KHz) before transmission, so the transmission is actually 2 tones around the carrier RF signal, separated by about 500 KHz.

In some embodiments, the RF module 432 may include a calibration path (e.g., an electric reflector such as but not limited to a resistor on board) which generates a steady and constant or near-constant reflection uncorrelated with the external propagation path. This reflector generates a reflection profile with minimal dependencies to temperature, system noise and device location on the body.

In some embodiments, the RF module 432 itself may not have any processing components inside. For example, it may be controlled by a field-programmable gate array (FPGA) that defines in each or nearly each frequency point one or more of the frequency, output power levels, system gain, bypassing modes and/or enable/disable transmissions.

In some embodiments, the RF module 432 may support different types of waveform configurable options, including but not limited to normal operation, calibration frame operation, interleaved switching between normal and calibration frame operation, interleaved switching between normal and delayed path operation, and clear channel sensing. In some of these options, for example the normal and interleaved switching ones, the attenuation may be different per frequency, while in the case of clear channel sensing, there may not be any transmission. For the calibration frame operation, the attenuation can be the same for all frequencies but may be higher when compared to those of the normal operation.

In some embodiments, the transmit (Tx) and receive (Rx) switches may be respectively set to transmit and receive through a calibration path for the case of calibration frame operation, while for the clear channel sensing, Rx switch may be set to antenna and Tx to calibration path. For interleaved switching between normal and calibration frame operations and between normal and delayed path operations, in some embodiments, the Tx and Rx switches may alternate between calibration and antenna path per frequency, and normal and delayed path, respectively.

In some embodiments, the RF waves may be in the frequency ranges from about 100 MHz to about 1 GHz, 200 MHz to about 2.5 GHz, from about 200 MHz to about 3 GHz, from about 500 MHz to about 5 GHz, including values and subranges therebetween. In some embodiments, a thoracic fluid content (TFC) sensitivity may be configured to allow measurement of heart signals at distances up to about 25 cm, about 20 cm, about 15 cm, about 10 cm, about 5 cm, including values and subranges therebetween, inside the body onto which the disclosed sensor is attached. In some embodiments, the dynamic range is no less than 100 dB, measured in the presence of a strong coupling signal between transmission & reception. Further the waveform may be stepped frequency (16-128 frequencies), arbitrary with 1 MHz accuracy & resolution. In some embodiments, actual frequencies selected may be contiguous or not, depending on regulatory requirements. In some embodiments, the dwell and settling times may be configurable to allow 16-128 frequencies within less than 5 to 20 ms, respectively.

Details on RF-based measurements of physiological parameters such as thoracic fluid content have been discussed in U.S. Patent Publication No.: US 2011/0130800, filed Apr. 14, 2010, titled "Methods and Systems for Determining Fluid Content of Tissue"; and PCT International Patent Publication No.: WO 2012/011066, filed Jul. 21, 2011, titled "Implantable Dielectrometer," the disclosures of which are incorporated by reference herein in their entireties.

It has been noted above that the sensor may include indicators providing information on the attachment level of the patch housing the sensor to a skin of the wearer of the sensor. Such information may be obtained from RF-based measurements as discussed in PCT International Patent Publication No.; WO 2016/115175, filed Jan. 12, 2016, titled "Systems, Apparatuses, and Methods for Radio Frequency-Based Attachment Sensing," the disclosure of which is incorporated by reference herein in its entirety.

In some embodiments, the FPGA 406, with a top-level view of which shown in FIG. 4D, may be configured to interface with the RF module 432. For example, the FPGA 406 is configured to one or more of control the transceiver module, control the RF discrete pins, control the ADC module, generate the IF signal for the RF module 432, and acquire ADC (analog-digital conversion) output samples, synchronized with the generated IF signal. Further, in some embodiments, the FPGA 406 is configured to process the ADC output samples to generate the baseband data. In addition, in some embodiments, the FPGA 406 may be configured to interface with the microcontroller or microprocessor 408. For example, the FPGA 406 may start RF transmission (per frame) upon command from microprocessor 408, save baseband data to local RAM, per frame, for microprocessor 408 to read, allow microprocessor 408 read/write transactions towards configuration memory, provide a debug interface for the microprocessor 408, and/or allow microprocessor 408 to change configuration settings using a dedicated memory.

In some embodiments, the FPGA can support up to 128 frequencies, allowing for a different gain and dwell time per frequency. In some embodiments, power consumption can be minimized by using several clock frequencies within the design and gating unused clock signals. In some embodiments, microprocessor data acquisition can be performed using a separate clock, allowing the shut-down of the entire control & processing pipe while reading the data.

In some embodiments, the sensor disclosed herein may comprise an accelerometer and the accelerometer may be used to determine one or more of the physical activity, posture and respiration rate of a patient wearing the sensor. For example, a three-axis (3D) accelerometer 422 may be used to acquire data on patient movements and posture as well as the respiration rate, and a processor (of the sensor or an external server, for example) receiving the acquired data may use the data (e.g., in conjunction with data obtained by the sensor such as ECG data or RF-based measurements) to determined physiological parameters of the patient, such as the lung fluid level of the patient. The 3D accelerometer 422 may be used to aid RF and/or ECG analysis by detecting different types of motion segments in the recording so that the conditions of the measurements of the RF and/or the ECG may be interpreted/analyzed accordingly. For example, in some embodiments, RF and/or ECG measurements may be performed while the patient wearing the sensor is active or at rest. The analysis of the RF and/or ECG data may then depend on the state of the patient's physical activity (e.g., at rest, low intensity activity, high intensity activity, etc.). In such embodiments, the accelerator may be used to identify the patient's physical state so as to properly analyze and interpret the RF and/or ECG measurements.

In some embodiments, the accelerometer 422 may also contain an internal tap detector, which may be used for generating a patient triggered event (e.g., using "double tap" feature). The acceleration signal can be used to calculate respiration rate. FIG. 4A shows an example embodiment of a sensor comprising a 3D accelerometer 422, RF antennas 404a, 404b, ECG processing circuitry coupled to ECG electrodes, a microcontroller 408 (which may be alternatively referred as microprocessor throughout this disclosure) and a telemetry (e.g., Bluetooth®) 414. In such embodiments, for example, the micro-controller 408 may receive data on patient respiration rate, movements, posture, ECG as well as RF-based measurements of the patient and process, and/or transmit to an external processor via the telemetry 414 for further processing, to determine a physiological parameter of the patient. As an example, the micro-controller 408 of the sensor may cause the Bluetooth® telemetry 414 to transmit the noted data and measurements to an external server which in turn analyzes the RF measurements, the ECG, posture, movement, and/or respiration rate data to determine the lung fluid level of the patient. As an another example, the external server may analyze ECG data to determine patient health conditions related to one or more of a heart rate, atrial fibrillation, flutter, supraventricular tachycardia, ventricular tachycardia, pause, atrioventricular (AV) block, ventricular fibrillation, bigeminy, trigeminy, ventricular ectopic beats, supraventricular ectopic beats (SVEB), bradycardia, and tachycardia. The determination of patient physiological health parameters (e.g., lung fluid level or the above-noted health conditions) may allow the server to provide a notification on health-related events of the patient wearing the sensor for which the data came. For example, upon determining an arrhythmia condition from data received from a sensor, an external server may provide a notification indicating a cardiac event with respect to the wearer of the sensor that transmitted the data.

In some embodiments, the sensor may also include a temperature sensor, conductance sensor, a pressure sensor, a respiration sensor, SPO2, and/or a light sensor. For example, a respiration sensor can include an accelerometer configured to monitor the patient's chest movements, e.g., during certain portions of the day and/or night or during an RF measurement. For instance, a 3D multi-axis, multi-channel accelerometer can be configured to, on a first channel, monitor for a patient movement and/or posture, and on a second, different channel, monitor the chest movements of the patient to determine respiration rate and other related data. Alternatively, a respiration accelerometer can be provided in the device that is separate from a posture sensing accelerometer. In some examples, the respiration rate measurement can be based on the operation of a tri-axis micro-electromechanical system (MEMS) accelerometer within the device mounted on the patient's torso. The accelerometer can measure projections of the gravity vector on its intrinsic axes. From these measurements, a respiration rate can be derived based on measured quasi-periodic changes of the projections that occur due to respiration movements of the patient's rib cage.

In other examples, the respiration rate and/or other respiration data can be derived from the RF signals themselves. For example, dedicated respiration circuitry can be provided and/or the processor can be configured with instructions to cause the processor to monitor the reflected RF waves as described herein and determine respiration rate and related data therefrom. In some embodiments, respiration characteristics such as exhale vs. inhale times can also be measured via an accelerometer and health conditions such as sleep apnea may be detected from accelerometer measurements.

In some embodiments, RR, which denotes ventricular interbeat interval on ECG, may be derived from ECG data and the RR accuracy can be improved by fusing the data from two or more of these RR measurement methods.

Figure 5A:
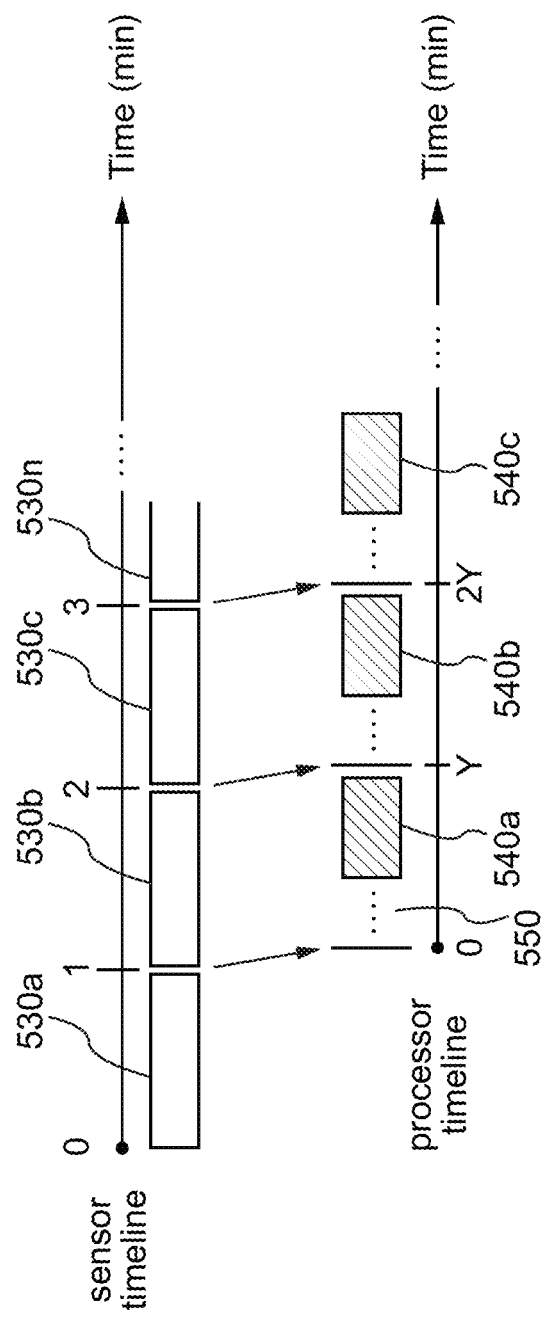
FIGS. 5A-D show example illustrations of the measuring and processing of physiological data acquired from one or more patients via the sensor(s) disclosed herein, according to some embodiments.

With reference to FIG. 5A, in some embodiments, an example illustration of the continuous measurement and processing of physiological data acquired from a single sensor or device is shown. In some embodiments, as discussed above, the sensor may acquire data related to the physiological and/or physical state of a patient wearing the sensor, including but not limited to ECG data, accelerometer data, etc. In some embodiments, the measurement of the data 530a may occur as data segments having lengths of between about 15 seconds to about 1 minute, about 30 seconds to about 3 minutes, about 1 minute to about 10 minutes, or longer time periods, including values and subranges therebetween. In some embodiments, the sensor may be configured to make such sets of measurements in a continuous or at least nearly-continuous manner. For example, after the measurement of a data segment 530a, the sensor may proceed with measuring an additional data segment 530b immediately, or at least within a very short time period. For example, the sensor may measure the additional data segment 530b before the first data segment 530a is transmitted to an external device such as a gateway device or some other processor. In some embodiments, the additional data segment 530b may be measured or acquired anywhere between zero second (i.e., immediately) and about 5 seconds, between about 0.25 second and about 3 seconds, between about 0.5 second and 2 seconds, about 1 second, including values and subranges therebetween, after the previous data segment 530a is acquired. Similarly, after data set 530b is acquired, in some embodiments, the sensor may proceed with measuring or acquiring an additional data segment 530b in a continuous or nearly continuous manner (as described above). It is to be noted, however, that the duration, if any, between the measurement of data 530a and the start of the measurement of data 530b may not be the same as the duration, if any, between the measurement of data 530b and the start of the measurement of data 530c. In some embodiments, the duration of the data segments is a preconfigured parameter which may change per different measurement regimens and for different patients, the value of which can range between about 1 second and about 20 minutes.

In some embodiments, once a data segment such as 530a is acquired, the data 530a may be immediately transmitted to a server via a gateway device for processing and analysis as described above. Such processing and analysis may take up some amount of time (denoted 550 in FIG. 5A) before the data, after processing and analysis, is received at a database for use by a user (e.g., a healthcare provider) to detect, based on the processed data 540a, any health events of a patient wearing the sensor, such as arrhythmic events. In addition to events, an analysis engine may analyze the ECG data segments 530 to derive a plurality of physiological parameters. Such parameters can include heart rate, average R-R intervals, heart rate variability, T wave parameters, among others. With regards to accelerometer data, derived parameters can include respiration rate, patient posture information, and patient movement information. In some embodiments, the time between the transmission of the data 530a by the sensor and the availability of the processed data 540a to a user (denoted Y in FIG. 5A) may be anywhere between about 3 minutes and about 25 minutes, between about 4 minutes and about 20 minutes, between about 5 minutes and about 15 minutes, between about 10 minutes and about 15 minutes, between about 13 minutes and about 17 minutes, including values and subranges therebetween.

In some embodiments, the reception and processing/analysis of acquired data 530a, 530b, 530c, . . . , to produce processed data 540a, 540b, 540c, . . . , may proceed in a continuous or semi-continuous manner. In other words, upon completion of the processing/analysis of a received data segment (e.g., 530a), the processing/analysis of a subsequently received data (e.g., 530b) may proceed either immediately or within a short period in the range from about 0.5 seconds to about 5 seconds, from about 0.75 seconds to about 3 seconds, about 1 second, including values and subranges therebetween. In some embodiments, subsequently acquired data (e.g., 530b, 530c) may be queued while a previously acquired data (e.g., 530a) is being processed and analyzed.

In some embodiments, patient health events such as arrhythmic events may be detected based on an analysis of a single segment (or set of data), e.g., one of 530a, 530b, 530c, etc. In some embodiments, such events may be detected based on analysis of a plurality of sets of data. For example, one or more sets may indicate onset of an event and a later data segment may indicate the offset of the event. As an example, a first data segment 530a may include an onset event for atrial fibrillation. And a subsequent data segment 530n, that may be collected several minutes (e.g., 20 minutes later) or hours later (e.g., 2-4 or more hours) may include a corresponding offset event for the atrial fibrillation. In another example, the analysis engine may need several data segments 530 in order to confirm the presence of a particular event, e.g., a ventricular tachycardia or ventricular fibrillation event. In such embodiments, a notification may be generated indicating the occurrence of the health events.

Figure 5B:
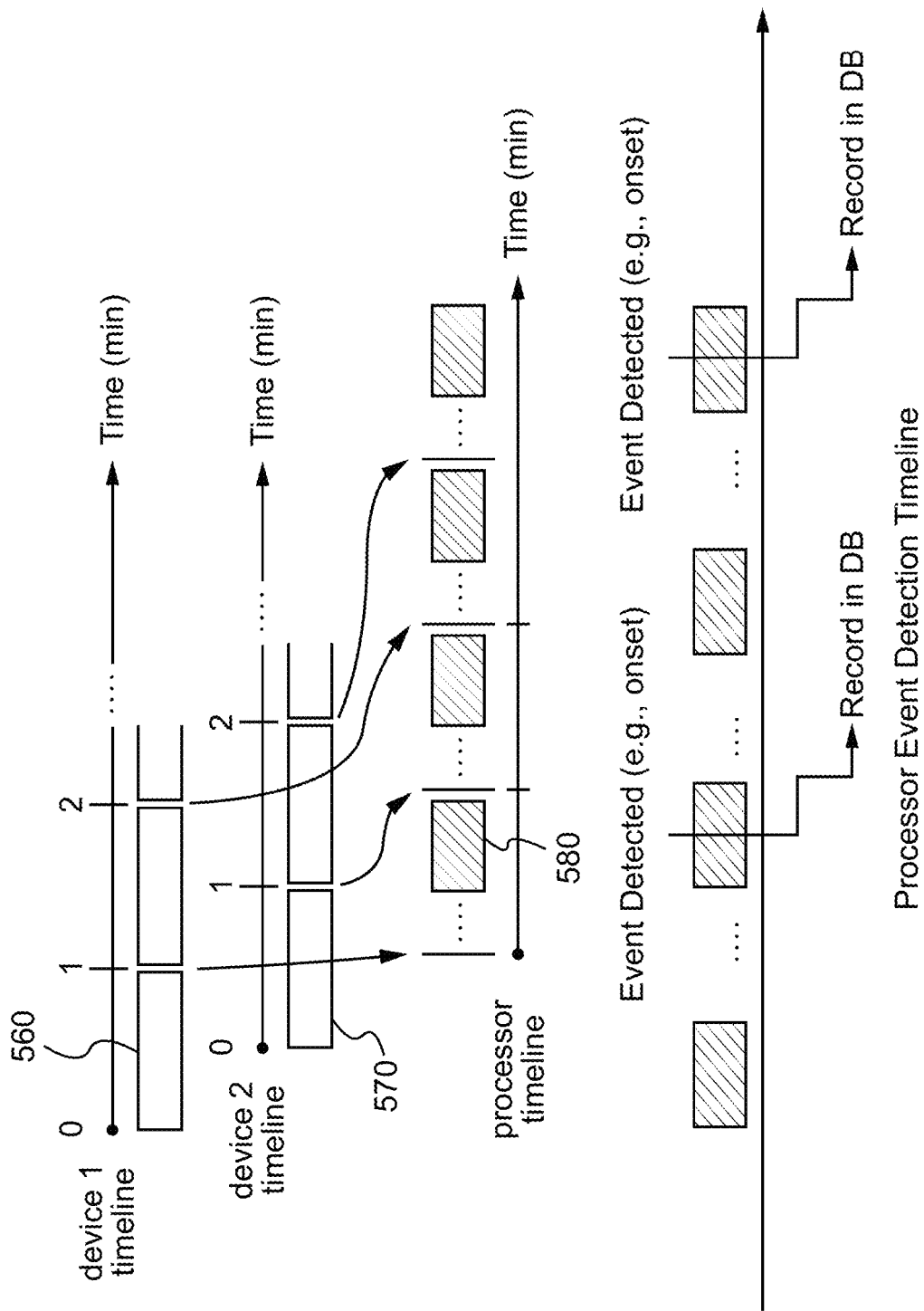

With reference to FIG. 5B, in some embodiments, a plurality of sensors or devices worn by different patients may make measurements or acquire data and transmit the acquired data 560 and 570 to a gateway device and a processor for processing and/or analysis. In such embodiments, similar to the discussion above with reference to FIG. 5A, the processing/analysis of the received data may occur continuously or at least semi-continuously. The ECG data acquisition and/or transmission process of device 1 corresponding to a first patient may differ from the ECG data acquisition and/or transmission process of device 2 corresponding to a second, different patient. For example, the ECG data segment lengths for the two devices may be different. For device 1, for example, the ECG data segment length may be set to 1 minute. For device 2, for example, the ECG data segment length may be set to 3 minutes. For the two devices, the delays and/or speeds of transmission of the ECG data from the devices to the gateways and to the servers may also be different. For example, the two devices may be in very different environments that affect the data transmission rates and connections between the devices and the gateways. Further, device 1 may not be in proximity of a gateway and thus unable to transmit its data until connection with a gateway is reestablished. However, as soon as device 1 is within range of a gateway, connection can be reestablished and device 1 may immediately transmit the stored ECG data segments.

In some embodiments, while a plurality of ECG data segments are recorded, processing of such data segments (in some embodiments) leads to the identification of events and/or physiological parameters in only a portion of such data segments. The identification of such events may then be recorded in a database (e.g., event onset, event offset, and the like). This processor timeline is illustrated in FIG. 5B ("Event detection timeline"). In some embodiments, the respective data segment may be stored in the database, or, a reference to the data segment may be stored (e.g., time, number).

In some embodiments, ECG the data segments can be concatenated to create new data segments of predefined file lengths that are independent of the original ECG data segment length. For example, such concatenation can be done on the server using, for example, a merger tool. As a specific illustration, a sensor may be configured to operate to continuously acquired 1 minute long ECG data segments. The server may collect 5 minutes of such ECG data segments, and using the merger tool, combine the data that may or may not have periods of overlap, and thus allow for analysis on the concatenated data.

In addition to events, in some embodiments, trends associated with collected physiological data (from the data segments) may be produced (e.g., via software algorithms implemented by the processor(s)). Such trend information for one and/or another patient may be displayed (e.g., display device, printed report) for a technician, doctor, healthcare worker or a patient. Such trends may be produced by processing the collected data for physiological parameters which may include, for example, heartrate, respiration rate, posture, activity, movement, tissue fluid levels, hydration, cardiac events (e.g., arrhythmias, average R-R intervals, etc.), maximum and minimums thereof over a time period (minute, hour, day, week, month, year).

Figure 5C:
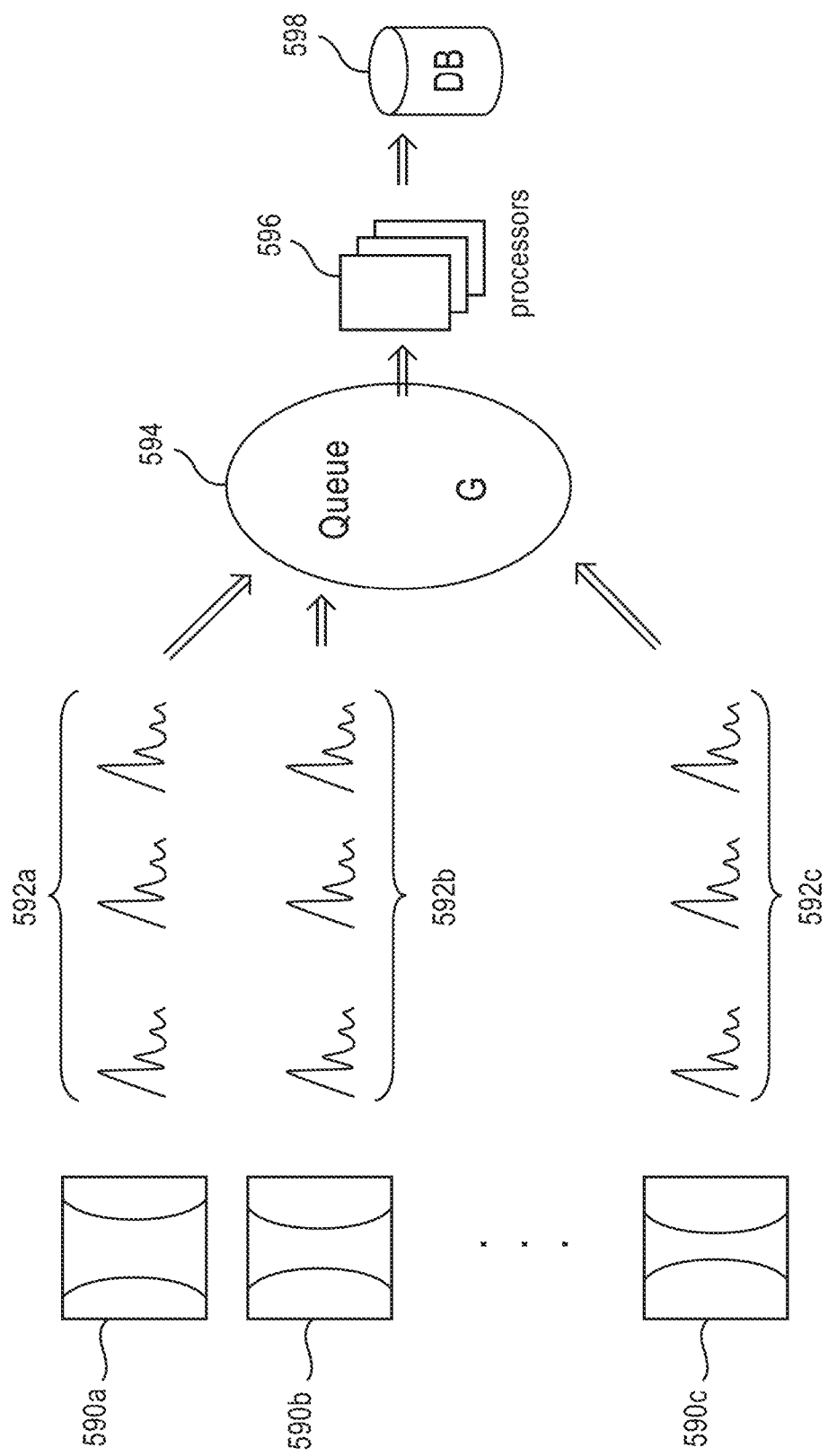

The gateway device and/or the processor may, however, classify the received and/or the processed data based on which patient the data came from so that any health event detected from the data may be properly ascribed to the correct patient. Further, in some embodiments, the gateway device and/or processors may prioritize the data to be processed and/or analyzed. For example, data sets with indications of certain health events and/or arrhythmias may be given priority for processing/analysis. For example, as shown in FIG. 5C, a plurality of devices or sensors 590a, 590b, 590c, . . . , may transmit physiological data 592a, 592b, 592c, . . . , and the received data may be placed in a queue 594 for processing by one or more processors 596, and in some instances, by gateway devices. In some embodiments, there may be a plurality of processors and some or all of the received data may be processed in parallel. In some embodiments, the processors 596 may process/analyze the data sets in a continuous or at least nearly-continuous manner, and notifications may be generated at the database 598 (e.g., for use by a health care provider) when health events such as arrhythmia events are detected.

Figure 5D:
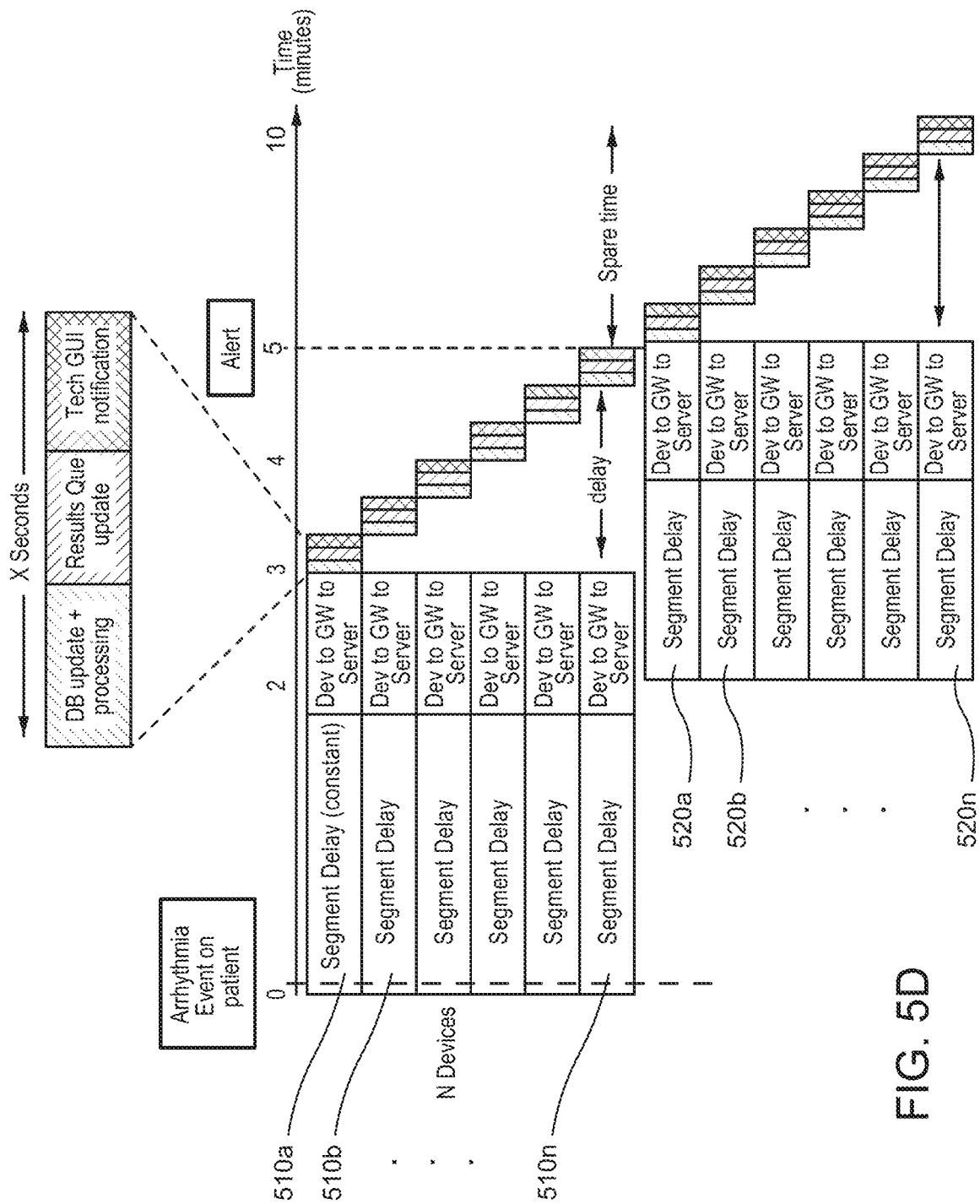

FIG. 5D shows an example illustration of the continuous measurement and processing of physiological data acquired from a plurality of patients via the sensor(s) disclosed herein, according to some embodiments. FIG. 5D assumes that an onset of an arrhythmia event is detected in the ECG data of the patient a little after 0 minute point on the time line in order to demonstrate how long the disclosed monitoring system and/or methods take to detect an arrhythmia condition occurring in one or more patients (e.g., a duration that is treated as a design requirement and specified as a latency in the system in notifying a technician about a detected condition and/or event). Accordingly, FIG. 5D highlights an advantage of the disclosed systems(s) and/or method(s) over prior art system(s) and/or method(s) in showing how quickly a technician and/or other authorized person(s) and/or entity (e.g., another computer-based response system) are able to respond to a critical event occurring to a patient. As shown, in this example, the latency is designed such that a technician is notified within 10 minutes of an onset of an event occurring, and within 5 minutes under ideal circumstances, leaving about an additional 5 minutes for the system and/or the technician to generate an event report that is then transmitted to a relevant physician or designee of the physician.

The example presented in FIG. 5D shows the use of several sensors to monitor health conditions of several patients continuously, with physiological data being recorded and transmitted to external servers in a continuous manner for processing so as to identify health related events. For example, the sensors may perform RF measurements and/or record patient ECG data (packed into discrete ECG data packets) and the accelerometer may monitor the patient movement/motion, posture data and pack them into discrete accelerometer (ACL) data packets and transmit these measurements/data packets to an external server (via a gateway device, for example) continuously. In some embodiments, the sensors may perform the measurements and/or record the data continuously and transmit the measurements and/or the data periodically, e.g., every pre-configured period of time (e.g., about every 10 minutes, about every 5 minutes, about every 3 minutes, about every 2 minutes, about every 1 minute, about every 45 seconds, or about every 30 seconds, including values therebetween). In some examples, the pre-configured period of time need not be a fixed period of time, but can be configured to vary from one period to the next (e.g., about 2 minutes for a first transmission, and about 45 seconds for a next transmission, and so on).

With reference to the example embodiments of FIG. 5D, N sensors disclosed herein (e.g., each one of the N sensors assigned to a different patient) may perform physiological and/or environmental measurements (510a through 510n) in a continuous manner, each session occurring during a pre-configured measurement time duration, a measurement file segment length $T_{segment}$. For example, the measurement time duration ($T_{segment}$) may be configured to be about 10 minutes long, about 5 minutes long, about 3 minutes long, about 2 minutes long, or about 1 minute long, about 45 seconds long, or about 30 seconds long, including values therebetween. A typical value for the measurement time duration is about 2 minutes. As explained in further detail below, this duration was selected after experimentation and analysis showed that a measurement time duration of about 2 minutes is optimal when designing the system to achieve about a 10 minute latency time (as noted above, the latency time is a design requirement concerning a duration from when an arrhythmia condition and/or a certain event is detected by the system to when a notification is sent to a technician or other authorized person or entity concerning the condition and/or the event).

It is noted here that the measurement data in the example scenario described above consists of about 2 minutes of ECG data that is stored in the sensor within a non-volatile memory (e.g., memory 416 of FIG. 4). The ECG segments that are stored in the memory are constructed based on the raw ECG signals received from the ECG leads 220. For example, the ECG data can include pre-processed raw ECG information (i.e., ECG data that has not yet been standardized) which is then sent to the external server without further processing. In other examples, the ECG data from the leads may be minimally pre-processed, e.g., amplified, de-noised, and filtered to eliminate stray interference signals overlayed on the ECG data prior to being sent to the external server. In yet some examples, the microprocessor 408 may employ a QRS detector algorithm (QRS—the series of deflections in an electrocardiogram that represent electrical activity generated by ventricular depolarization prior to contraction of the ventricles) to further standardize the ECG data through pre-filtering, rectification, integration of the signal, thresholding, R-R interval detection, and beat detection. Further, in some embodiments, the microprocessor 408 can also perform one or more of compression of data and signal processing to calculate one or more of heart rate, respiration rate, arrhythmia detection, and/or the like.

Similarly, continuously measured accelerometer data can be sent to the external server without further processing. In some examples, the accelerometer data can be minimally processed to remove known artifacts (e.g., spikes and out-of-range values). In yet some examples, the accelerometer data can be matched via stored templates on the device to one or more pre-recorded patient movement and/or posture patterns. For instance, the microprocessor 408 in the device may include algorithms that can detected whether the patient is in a supine state, reclined state, lying on his/her side (e.g., left or right sides as the first and second sides), upright state, and/or sitting up. On completing the recording of a measurement segment, the microprocessor 408 can update a measurement directory within the memory 416 to indicate a completed measurement file. The microprocessor 408 can be configured to ignore an aborted measurement, e.g., by not saving the measurement file within the memory 416 and/or not updating the measurement directory. In such situations, the microprocessor 408 may record an aborted measurement flag to a separate location in the memory 416 for later troubleshooting.

In the example of FIG. 5, the N sensors perform continuous measurement and transmission of only ECG data and/or accelerometer data. The N sensors also perform measurement and transmission of RF-based data in a periodic, non-continuous manner, as described in further detail below. In addition, each sensor may include additional sensors including but not limited to a temperature sensor, a conductance sensor, a pressure sensor, a respiration sensor, an accelerometer, a light sensor, and/or the like, may also perform measurements while the sensor is acquiring ECG and/or RF data. In alternative implementations, the sensors may also perform RF measurement and data transmission (and/or measurement and transmission of other types of sensor data) in a continuous manner as described herein for ECG and/or accelerometer data.

As shown in the figure, the first sensor worn by a first patient may perform the measurements for a duration of $T_{segment}$ (510a) and proceed immediately or at least immediately with performing additional measurements (520a) as the previous measurements are being transmitted to the external server via a gateway device (e.g., gateway device 130 of FIG. 1) for processing. The same applies to the other N−1 sensors, each performing measurements for $T_{segment}$ duration (510b through 510n), and proceeding immediately or at least immediately with additional measurements (520b through 520n) as the measurements from the previous measurements are being transmitted to an external server via gateway devices. As such, the sensors perform physiological measurements in a continuous or at least a nearly continuous manner without the need for interrupting or delaying measurements as previous measurements are being transmitted to an external server for analysis to determine health conditions or events of the patients wearing the sensors. In some embodiments, data may be collected in the direct memory access (DMA) of the microcontroller of the sensor (e.g., while the communication is not occurring between the sensors and the external device), after which the data may then be transmitted upon establishment or reestablishment of communication.

In some embodiments, succeeding measurements (e.g., 510a and 520a, etc.) by the same sensor may not be continuous but may occur with a short gap in between the measurements. For example, after the initial measurements 510a, there may be a gap of up to about 1 minute, about 30 seconds, about 15 second, about 10 second, about 5 seconds, about 3 second, including values therebetween, before the subsequent measurements 520a take place. This gap, however, may be vanishingly small (i.e., zero, near zero), resulting in a continuous measurement by a sensor as the gathered measurements are being transmitted to an external server. Such a gap may be provided, for example, to allow for a sensor to establish a secure Bluetooth® connection to a corresponding gateway device 130 (FIG. 1) for uploading the measurement data to the external server. Such a time gap may also be used to perform a series of tests on the measurement data before the data is actually uploaded via the gateway device to the external server. In this regard, the following are example on-line tests that may be performed after every measurement segment and the failure of one or more of these tests may result in an aborted measurement and/or transmission of the data:

Device-in-patch sensing is performed to confirm whether the sensor 270 is securely within the patch 210. For example, the device checks for an electronic connection between the on the device pads to ensure the device is in place.

Button push: if a button on the sensor 270 is pushed during an on-going measurement, a connection between the sensor 270 and the server and/or the gateway may be reset, causing an ongoing transmission of data to be aborted.

Temperature is over/below thresholds, e.g., above 40° C. or below 20° C.

Relative humidity is outside recommended operating range, e.g., between 10-90%, non-condensing.

Battery is below a pre-configurable threshold, e.g., below 15% of full charge.

In some embodiments, the number of sensors N (equivalently number of patients wearing the sensors) the measurements of which can be processed by the same server may be determined from the equation $N=T_{segment}/t_{process}$, where $t_{process}$ denotes the processing time of a single file from a single sensor by the server. As $T_{segment}$ increases $t_{process}$ may increase as well (e.g., in a linear fashion), resulting in an upper bound for N that depends on the efficiency and processing power of the server in processing a single measurement (which may be related to the duration of $t_{process}$). Taking practical considerations into account (e.g., processor speed and or memory limitations), an example amount of time processing time for a file ($t_{process}$) is in between about 15 seconds and a few milliseconds. For example, a current processing time is typically around 8 seconds. Using $t_{process}=8$ seconds in the equation above, we get a maximum value for N as being around 2×60/8=15 patients. These calculations show that the example system described above is designed to detect multiple cardiac events occurring at the same time in around 15 patients in the field (e.g., arrhythmia conditions and/or any other predetermined events) and notify technicians, physicians, and/or other relevant person(s) within 5-10 minutes latency time. As such, according to the above example design, within 5-10 minutes from the onset of an event detected in a group of monitored patients, the system will issue a notification to the technician. Further, multiple notifications may issue for each event and for each patient that may be occurring simultaneous, all within the designed latency time.

Example Wireless Transmission Rates and Performance for a Selected System to Implement the Disclosed Concepts The implementations described above requires that ECG and/or accelerometer data be transferred continuously from a patient worn device to a remote monitoring center server. In order to implement such a requirement, a sampling rate of 250 Hz for 16 bit ECG data and 50 Hz for 3-axis, 16 bit accelerometer data can be assumed. Based on these assumptions, a data rate of 250×2+50×2×3=800 Byte/sec can be achieved. Further, adding ~20% for file/packet data (header/CRC/among other things) and retransmissions/reconnections, an average throughput of 1 KB/sec can be achieved, which requires a bandwidth of about 1 KHz.

In the event of a long term broken connection link (e.g., lasting several hours), the device can be configured to transfer the data as soon and as fast as possible once the link is reestablished, subject to the link quality. Accordingly, based on these assumptions, a selected design can be based on implementing the wireless link using a Bluetooth® to TCP/IP gateway pipe between the device and the server. As such, the system can be comprised of two sub-links:

Link between the device and the gateway (e.g., Bluetooth® 4.0 can be used).

Link between the gateway and the server PC (Cellular or WiFi™ can be used; IEEE 802.11 standards).

A total link performance depends on bottleneck issues between the sensor-gateway device and gateway device-external server links. Typically, the bottleneck issues occur in the gateway device-external server link as a gateway device can be configured to be carried by the patient in substantially close proximity to the device, while cellular or WiFi™ coverage can be expected to be variable during wear time.

As noted in further detail below, the wireless transmission of RF-based measurement data occurs on a periodic basis. A wireless connection to the gateway device and/or external server needs to be established only soon after an RF measurement is completed as described in further detail below. Accordingly, a standard Bluetooth® connection can adequately support the data throughput required for the transmission of the RF measurements (in addition to the ECG and/or accelerometer data described above) via the gateway device 130 to the external server.

In some embodiments, besides the continuous operation mode discussed with reference to FIG. 5D, there are several other modes in which the disclosed sensor enter. For example, the sensor may be put in an OFF mode to allow for long term storage of the sensor and/or to reset the execution of any software on the sensor. In some embodiments, putting the sensor in an OFF mode may lead to all components being turned off; measurements, communications and status checks not being performed, the sensor's button being deactivated; and measurements and schedule/configuration being erased. In some embodiments, while operating in the OFF mode, the microprocessor/microcontroller may go into deep sleep mode while in the charger. If removed from charger, the microprocessor may disconnect battery.

In some embodiments, when the sensor is operating in the OFF mode and is placed in a charger, the device may be powered-on and system power-up sequence may be activated, testing all its peripherals, logging the status, without erasing any or at least most memory or losing the device identity and pairing. The device then initiates Bluetooth® communication. If the Bluetooth link is unavailable, the device may retry communicating periodically. The device exists OFF mode only once a successful connection has been established with the server.

In some embodiments, the sensor may enter pairing mode when connecting with the gateway device (e.g., via a Bluetooth® link). Pairing can be done only if the sensor is powered on (not in OFF mode), performed by a dedicated push of the technician button (e.g., a physical or soft button provided on the device and configured to be actuated by an authorized technician only and not the patient). Pairing cannot be performed during measurement. While in operation in the pairing mode, in some embodiments, the sensor may be discoverable for a period of time (e.g., 4 minutes) pending pairing request from GW, and successful and unsuccessful pairings may be represented by different lights on an LED on the sensor.

In some embodiments, the sensor may also operate in a scheduled operation mode where the sensor performs scheduled measurements, status tests, activating links when not in continuous mode. The sensor may enter the mode upon command from server. When operating in this scheduled operation mode, in some embodiments, scheduled measurements, Bluetooth® connection attempts and test-status commands are carried out every configurable time according to schedule, and a configurable snoozing rule is activated in case the action had failed (e.g., number of attempts, snooze interval). In some embodiments, link to server is disconnected when performing measurements. When in charger and operating in this mode, in some embodiments, the sensor LED may indicate charging and patient assignment status, and measurements may not be taken, unless in special debug mode.

In some embodiments, the sensor may be in an attachment mode which allows for testing the patch attachment using the RF and/or accelerometer signal quality. Such tests may be performed when a patch is attached to a surface such as skin. In some embodiments, the sensor may enter the attachment mode while also being in any one of the operation modes. For example, the attachment test can be performed every time the microprocessor detects the sensor had been inserted into the patch, after being in the charger. Detection can be done using an interrupt signal indicating a closed circuit.

In some embodiments, while operating in the attachment mode, RF and/or accelerometer signals are checked to detect when patch is on body (e.g., based on motion detector and/or RF signal level). Further, the success or failure of the attachment test may be indicated by the sensor LED, and in case of failure a configurable snoozing rule can be triggered. Once the test is completed, in some embodiments, the result (indicating attached/not-attached) can be saved and may be reset only when placed in the charger. In some embodiments, the test may be successful, and in such embodiments, the sensor enters the measurement state; otherwise measurements are aborted and the sensor enters to scheduled operations mode.

RF-Based Measurement Process

Further, in these embodiments, in addition to the continuous measurement and transmission of ECG and/or accelerometer data described above, one or more of the N sensors may also perform between about 1 to about 50 scheduled RF-based measurements (e.g., to determine lung fluid level as discussed above) in a 24 hour period. The number of scheduled RF-based measurements may range from about 7 to about 40, from about 8 to about 30, from about 9 to about 30, from about 10 to about 26, from about 12 to about 24, including values and subranges therebetween. Typically, a preconfigured default number of scheduled RF-based measurements may be between 12-24 measurements per 24 hour period. A physician or other authorized person or entity may configure the number of measurements for an individual patient through a configurable parameter stored in the device memory. Each measurement period may occur in a period lasting about 2 minutes, about 1 minute, about 45 seconds, about 30 seconds, including values therebetween. The measurement period may also be configured through a configurable parameter stored in the device memory. A typical value for measurement period During such measurements, the RF waves may be in the frequency ranges from about 100 MHz to about 1 GHz, 200 MHz to about 2.5 GHz, from about 200 MHz to about 3 GHz, from about 500 MHz to about 5 GHz, including values and subranges therebetween.

Initially, a baseline RF-measurement of the patient's fluid level can be recorded. For example, the system may carry out a baseline RF measurement of the patient's thoracic fluid content and store this information in the memory of the device, e.g., memory 416, or on the external server. Subsequently, when an schedule RF-measurement is performed, a thoracic fluid index value can be calculated based on a measurement of the RF signals relative to the baseline values as described below. Over time, a trend of the thoracic fluid index value may provide an indication to a physician or other trained profession whether the patient's heart failure condition is improving and/or worsening. For example, an increasing index over a period of time may indicate that thoracic fluid accumulation is increasing and appropriate remedial measures may need to be taken.

Since the accuracy of the RF-measurement can be affected by patient posture and/or motion, the system can be configured to monitor the accelerometer signal during an RF measurement to detect a problematic posture of the patient and/or movement during the RF measurement. A motion detection algorithm can be implemented for this purpose to detect, based on accelerometer data immediately prior to an RF measurement, whether the patient movement is outside an acceptable range. For example, the sensor 110 may analyze about 5-10 seconds of patient movement data before deciding whether to retain or discard an RF measurement. The duration of accelerometer data that is used by the motion detection algorithm can be configured via a configurable parameter stored in the memory 416 of the sensor 400. If the RF measurement is to be discarded, the microprocessor 408 can be configured to re-take an RF measurement after a suitable wait time. For example, the wait time may be pre-configured to be around 30-60 seconds or around 5 minutes, 10 minutes, or more. The wait time can be changed via a configurable parameter stored in the memory 416 of the sensor 400.

Figure 6:
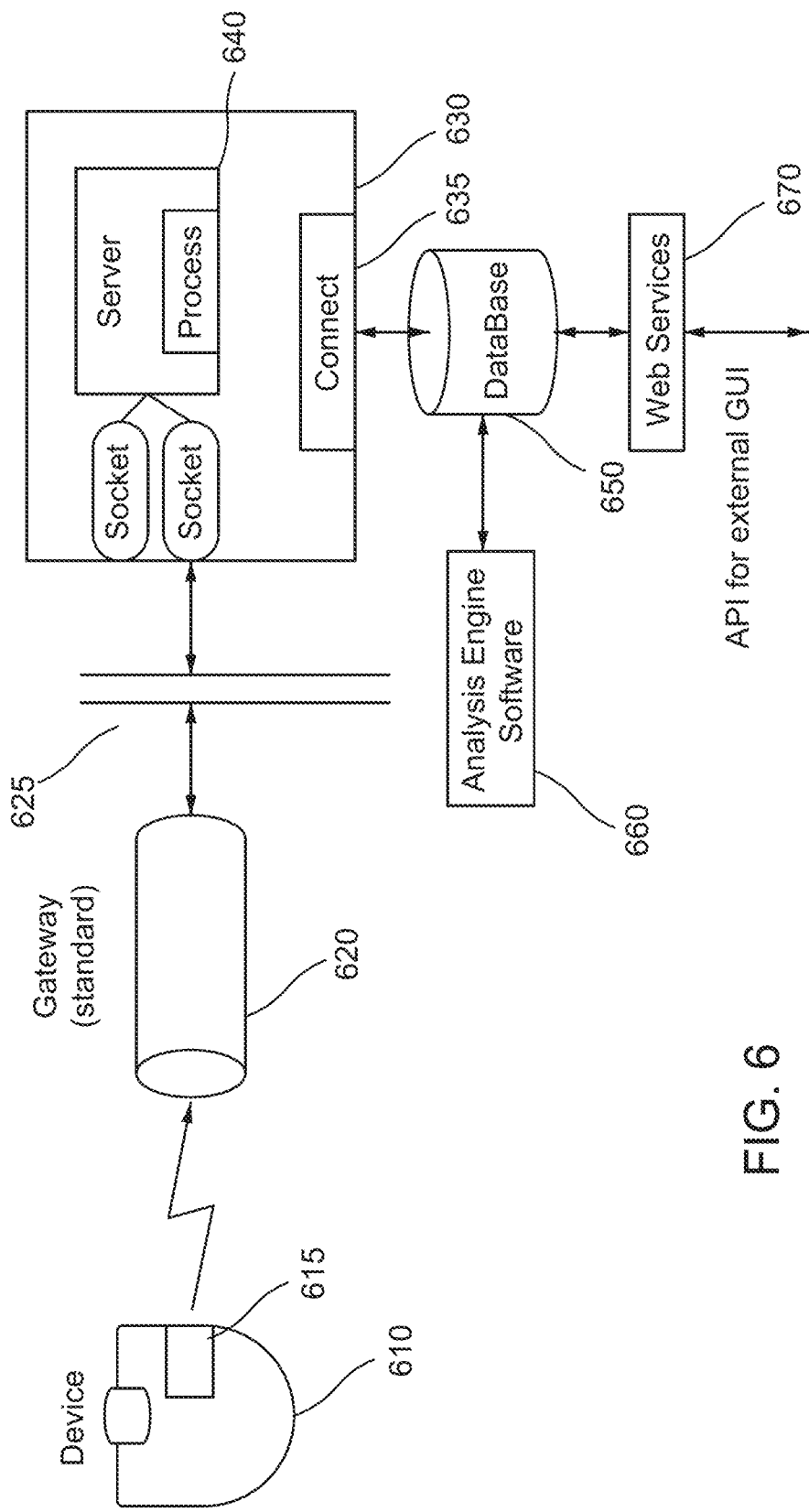
FIG. 6 shows example components of an architecture of an analysis server configured to process and analyze data received from the sensor(s) disclosed herein, according to some embodiments.

FIG. 6 shows example components of an architecture of an analysis server configured to process and analyze data received from the sensor(s) disclosed herein, according to some embodiments. As discussed above, a sensor 610 may transmit physiological and/or environmental data of a patient wearing the sensor 610 to a gateway device 620 (e.g., smartphone) wirelessly. In some embodiments, the transmission may occur via a wireless communication circuit 615, examples of which include one or more circuits configured to communicate via Wi-Fi®, Bluetooth®, a cellular network, and/or the like. The gateway device 620 in turn may transmit the received data to a data analysis system 630 that may include servers 640, databases 650, a software architecture implementing an analysis engine or analysis software 660, and/or the like. The gateway device 620 may transmit the received data via one or more types of communication methods. For example, the data may be transmitted via one or more of TCP/IP over LAN, UDP/HTTP, IEEE 802.11 systems (e.g., ZigBee standards), Bluetooth®, WiFi® and cellular network, e.g., 625.

In some embodiments, the gateway device 620 may be configured to process some of the data received from the sensor 610. For example, the gateway device 620 may be configured to compress the data, detect physiological events from analyzing the data (e.g., detect and/or identify arrhythmia events, patient trigger events, etc.), and/or the like. In some embodiments, the gateway device 620 may also identify, based on analyses of the data, physical and/or electrical conditions of the sensor 610. For example, the gateway device 620 may monitor the performance and/or quality of the power source of the sensor 610 based on the received data. As another example, the gateway device 620 may identify any physical and/or electrical connections problems (e.g., between the sensor 610 and the surface the sensor is attached to, between the sensor 610 and the gateway device 620, etc.) that may occur by analyzing the data received from the sensor 610.

In some embodiments, the gateway device 620 may be configured to interface with a user of the disclosed monitoring system. For example, the gateway device 620 may include a user interface for displaying acquired data, alerts, and/or for receiving input from the user such as patient feedback.

In some embodiments, the databases 650 and/or the analysis engine 660 may reside within a same physical server-side device or may be distributed across multiple server-side devices. The analysis engine 660 is executable on one or more computer processors using code (e.g., computer program(s), computer-readable instructions, machine-readable program(s), human-written or automatically generated program(s) developed within a development environment, and the like) encoded in memory implemented in non-transitory media. In some embodiments, the received data may include RF-based measurements, ECG data, respiration data (as obtained by an accelerometer, for example), activity and/or posture data, and/or the like. In some embodiments, the measurement data may be processed automatically as soon as the file containing the data is transferred to the server 640. Further, detected arrhythmia events & patient trigger events can be logged in the databases 650 for review. In some embodiments, as discussed above, a received data for N number of patients may be processed (and the processing completed) in less than $T_{segment}$ from the time the file containing the data is ready on the server, where $T_{segment}$ represents the file segment time (which can be configurable, and in some embodiments, about 2 minutes). In case of accumulation of numerous files, the most recent recordings may be processed first (LIFO) and priority may be given to files containing patient trigger events. Trigger events may be extracted from recorded measurement file, along with detected arrhythmias.

In some embodiments, the microcontroller of the sensor 610 and the server 640 may be operatively coupled to each other such that the latter controls the former for the tasks of one or more of configuring the microcontroller's measurement and connection parameters and/or effecting the transfer of data saved in the microcontroller's flash memory to the server 640 periodically. In some embodiments, the server 640 can send instructions (e.g., "start recording", "stop recording" commands) and other commands/requests (e.g., configuration changes, status inquiries, etc.) to the sensor 610 (or equivalently to the microcontroller therein) during measurement. In some embodiments, the other commands (e.g., configuration changes, status inquiries, etc.) may be sent only after measurement has stopped.

In some embodiments, the database 650 may serve as a bridge between the server 640 and the graphical user interface (GUI) browser 670. It may contain some or all of the different patients' configurations and acquired data, and the analysis engine 660 may have access to the database for changing configurations, recruiting/dismissing patients, retrieving patient data and detected arrhythmias, retrieving device status and device or usage alerts. In some embodiments, the data analysis system 630 may access the databases 650 via any ay database interface system, an example of which includes an SQL (e.g., an SQLConnect( ) call).

As described above, the server system 640 may communicate notifications and/or alerts to one or more authorized persons or entities (e.g., other critical care response systems). The notifications may be in the form of messages transmitted to desktop computers, pagers, cellular devices, smartphones, personal digital assistants, and the like. For example, an authorized person may use the GUI browser 670 (e.g., accessible through a variety of desktop, laptop, and/or handheld devices) to configure the content, frequency and nature of the notifications and/or alerts. For example, in a particular use scenario, a technician or other designated individual may wish to be notified of a critical arrhythmia event (e.g., a ventricular fibrillation event) occurring on one or more patients. The technician may immediately respond to the event by preparing a relevant report and forwarding to the patient's caregiver.

In some embodiments, the analysis engine 660 may comprise one or more components configured to process the received data. For example, the analysis engine 660 may include an ECG unit or module that is configured to filter the ECG data, perform QRS detection of the ECG data and/or estimate the heart rate (HR) and/or the heart rate variability (HRV) of the wearer of the sensor 610 based on the received data. In some embodiments, the filtering of the ECG data may be accomplished by removing baseline wander, high frequency noise and/or 50/60 Hz interferences. Further, the QRS detector may be a Pan-Tompkins based QRS complex detector. In some embodiments, the QRS detector may be based on the Hilbert transform algorithm. In some embodiments, the QRS detector may be based on the phasor transform algorithm. In some embodiments, the ECG unit estimates the heart rate by removing outliers and averaging over a time window. In general, since the ECG sometimes can suffer from noises and motion artifacts, time windows where the signal is not suitable for arrhythmia detection, heart and respiration rates estimation, etc., may be removed from the analysis.

In some embodiments, the analysis engine 660 may also include an ECG classification unit that is configured to detect and classify the beats and rhythms of the sensor wearer's heartbeat from the received ECG data. For example, the ECG classification unit may detect ventricular ectopic beats, ventricular couplets, short (i.e., non-sustained) runs (e.g., ventricular runs of less than about 30 second duration), long (i.e., sustained) runs (e.g., ventricular runs of greater than about 30 second duration), supraventricular ectopic beats (SVEBs), ventricular couplets, and/or the like. In some embodiments, the ECG classification unit may include a ventricular tachycardia (V-tach or VT) beat detector that detects such beats in the ECG measurements to identify unhealthy electrical activity in the ventricles of the wearer's heart. In some embodiments, the V-Tach beats detected by the ECG classification unit may be the types of beats that go undetected when other detection systems such as the Pan-Tompkins detector are utilized.

In some embodiments, the ECG classification unit may further include a feature extraction unit that is configured to determine various features of the beats classified by the ECG classification unit. For example, the feature extraction unit may calculate beat features including but not limited to QRS width, polarity, maximum-to-min ratio, P-wave existence, and/or the like.

In some embodiments, the analysis engine 660 may comprise an ECG arrhythmia detection module or unit configured to detect one or more of bradycardia, tachycardia, atrial fibrillation episodes, pauses (in the heartbeat of the wearer of the sensor 610), ventricular tachycardia, ventricular runs, bigeminy, trigeminy, multigeminy, supraventricular tachycardia, ventricular fibrillation and heart block detections (e.g., atrioventricular (AV) blocks including first degree, second degree and/or third degree heart blocks). In some instances, the AV second degree blocks may include type I (Mobitz I) and/or type II (Mobitz II) blocks. In some embodiments, a component of the analysis engine 660 configured to detect AV blocks may be configured to determine one or more of the characteristics of the AV block episodes. In some embodiments, the analysis engine 660 component may be configured to record all such episodes within a database (e.g., database 650).

A reporting tool may then be configured to query the database 650 and generate one or more report(s) indicating various statistics involving the episodes, e.g., one or more of the total number of episodes, the duration of the episodes (e.g., depicted in histogram format), provide an ECG strip (e.g., 30 seconds long, 45 seconds long, 1 minute long, 2 minutes long, or 3 minutes long, or other lengths of time therebetween, or more) of an onset, a middle and/or an offset of a longest, a fastest, and/or a slowest episode (e.g., 25 mm/s strip and/or smaller) and/or the duration of the longest episode.

In some embodiments, any one of the above determinations by the analysis engine 660 can include detection of the episodes that may be made with sensitivity better than about 90%, about 95%, about 99%, including values and subranges therebetween. Further, the determinations may possess positive predictive value (PPV) in excess of about 80%, about 85%, about 90%, about 95%, about 99%, including values and subranges therebetween.

In some embodiments, a component of the analysis engine 660 configured to detect bigeminy, trigeminy, multigeminy, and/or the like may be configured to detect any one of these episodes with sensitivity better than about 80%, about 85%, about 90%, about 95%, about 99%, including values and subranges therebetween.

In some embodiments, with respect to bradycardia detections, a bradycardia detector component of the analysis engine 660 can perform at least two types of detections, including detections during the time window where the heart rate is below a threshold and/or when there exists a bradycardia onset/offset with different thresholds for onset and offset. Likewise, for tachycardia detections, a tachycardia detector component of the analysis engine 660 can perform at least two types of detections including detections during the time window where the heart rate is above a threshold and/or when there exists a tachycardia onset/offset with different thresholds for onset and offset. The information collected by these detectors can be stored in the database 650.

Upon analyzing the received ECG data, in some embodiments, a reporting tool may be configured to analyze the stored ECG data in database 650 and report one or more characteristics of the respective bradycardia or tachycardia episode. For example, the reporting tool may report one or more of the total number of bradycardia or tachycardia episodes, the duration of the bradycardia or tachycardia episodes (e.g., depicted in histogram format), provide an ECG strip (e.g., 30 seconds long, 45 seconds long, 1 minute long, 2 minutes long, or 3 minutes long, or other lengths of time therebetween, or more) of an onset, a middle and/or an offset of a longest, a fastest, and/or a slowest portion of the bradycardia or tachycardia episode (e.g., 25 mm/s strip and/or smaller) and/or the duration of the longest bradycardia or tachycardia episode.

As noted above, in some embodiments, any one of these determinations including detection of the bradycardia or tachycardia episodes may be made with sensitivity better than about 90%, about 95%, about 99%, including values and subranges therebetween. Further, the determinations may possess positive predictive value (PPV) in excess of about 80%, about 85%, about 90%, about 95%, about 99%, including values and subranges therebetween.

In some embodiments, a pause detector component of the analysis engine 660 can be configured for detecting pauses in the heartbeat of the wearer of the sensor 610. The pause detector may utilize a configurable threshold (e.g., obtained from the database 650 which may include a patient's record (of ECG data, for example)) to detect a pause. The pause detector may take into effect the diminishing R peaks effect of the received ECG data. Similarly, an asystole condition may be detected. The related pause data can be stored in the database 650. A reporting tool can query the database 650 and generate reports indicating the pause event along with details such as a time of occurrence of the pause event.

In some embodiments, the ECG arrhythmia detection unit further includes an atrial fibrillation (AFib) detector component of the analysis engine 660 that is configured to detect atrial fibrillation (flutter) episodes. For example, the detector may employ the method discussed in K. Tateno and L. Glass, *Automatic detection of atrial fibrillation using the coefficient of variation and density histograms of RR and deltaRR intervals; Medical & Biological Engineering & Computing,* 2001, v. 39, pp. 664-671, the disclosure of which is incorporated herein by reference in its entirety. In some embodiments, the AFib detector may detect atrial fibrillation based on an analysis of sequences of RR and deltaRR values considered as random variables, where RR denotes ventricular interbeat interval on ECG and deltaRR denotes the difference between successive RR intervals. In some embodiments, the ECG data may be analyzed per sliding window of length N centered on each beat. An application of the Kolmogorov-Smirnov test can return the probability of the hypothesis that a set of deltaRR values over a window belongs to standard distribution depending on mean value of RR over the same window. In such embodiments, if the probability provided by Kolmogorov-Smirnov test exceeds a threshold, then the AFib detector may recognize the central beat (or subset of beats around central beat) as atrial fibrillation. In some embodiments, deltaRR may be included for analysis if all three QRS complexes are classified as normal according to some standards. In some embodiments, the segment may be analyzed if the total of normal deltaRR exceeds some threshold. The information relating to AFib is stored in the database 650.

Upon analyzing the received ECG data, in some embodiments, the reporting tool is configured to report one or more of the characteristics of the atrial fibrillation episodes. For example, the reporting tool may determine one or more of the total number of episodes, the duration of the AFib episodes (e.g., depicted in histogram format), provide an ECG strip (e.g., 30 seconds long, 45 seconds long, 1 minute long, 2 minutes long, or 3 minutes long, or other lengths of time therebetween, or more) of an onset, a middle and/or an offset of a longest, a fastest, and/or a slowest AFib episode (e.g., 25 mm/s strip and/or smaller) and/or the duration of the longest episode.

In some embodiments, any one of these AFib determinations including detection of the AFib episodes may be made with sensitivity better than about 75%, about 80%, about 85%, about 90%, about 95%, about 99%, including values and subranges therebetween. In some embodiments, the determination of these characteristics may occur during the period when the sensor 610 is active while worn by a patient (i.e., continuously as the data is received or in a periodic or regular manner (e.g., daily)).

In some embodiments, a VT detector component of the analysis engine 660 can be configured to detect ventricular tachycardia episodes. As discussed above, a V-Tach beat detector may detect ventricular tachycardia beats, labelled ventricular ectopic beats (VEBs). In detecting ventricular tachycardia episodes, in some embodiments, the VT detector searches for consecutive VEBs with rate over a configurable minimal rate, which indicate the occurrence of the VT episodes. The engine 660 can store data related to the VT events in database 650.

In some embodiments, a component of the analysis engine 660 is configured to detect ventricular ectopic singles, couples, triplets, and/or the like may be configured to detect any one of these episodes with sensitivity better than about 90%, about 95%, about 99%, including values and subranges therebetween, and may possess positive predictive value (PPV) in excess of about 80%, about 85%, about 90%, about 95%, about 99%, including values and subranges therebetween. In some embodiments, the analysis engine 660 may also include a detector configured for detecting supraventricular tachycardia (SVT) episodes. In such embodiments, the detection of these episodes may be performed with sensitivity better than about 70%, about 80%, about 90%, about 95%, including values and subranges therebetween Upon analyzing the received ECG data, in some embodiments, the reporting tool is configured to report one or more of the characteristics of the respective VT or SVT episodes. For example, the reporting tool may report on one or more of the total number of episodes, the duration of the episodes (e.g., depicted in histogram format), provide an ECG strip (e.g., 30 seconds long, 45 seconds long, 1 minute long, 2 minutes long, or 3 minutes long, or other lengths of time therebetween, or more) of an onset, a middle and/or an offset of a longest, a fastest, and/or a slowest episode (e.g., 25 mm/s strip and/or smaller) and/or the duration of the longest episode.

In some embodiments, any one of these determinations including detection of the episodes may be made with sensitivity better than about 90%, about 95%, about 99%, including values and subranges therebetween. Further, the determinations related to the supraventricular tachycardia episodes may possess positive predictive value (PPV) in excess of about 50%, about 60%, about 70%, about 80%, about 90%, including values and subranges therebetween.

In some embodiments, a ventricular fibrillation (VF) detector component of the analysis engine 660 may include a machine learning detector, such as a support vector machine (SVM) learning detector. In some embodiments, the machine learning detector may include a random forest machine learning based detector. In some embodiments, the detector may include a neural networks based detector. In some embodiments, a deep learning (deep structured learning or hierarchical learning) based detector may be used. In some embodiments, the VF detector may analyze the raw ECG data directly and may use between 3-10, 10-15, or 15-30 different ECG-based and/or patient medical and biographical history features, and/or other physiological features in analyzing the data. The ECG-based features, for example, may be computed every few seconds with some overlap. For example, some or all of the features may be computed on between a 5-20 seconds time window with a predetermined overlap (e.g., a ¹⁄₆₄, ¹⁄₃₂, ¹⁄₁₆ overlap, ¼ overlap, ½ overlap, or ⅓ overlap, or other overlap value).

Upon analyzing the received ECG data, in some embodiments, the reporting tool is configured to report one or more of the characteristics of the ventricular fibrillation episodes. For example, the reporting tool may determine one or more of the total number of VF episodes, the duration of the episodes (e.g., depicted in histogram format), provide an ECG strip (e.g., 30 seconds long, 45 seconds long, 1 minute long, 2 minutes long, or 3 minutes long, or other lengths of time therebetween, or more) of an onset, a middle and/or an offset of a longest, a fastest, and/or a slowest VF episode (e.g., 25 mm/s strip and/or smaller) and/or the duration of the longest VF episode.

In some embodiments, any one of the above VF determinations including detection of the episodes may be made with sensitivity better than about 95%, about 97%, about 99%, including values and subranges therebetween, and with positive predictive value (PPV) in excess of about 80%, about 85%, about 90%, about 95%, about 99%, including values and subranges therebetween, all for episodes lasting longer than about 2 seconds.

As noted above, besides analyzing the received ECG data, in some embodiments, the analysis engine 660 may comprise RF and/or accelerometer components for analyzing received RF-based and/or accelerometer measurements, respectively. For example, the RF component may be configured to create RF images from the received RF-based measurements by performing band pass filtering and applying fast-Fourier transform (FFT), in some embodiments, the RF component may compute or estimate fluid content of the tissue of the wearer of the sensor 610 on which the RF measurements were performed. For example, if the RF measurements were performed on a lung of a patient using a sensor 610 worn by the patient, in some embodiments, the RF component may calculate the lung fluid level or content of the patient based on RF calculations created by the RF component after processing the RF measurements.

In some embodiments, the accelerometer component of the analysis engine 660 may compute or estimate the respiration rate of the patient or user wearing the sensor 610 by analyzing the accelerometer measurements. In some embodiments, the analysis may be based on peak detection and regularity constraints. For example, the accelerometer component may monitor (e.g., periodically, continuously, etc.) for three channels and perform a principal component analysis (PCA) to select the channel with the longest regularity, which allows the accelerometer component to estimate or calculate the respiration rate.

In some embodiments, the analysis engine 660 may also comprise a component for determining the sensor wearer's physical activity and/or posture based on the received accelerometer measurements. In some embodiments, the component may use the accelerometer measurements with or without regard to the positioning of the sensor on the patient when the accelerometer measurements were taken. For example, the component may use the accelerometer measurements that are obtained from the upper body or torso only. In some embodiments, the component may use the accelerometer measurements (whether taken from the torso or anywhere else on the body) that are determined to indicate the movement of the upper body. Respiration rate and/or fluid related RF measurements are taken when the patient's body is relatively at rest, e.g., while the patient is sitting down and/or lying down. In embodiments where respiration rate and/or fluid related RF measurements are being taken, if the motion level of the device, as calculated from the accelerometer measurements, is above a configurable threshold, the analysis engine 660 may be configured to ignore or flag the related respiration rate and/or fluid related RF measurements as being taken during a period of excessive patient motion.

In some embodiments, the component for determining the sensor wearer's physical activity and/or posture may be configured to distinguish between different classes of activities. For example, the component may classify the activities into three classes, such as: 1) rest 2) walk, and 3) other. In some embodiments, the "other" class may represent some or all activities which may not be described or classified as rest (which include, amongst other activities, sitting and sleeping) or walking. In some embodiments, activities may be classified into the walk class based on the strength and/or periodicity of the activity, since walking can be a periodic and strong power activity which may last for an extended period of time (in contrast to abrupt changes such as changing position between sitting and standing, for example).

Similarly, in some embodiments, the component for determining the sensor wearer's physical activity and/or posture may classify the postures into a plurality of classes. For example, the component may classify the postures into three classes, such as supine, reclined and upright.

In some embodiments, a decision tree may be used to distinguish between those three classes, with accelerometer measurements being classified every few seconds (e.g., half a second, one second, two seconds, etc.). Further, a second layer of algorithm (e.g., erosion and dilation) may receive these decision tree's classes and smooth out the results based on the confidence received, thereby facilitating the covering of some non-continuous "walk" sections and eliminating "lonely" sections. For example, if the decision tree prediction is made of 10 seconds of "walking" (in high probability), 5 seconds of "other" (but with a medium probability for walking) and then another 10 seconds of "walking", this second layer of algorithm would probably return that we had a continuous 25 sec of "walking". On the other hand, if it indicated there is only one sec of "walking" between many "other" class, it would eliminate this lonely "walking" class.

Figure 7:
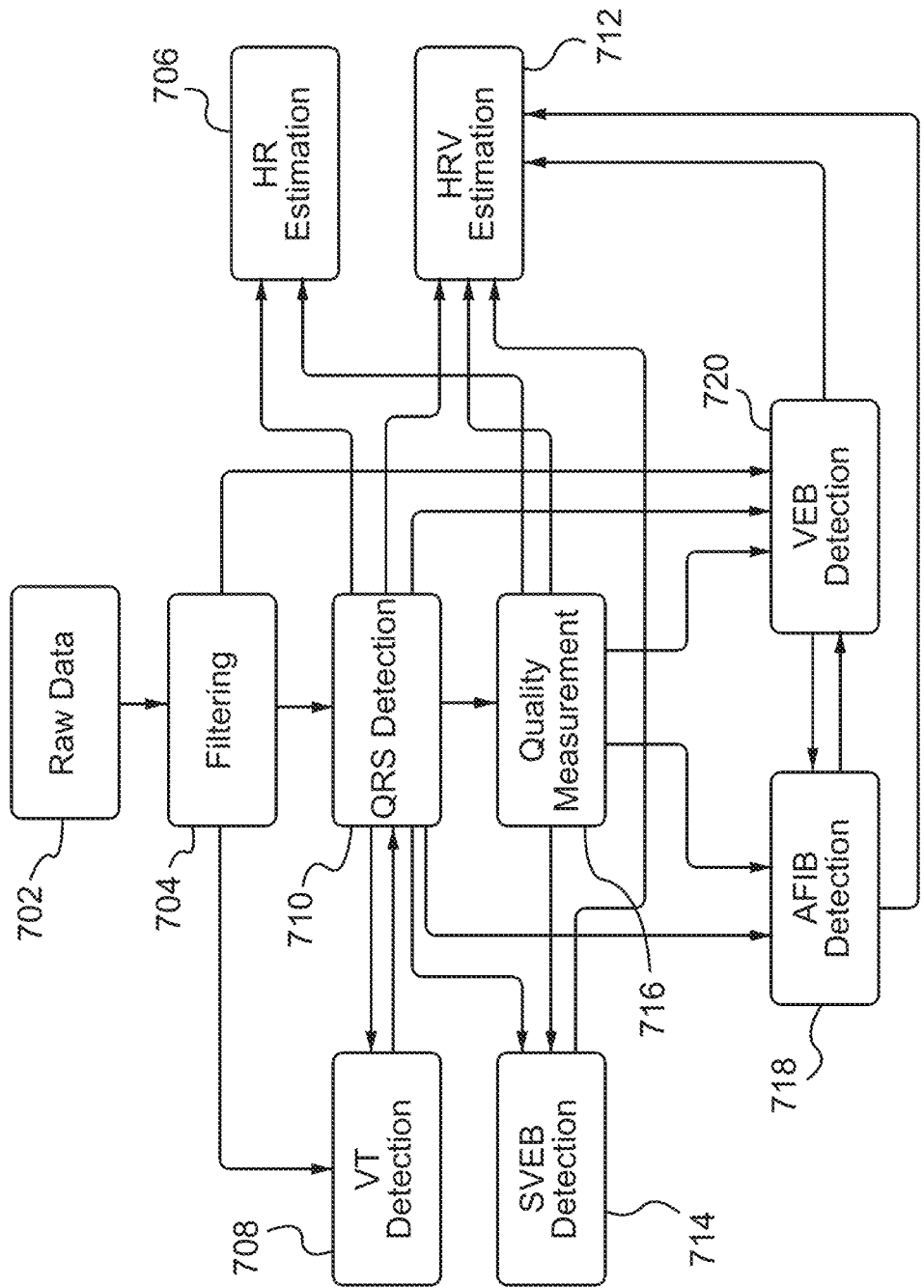
FIG. 7 shows an example block diagram of the processing of electrocardiogram (ECG) data by the arrhythmia and fluid monitoring system disclosed herein, according to some embodiments.

FIG. 7 shows an example block diagram of the processing of electrocardiogram (ECG) data by the arrhythmia and fluid monitoring system disclosed herein, according to some embodiments. Specifically, the ECG processing, which can be performed by the server 630 (and the analysis engine 660), on a data set received from the sensor 610. Accordingly, raw data 702 is filtered 704 (i.e., as part of signal conditioning), to remove, for example, baseline wander, high frequency noises and 50/60 Hz interferences.

Accordingly, with respect to QRS detection 710, a Pan-Tompkins based QRS complex detection can be used:
1. Find the derivative and square the result:

$$y_2 = \left(\frac{dy_1}{dt}\right)^2$$

2. Apply a moving average:

$$y_3 = \text{MovingAverageFilter} * y_2$$

3. Apply adaptive power threshold to locate the QRS complexes; and
4. Find the locations of R peaks within the QRS complexes (peak finding). Denote the R peaks location sequence as $\{R_i\}$ With respect to HR (heartrate) estimation 706, the following process can be implemented (i.e., via computer instructions/hardware):
1. The input to the heart rate estimation stage is the locations of the R-peaks, $R_i$.
   a. Heart rate can be calculated for moving, overlapping, 1 minute windows.
   b. Each window can be tested for validity. For example, if the window is not valid, no heart rate result is provided for that time window.
   c. Validity can be determined based on several requirements:
      i. No signal saturation; and/or
      ii. $RR_i$ distribution is not an exponential distribution
   d. For valid windows, the sequence of RR intervals $RR_i$ can be determined $$RR_i = R_{i+1} - R_i$$

e. If there are outlying RR values, 2 most extreme $RR_i$ outliers are removed (in some embodiments). Outliers can be defined by the Thompson Tau test.
   f. The heart rate can then be computed by $$\frac{60}{\langle RR_i \rangle}$$

With respect to ECG quality 716 estimation, detected low quality portions of the ECG are ignored, and quality detection is based on:
1. Signal Saturation Detection
   The saturation level of the ECG signal collection device are used as part of input parameters.
2. Noise Estimation
   A noise index is estimated, ECG parts where the noise index is greater than 14. It will be appreciated that this is equivalent to a requirement of SNR=0.5 dB when tested on Gaussian noise.

With respect to SVEB (supraventricular ectopic beat) detection 714, each beat can be classified into one of the three categories: Normal, Ventricular Ectopic Beat (labeled as "VEB" in the output), or Supraventricular ectopic beat (labeled as "SVEB" in the output).

SVEB Detection can comprise the following methodology:
1. SVEB are detected based on RR interval, and on the preceding VEB detection.
2. Ectopic beats (RR interval 19% longer than previous RR interval), which are not already classified as ventricular ectopic beats (VEBs), are classified as SVEBs.
3. In addition the histogram of the RR interval is analyzed. If there are two clusters of RR intervals, short and long, the short ones are classified as SVEBs, unless they are already classified as VEBs.

Remaining beats, which were not classified as VEB/SVEB are classified as Normal.

In some embodiments, VEB (Ventricular Ectopic Beats) Detection 720, can be based on Support Vector Machine (SVM) classification using the Radial Basis Function (RBF) kernel. The VEB detector can employ the following 8 features (depending upon the embodiment, one or more, a plurality, of the following):
1. Previous $RR_i/3$ peak average RR (previous, current, next peaks)
2. Current $RR_i/3$ peak average $RR_i$
3. QRS width/3 peak average QRS width
4. Previous $RR_i/100$ peaks average $RR_i$ (previous 50, next 50 peaks)
5. Current QRS width/average 100 peaks width
6. Current QRS height/100 peak average height
7. std (100 peak $RR_i$)/mean(100 peak $RR_i$)
8. $1^{st}$ PCA coefficient of current QRS complex, based on 100 QRS complexes. To speed up processing, only the $1^{st}$ eigenvector is calculated VT (ventricular tachycardia) detection 708 can be based on the finding/determination of at least five (5) consecutive VEBs with rate over a configurable minimal rate (e.g., as determined by the user).

In some embodiments, AFib (atrial fibrillation) 718 detection can be implemented as follows. For AFib 718 detection, for example, "RR" can denote ventricular interbeat interval in an ECG signal and "DeltaRR" can denote the difference between successive RR intervals. Accordingly, detection of atrial fibrillation can be based on analysis of sequences of RR and DeltaRR values considered as random variables. ECG is analyzed per sliding window of length N centered on each beat. Kolmogorov-Smirnov test returns probability of hypothesis that set of DeltaRR values over window belongs to standard distribution depending on mean value of RR over same window. Standard distributions were extracted from referenced atrial fibrillation intervals at MIT atrial fibrillation database (afdb). If the probability provided by Kolmogorov-Smirnov test exceeds a threshold, then a central beat (or subset of beats around central beat) is detected as atrial fibrillation. DeltaRR is included for analysis if all three QRS complexes are classified as normal according to standard. Segment is analyzed if total of normal DeltaRR exceeds threshold.

Accordingly, the system can be configured to detect at least one of the following (and preferably a plurality, and in some embodiments, all): Bradycardia, Tachycardia, Atrial Fibrillation, Pause, Ventricular Runs, Ventricular Bigeminy/Ventricular Trigeminy, Ventricular Tachycardia, Supraventricular Tachycardia, 2nd Atrioventricular (AV) block, and 3rd Atrioventricular (AV) block.

With respect to Bradycardia, two types of detections can be performed: time window where rate below a threshold T1, as determined by the user and passed as an input, and Bradycardia onset/offset, with different thresholds for onset and offset, T1 and T2, T2<=T1 (the thresholds are inputs to a library).

With respect to Tachycardia, two types of detections can be preformed: at time window, where rate is above a threshold T1, as determined by the user and passed as input, and Tachycardia onset/offset, with different thresholds for onset and offset, T1 and T2, T2>=T1 (the thresholds are inputs to the library).

With respect to Pause detection, a pause threshold can be determined by the user and passed as an input to the library. Pause detection can be based on previously detected QRS complexes, and the algorithm takes into account the "diminishing R peaks" effect.

With respect to HRV (heart rate variability) 712, it is measure by the variation of the heart beat-to-beat interval.

Sample Results from an Example Implementation of the Disclosed System

Figure 8:
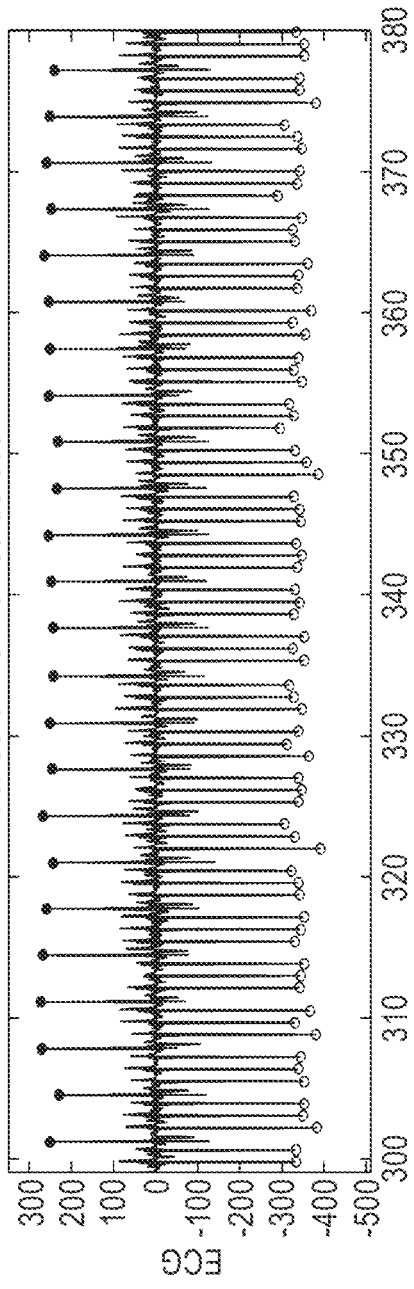
FIG. 8 shows a sample plot illustrating ventricular ectopic beats (VEBs) detection from an example implementation of the arrhythmia and fluid monitoring system disclosed herein, according to some embodiments.
Figure 9:
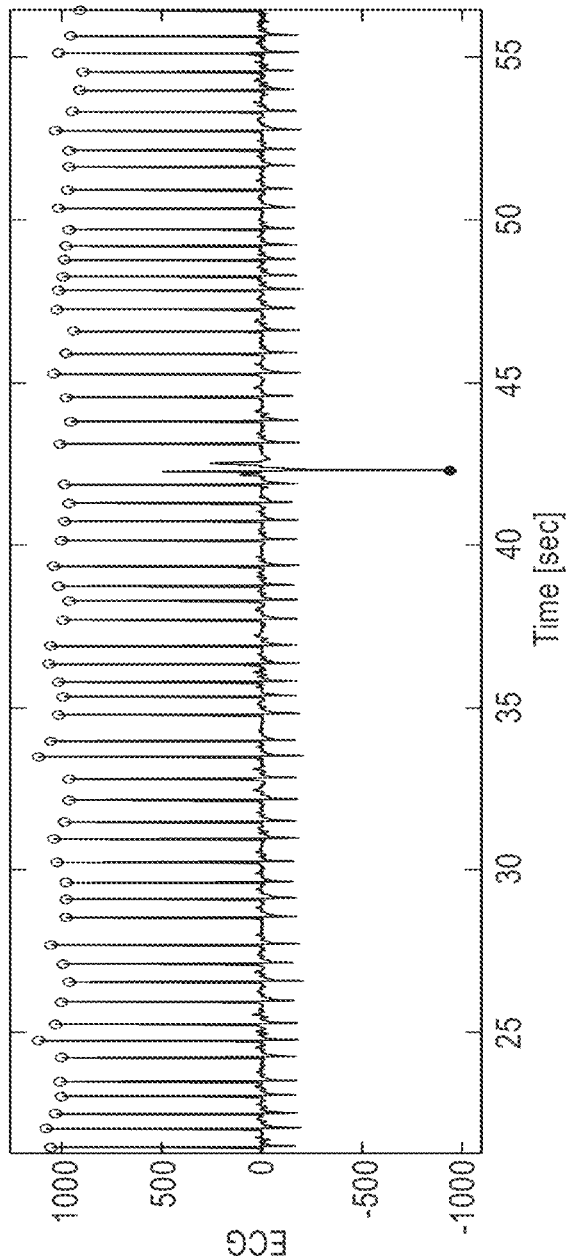
FIG. 9 shows a sample plot illustrating atrial fibrillation detection from an example implementation of the arrhythmia and fluid monitoring system disclosed herein, according to some embodiments.
Figure 10:
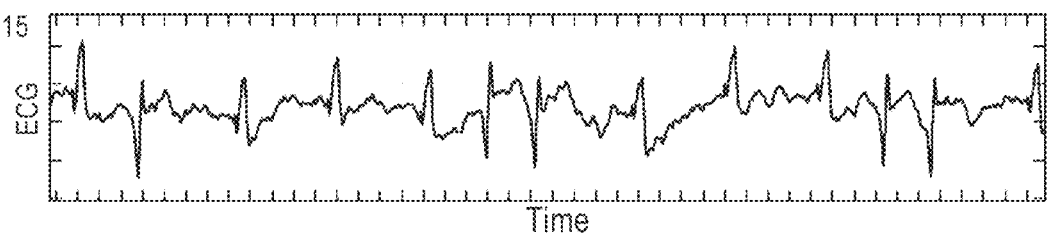
FIG. 10 shows an example clinical report that can be produced by the disclosed arrhythmia and fluid monitoring system after ECG analysis of data received from a sensor worn by a patient, according to some embodiments.
Figure 10:
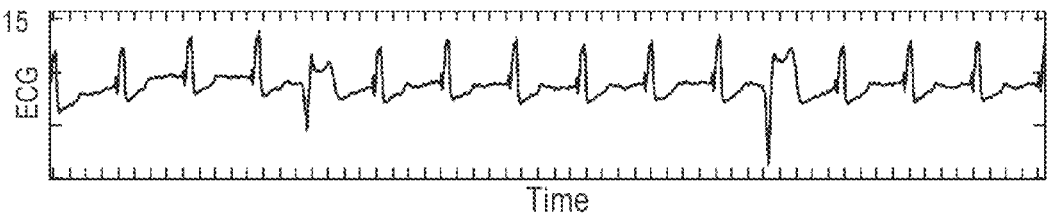
Figure 10:
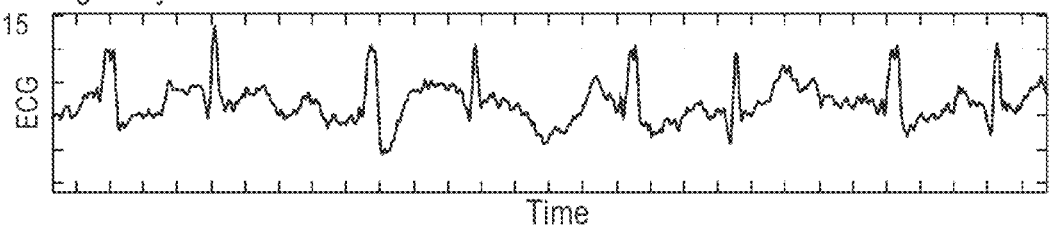
Figure 10:
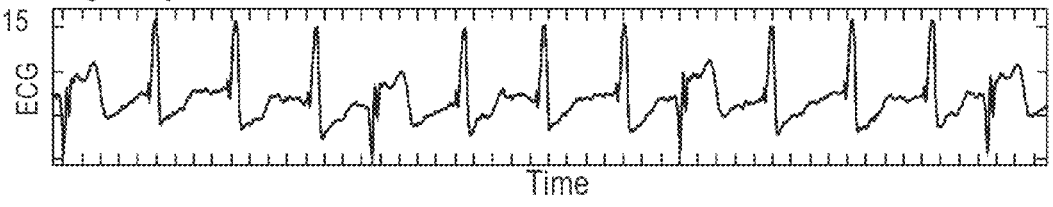
Figure 11:
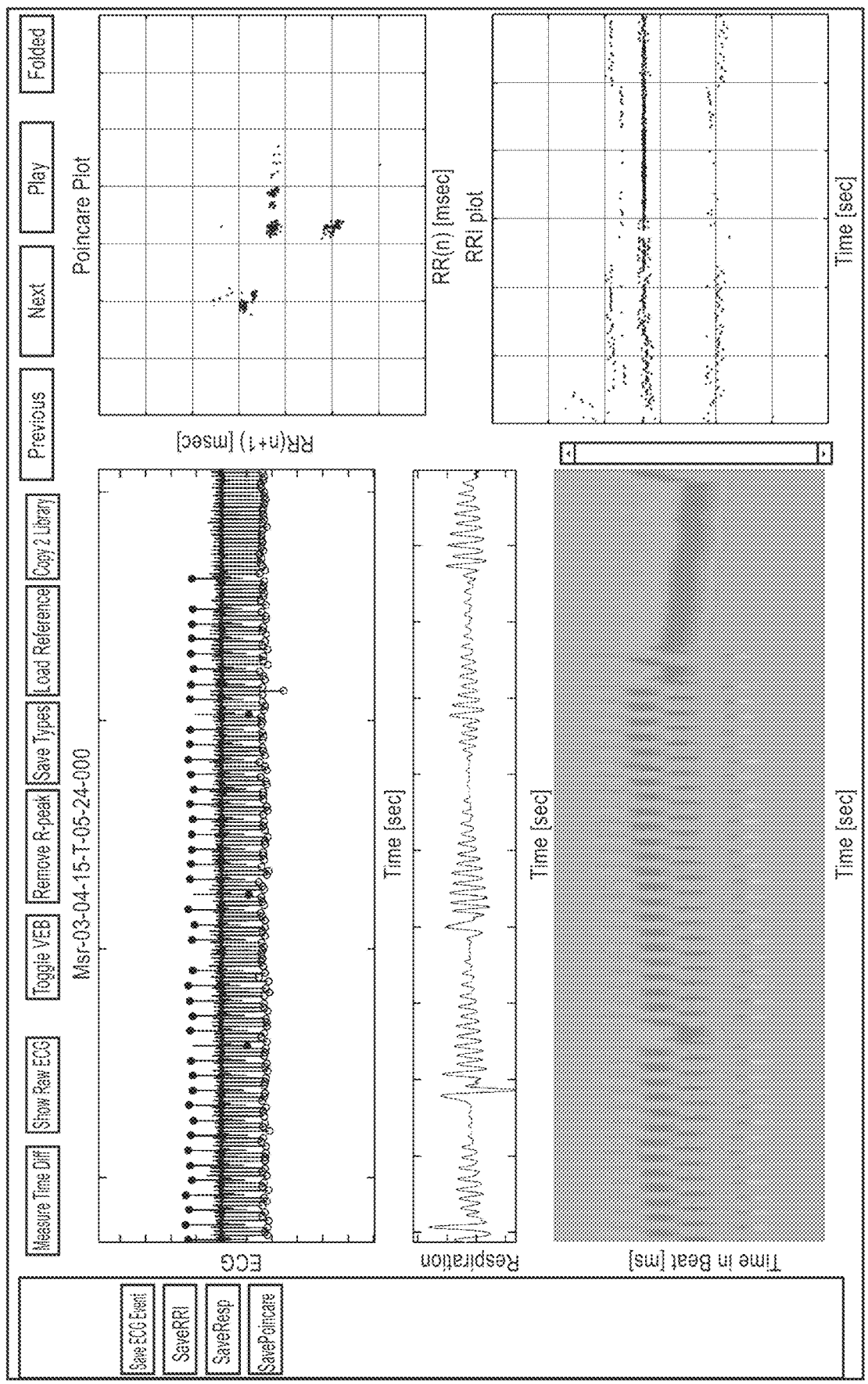
FIG. 11 shows an example visualization tool that allows a user such as a health care provider to analyze received ECG, respiration and the like data in a graphical setting, according to some embodiments.
Figure 12B:
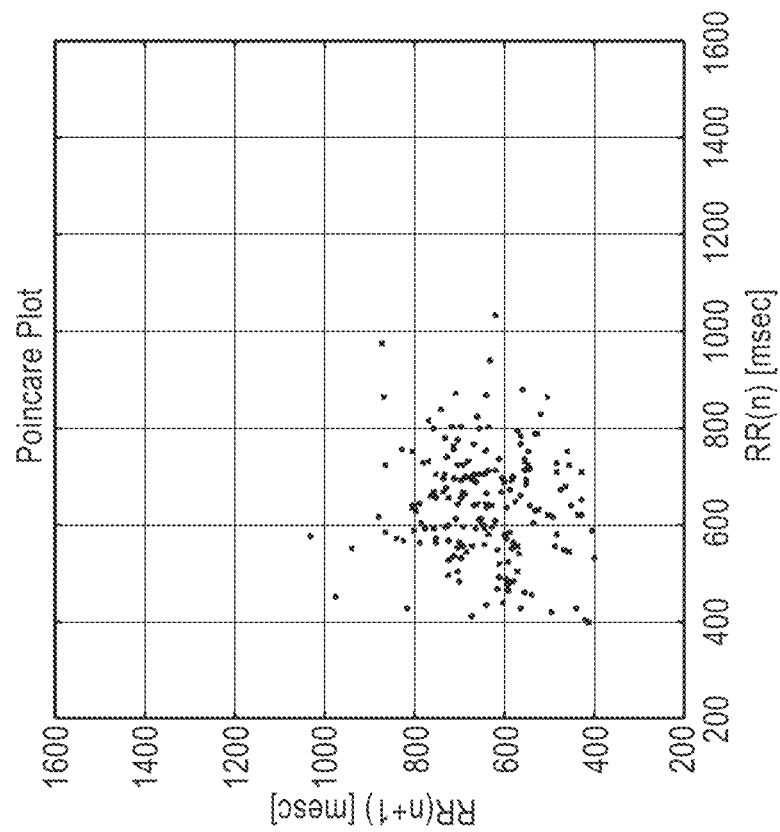
Figure 12A:
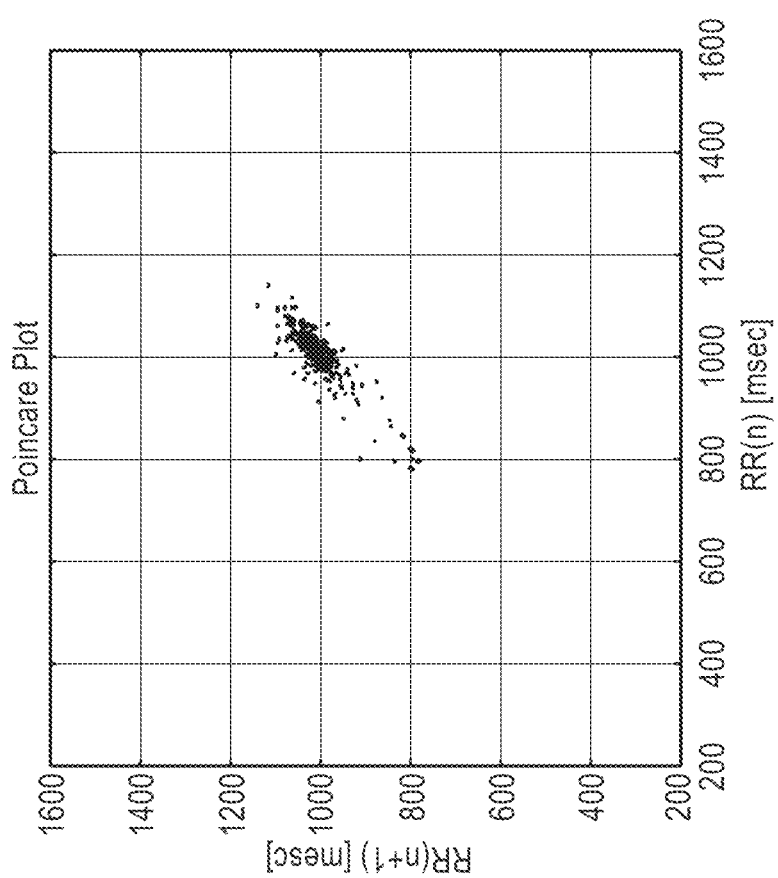
Figure 13A:
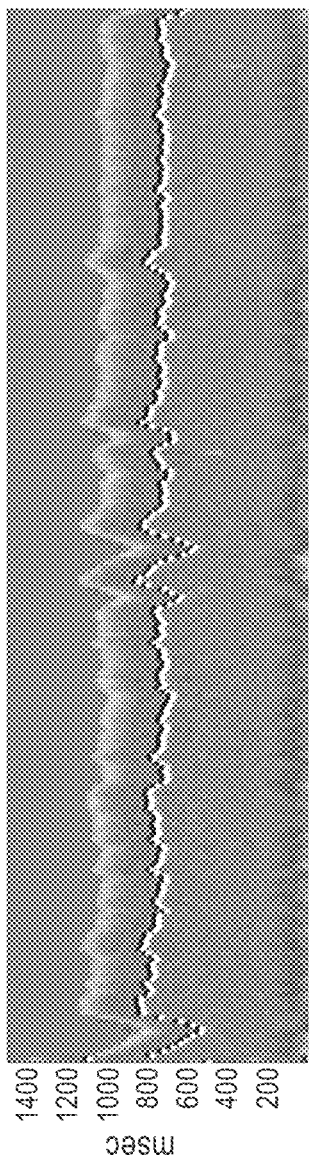
FIGS. 13A-C show example visualization tools utilizing pseudo-color plots to detect and analyze sinus rhythm (FIG. 13A), atrial fibrillation episode (FIG. 13B) and trigeminy (FIG. 13C), according to some embodiments.
Figure 13B:
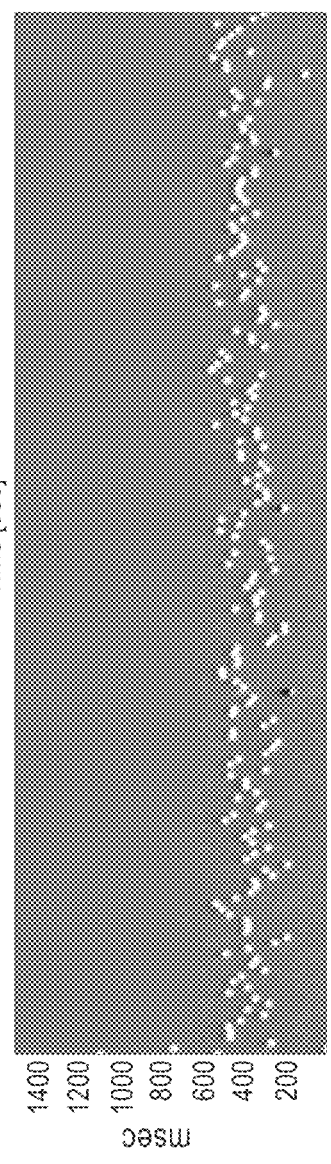
Figure 13C:
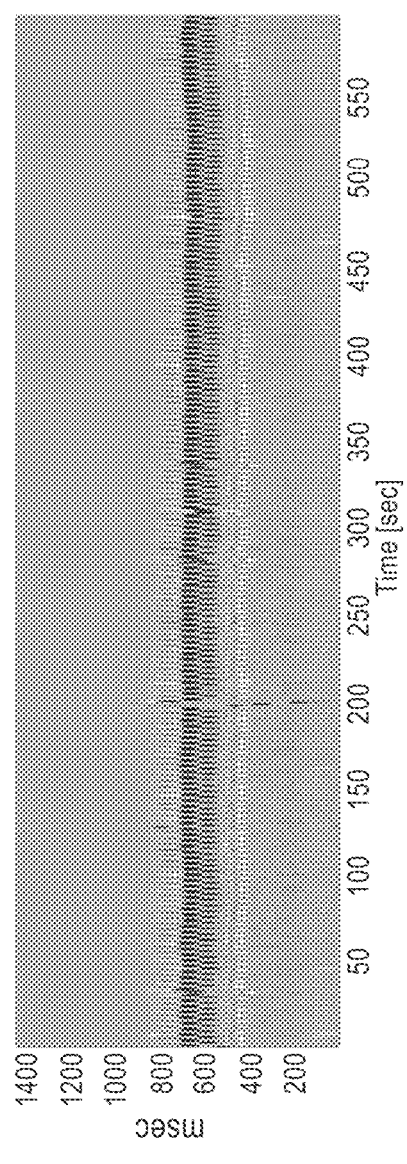

In some embodiments, FIGS. 8-13 show sample results from an example implementation of the arrhythmia and fluid monitoring system disclosed herein. FIG. 8 shows an example plot of a ventricular ectopic beats, ventricular runs and ventricular tachycardia detected using a combination of a linear classifier (i.e., machine learning) and a set of heuristic detectors. FIG. 9 shows an example plot depicting the detection of atrial fibrillation that is based on an analysis of sequences of RR Interval (RRI) and deltaRRI (ΔRRI). In producing the plot, the distribution of the RRI and ΔRRI is compared with expected AF distribution and a decision is made per time window. FIG. 10 shows an example clinical report that can be produced by the disclosed arrhythmia and fluid monitoring system (e.g., the server) after ECG analysis of data received from a sensor worn by a patient. FIGS. 11-13 show an example visualization tool that allows a user such as a health care provider to study and investigate received ECG data in a graphical setting. For example, FIGS. 12A-C and 13A-C show respectively Poincare plot and pseudo color plot visualizations that allow for human detection of the rhythm type, where the Poincare plots of FIGS. 12A-C respectively depicting sinus rhythm, atrial fibrillation and trigeminy. With reference to FIG. 13A-C, the folded pseudo color plot shows a matrix where each column is a short time interval of approximately a single heartbeat's duration, where the color at each point in the column corresponds to the ECG potential. ECGs are thereby folded so that different rhythm types may have different characteristic "finger-print" in this representation, e.g. a constant rhythm will manifest as a straight line and bigeminies as double lines. This representation allows for identifying certain arrhythmia types while viewing a long time window. Accordingly, such feature representations include:

Simultaneous presentation of ECG & Accelerometer data on a common time scale to assist in detecting artifacts intervals;

Simultaneous presentation of ECG and Poincaré plots (also known as return maps) to assist in rhythm classification; and Automatic annotated presentation of ECG morphology and RR intervals for easier technician review.

As noted above, in addition to events, in some embodiments, trends associated with collected physiological data (from the data segments) may be produced for one and/or another patient and displayed (e.g., display device, printed report) for a technician, doctor, healthcare worker or a patient. Such trends may include changes over a configurable period of time (e.g., order of minutes, hours, days, weeks, or months) of certain physiological parameters derived from the ECG, accelerometer, and RF measurement data, among others. The system may also produce maximums and minimums of these values over a time period (minute, hour, day, week, month, or year). For example, the trends may be displayed to a technician for inclusion in a report to a physician. Such trends can include, for example, displaying the variation in one or more of a patient's heart rate, activity patterns, sleep patterns (along with sleep times), posture patterns, and other patterns in physiological parameters over the period of device use.

An Example Implementation of the Disclosed Embodiments

When using the disclosed sensor, in some embodiments, there are scenarios that involve the removal of the adhesive patch from the skin of a body, either by involving the transfer of sensors from old patient to new patient or when replacing faulty sensors. For example, when a device is in a charger or on a patient in error, it can be disassociated from the patient through a server action. Similarly, if the device is newly assigned to a patient, the device can be associated with a new patient through a server action. In some embodiments, certain operational modes of the sensor may not include all aspects of the sensor's operational capability. For example, situations involving automatic built-in tests, regulation tests, debugging, handling when the sensor is faulty, etc., one or more features of the sensor may not be activated or operational (or may operate differently than when the sensor is fully or normally operational) while the sensor itself is operating. For example, when debugging a faulty system, in some embodiments, transmission may be conducted via a single specific frequency by allowing configuring a specific frequency and triggering start/stop transmission.

| | |
|---|---|
| Overall dimensions | Smaller than about 55 mm × about 70 mm × about 17 mm |
| Maximum weight | Less than about 70 grams |
| ECG attachment | Embedded in adhesive patch |
| Gel | using hydrogel embedded in patch |
| Device liquid/dustproofing | Ultrasonic sealing, tested according to IP67 |
| Package | Contents: 1 device, charging cradle, User manual and disposable patches; Patches must be packed appropriately to avoid glue dehydration. |
| Labelling | Device should be labelled with serial number & FCC ID. Label must withstand environmental conditions according to IP67 |
| Soft feel | Rubber like feel, little or no sharp edges |
| Push-Button | Multipurpose; designed to be used by technician; protected from accidental activation by the patient to preserve power; Used for reset, pairing and to initiate communication |
| LED | Multipurpose; dual color; indicates battery status, pairing, errors, BT connection. |
| Device-in-patch sensing | electrical-connection |
| Buzzer | Audio notification, between about 1 and about 3 KHz and over about 60 dBSPL intensity at a distance of 1 m. |
| PCB placement and case closure | Without screws |
| Drop protection | Device is designed to comply with drop tests according to standard IEC 60601-1 and 60601-1-11 |

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be an example and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure. Embodiments disclosed herein may also be combined with one or more features, as well as complete systems, devices and/or methods, to yield yet other embodiments and inventions. Moreover, some embodiments, may be distinguishable from the prior art by specifically lacking one and/or another feature disclosed in the particular prior art reference(s); i.e., claims to some embodiments may be distinguishable from the prior art by including one or more negative limitations.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of" will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is currently claimed:

1. A physiological patient monitoring system, comprising:
a remote server; and
a physiological monitoring device comprising a housing disposed on a patch, the patch being configured for removable attachment to or proximate the skin of a patient, the physiological monitoring device comprising:
at least one memory;
at least one antenna disposed on the housing and configured to transmit radio-frequency (RF) waves towards a targeted portion of an internal tissue of the patient and receive reflected RF waves from the internal tissue;
RF circuitry in communication with the at least one memory and configured to perform an RF-based measurement of a thoracic fluid level of the patient during a predetermined time period by:
directing the transmission of the RF waves in the range of 500 MHz to 5 GHz towards the targeted portion of the internal tissue, and
processing the reflected RF waves to determine and store a plurality of RF parameters related to the thoracic fluid level of the patient in the at least one memory;
a pair of ECG electrodes and associated circuitry in communication with the at least one memory and configured to:
continuously acquire ECG signals of the patient, and
storing the acquired ECG signals as a plurality of continuously acquired ECG data segments of preconfigured durations in the at least one memory;
at least one three-axis accelerometer and associated circuitry configured to monitor for at least one of patient posture and movement information; and
transceiver circuitry configured to receive and transmit patient information to the remote server by:
controlling continuous transmission of the continuously acquired ECG signals of the patient to the remote server by transmitting each of the plurality of stored continuously acquired ECG data segments immediately after an ECG data segment of the continuously acquired ECG data segment is stored in the memory of the physiological monitoring device during the acquisition of the ECG signals of the patient, and
controlling scheduled transmission of the plurality of RF parameters from the RF-based measurement during the predetermined time period;
wherein the remote server comprises at least one processor configured to execute computer-executable instructions encoded in a memory in communication with the at least one processor, the at least one processor configured to:
receive the continuously transmitted continuously acquired ECG signals of the patient and monitor for a cardiac event based on analyzing the continuously acquired ECG signals, and
receive and analyze the plurality of RF parameters to determine a thoracic fluid metric corresponding to the thoracic fluid level of the patient on establishing successful completion of at least one of patient posture and movement tests based on at least one of patient posture and movement information taken via the at least one three-axis accelerometer.

2. The system of claim 1, wherein the at least one processor of the remote server is configured to analyze the continuously acquired ECG signals and determine information relating to one or more of a heart rate, atrial fibrillation, flutter, supraventricular tachycardia, ventricular tachycardia, pause, AV block, ventricular fibrillation, bigeminy, trigemini, ventricular ectopic beats, bradycardia, and tachycardia.

3. The system of claim 2, wherein the at least one processor of the remote server is configured to determine and store the thoracic fluid metric relative to a baseline thoracic fluid level of the patient.

4. The system of claim 1, wherein the at least one processor of the remote server is configured to issue a notification on detecting an arrhythmia condition as the cardiac event within about 1 to about 15 minutes from at least one of: an onset of the cardiac event, when the monitoring device detects the cardiac event, and when the remote server receives a first ECG data segment containing information relating the cardiac event.

5. The system of claim 4, wherein the at least one processor of the remote server is configured to issue the notification concerning the cardiac event within about 5-15 minutes from the onset of the cardiac event.

6. The system of claim 1, wherein the at least one processor of the remote server is configured to analyze the patient posture information and determine whether the patient is in at least one of a supine, lying on a first side, lying on a second side, reclined, sitting up, and upright state during the predetermined time period when the RF-based measurement is being carried out.

7. The system of claim 1, further comprising a gateway configured to relay the patient information from the monitoring device to the remote server, and wherein the gateway is configured to buffer the patient information.

8. The system of claim 1, the physiological monitoring device further comprising a respiration sensor, wherein the at least one processor of the remote server is configured to receive data from the respiration sensor, and the at least one processor is configured to determine one or more metrics related to a respiration of the patient.

9. The system of claim 1, wherein the patch comprises a first side configured to removably affix to the skin of the patient, and a second side configured to removably receive the housing.

10. The system of claim 9, wherein the first side of the patch includes an adhesive for removably affixing the patch to the skin of the user.

11. The system of claim 1, wherein the housing further comprises a display configured to at least present information on at least one of the operation, condition, and function of at least one of the RF circuitry, the transceiver circuitry, and the system.

12. The system of claim 1, wherein the system further comprises a sensor configured to respond to an engagement by the patient indicating possible symptoms.

13. The system of claim 1, wherein the patch is configured to be disposable.

14. The system of claim 1, wherein the pair of ECG electrodes are embedded in the patch.

15. The system of claim 1, wherein the at least one processor of the remote server is configured to analyze the movement information and determine at least one of physical activity or respiration rate of the patient.

16. A physiological patient monitoring method comprising:
   directing, by a physiological monitoring device, transmission of RF waves towards a targeted portion of an internal tissue of a patient;
   receiving, by the physiological monitoring device, reflected RF waves from the internal tissue;
   processing, by a processor of the physiological monitoring device, the reflected RF waves to determine and store a plurality of RF parameters related to a thoracic fluid level of the patient in at least one memory of the physiological monitoring device;
   continuously acquiring, at the physiological monitoring device, ECG signals of the patient via a pair of ECG electrodes;
   storing, by the physiological monitoring device, the continuously acquired ECG signals as a plurality of continuously acquired ECG data segments of preconfigured durations in the at least one memory of the physiological monitoring device;
   monitoring, by the physiological monitoring device, at least one of patient posture and movement information via a three-axis accelerometer and associated circuitry in the physiological monitoring device; and
   transmitting patient information from the physiological monitoring device to a remote server by:
      controlling continuous transmission of the continuously acquired ECG signals of the patient to the remote server by transmitting each of the plurality of stored continuously acquired ECG data segments immediately after an ECG data segment of the plurality of continuously acquired ECG data segments is recorded and stored in the memory of the physiological monitoring device during the acquisition of the ECG signals of the patient;
      controlling scheduled transmission of the plurality of RF parameters from the at least one memory; and
      receiving, at the remote server, the continuously acquired ECG signals of the patient and monitoring for a cardiac event based on analyzing the continuously acquired ECG signals, and
   analyzing, at the remote server, the plurality of RF parameters to determine a thoracic fluid metric corresponding to the thoracic fluid level of the patient on establishing successful completion of at least one of patient posture and movement tests based on at least one of patient posture and movement information taken via the three-axis accelerometer.

17. The method of claim 16, further comprising issuing, by the remote server, one or more notifications for the cardiac event within between about 1 to about 15 minutes from at least one of an onset of the cardiac event, when the monitoring device detects the cardiac event, and when the remote server receives a first ECG data segment containing information relating the cardiac event.

18. The method of claim 16, wherein the cardiac event comprises one or more of an atrial fibrillation event, a flutter event, a supraventricular tachycardia event, a ventricular tachycardia event, a pause event, an asystole event, an AV block event, a ventricular fibrillation event, a bigeminy event, a trigeminy event, a ventricular ectopic beat, a bradycardia event, and a tachycardia event.

19. The method of claim 16, further comprising determining and storing, at the remote server, a baseline RF-based measurement corresponding to a baseline thoracic fluid level of the patient.

* * * * *

UNITED STATES PATENT AND TRADEMARK OFFICE
CERTIFICATE OF CORRECTION

| | | |
|---|---|---|
| PATENT NO. | : 11,020,002 B2 | Page 1 of 1 |
| APPLICATION NO. | : 16/041402 | |
| DATED | : June 1, 2021 | |
| INVENTOR(S) | : Uriel Weinstein et al. | |

It is certified that error appears in the above-identified patent and that said Letters Patent is hereby corrected as shown below:

On the Title Page

Item (72), Line 8, Inventors, Replace:
"Arkadi Averbuch"
With:
--Arkadi Averboukh--.

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*